United States Patent
O'Brien et al.

(10) Patent No.: US 9,815,894 B2
(45) Date of Patent: Nov. 14, 2017

(54) USE OF RESLIZUMAB TO TREAT MODERATE TO SEVERE EOSINOPHILIC ASTHMA

(71) Applicants: Christopher O'Brien, Lafayette Hill, PA (US); James Zangrilli, Philadelphia, PA (US); Tushar Shah, Flemington, NJ (US)

(72) Inventors: Christopher O'Brien, Lafayette Hill, PA (US); James Zangrilli, Philadelphia, PA (US); Tushar Shah, Flemington, NJ (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 14/838,503

(22) Filed: Aug. 28, 2015

(65) Prior Publication Data

US 2016/0102144 A1  Apr. 14, 2016

Related U.S. Application Data

(60) Provisional application No. 62/047,248, filed on Sep. 8, 2014, provisional application No. 62/091,150, filed on Dec. 12, 2014, provisional application No. 62/168,007, filed on May 29, 2015, provisional application No. 62/191,690, filed on Jul. 13, 2015.

(51) Int. Cl.
| | |
|---|---|
| *C07K 16/24* | (2006.01) |
| *A61K 39/395* | (2006.01) |
| *A61K 8/63* | (2006.01) |
| *A61K 9/00* | (2006.01) |
| *A61K 9/72* | (2006.01) |
| *A61K 39/00* | (2006.01) |

(52) U.S. Cl.
CPC .............. *C07K 16/244* (2013.01); *A61K 8/63* (2013.01); *A61K 9/0019* (2013.01); *A61K 2039/505* (2013.01); *A61K 2039/507* (2013.01); *A61K 2039/545* (2013.01); *C07K 2317/24* (2013.01); *C07K 2317/76* (2013.01)

(58) Field of Classification Search
None
See application file for complete search history.

(56) References Cited

FOREIGN PATENT DOCUMENTS

| WO | WO 2009/120927 | 10/2009 |
|---|---|---|
| WO | WO 2011/156000 | 12/2011 |
| WO | WO 2012/083132 | 6/2012 |

OTHER PUBLICATIONS

Nair et al, New England Journal of Medicine, 2009, vol. 360, No. 10, pp. 985-993.*
McCallister et al, American Journal of Respiratory and Critical Care Medicine, Aug. 18, 2011, vol. 184, pp. 1096-1097.*
Walsh et al, Biologics: Targets and Therapy; 2013, vol. 7, pp. 7-11.*
Mukherjee et al., "Anti-IL5 Therapy for Asthma and Beyond", WAO Journal, 7:32, pp. 1-14, 2014.
Barnes et al., "Inflammatory Mediators of Asthma: An Update", Pharmacological Reviews, vol. 50, No. 4, pp. 515-595, Jun. 2014.
Park, "Eosinophilic Bronchitis, Eosinophilia Associated Genetic Variants, and notch Signaling in Asthma" Allergy Asthma Immunol Research, 2(3), pp. 188-194, Jul. 2010.
Adis R&D, Mepolizumb, 240563, Anti-IL-5 Monoclonal Antibody—Glaxo Smith Kline, Anti Interleukin-5 Monoclonal Antibody—Glaxo Smith Kline, SB 240563, Drugs R D; 9(2); pp. 125-130; 2008.
Bousquet et al., "Eosinophilic Inflammation in Asthma", The New England Journal of Medicine, 323: 1033-1039; 90 pages; Oct. 1990.
Leckie, "Ant-interleukin-5 Monoclonal Antibodies: Preclinical and Clinical Evidence in Asthma Models", Am J Respir Med; 2(3); pp. 245-259; 2003.
Castro, "Reslizumab for Poorly Controlled, Eosinophilic Asthma", A Randomized, Placebo-controlled Study; American Journal of Respiratory and Critical Care Medicine; vol. 184; pp. 1125-1132; Nov. 2011.
Nucala (Mepolizumab) for Treatment of Patients with Severe Asthma with Eosinophilic Inflamation; GlaxoSmithKline; FDA Advisory Committee Meeting Briefing Document; pp. 1-101; 2015.
Nijs et al., "Adult-onset Asthma: is it really different?"; European Respiratory Review; vol. 22; No. 127; pp. 44-52, 2013.
Pavord et al., "Mepolizumab for Severe Eosinophilic Asthma (DREAM): a multicenter, double-blind, placebo-controlled trial"; The Lancet; vol. 380, No. 9842; p. 651-659; Aug. 2012 (Abstract Only).
Ortega et al., "Mepolizumab Treatment in Patients with Severe Eosinophilic Asthma", The New England Journal of Medicine, 371;13, pp. 1198-1207, Sep. 2014.
Wenzel, Asthma Phenotypes: The Evolution From Clinical to Molecular Approaches, Nature Medicine, vol. 18, No. 5, May 2012.
Brusselle et al., "Eosinophilic Airway Inflammation in Nonallergic Asthma" Between Bedside and Bench, Nature Medicine, vol. 19, No. 8, pp. 977-979; Aug. 2013.
Miranda et al. "Distinguishing Severe Asthma Phenotypes: Role of Age at Onset and Eosinophilic Inflammation", J Allergy Clin Immunol, pp. 101-108; Jan. 2004.
Teva's Reslizum Delivers Clinically and Statistically Significant Reduction in Asthma Exacebations in Two Pivotal Phase III Studies; Teva Press Release, Sep. 2, 2014.
Lotvall et al., "Asthma Endotypes: A New Approach to Classification of Disease Entities Within the Asthma Syndrome" Journal of Allergy and Clinical Immunology, vol. 127 (2), pp. 355-360, Feb. 2011.
De Nijs et al., "Adult-onset Asthma: is it really Different", European Respiratory Review, vol. 22 No. 127, pp. 44-52, 2013.
De Groot et al., "Management of the Patient With Eosinophilic Asthma: A New Era Begins", ERJ Open Res, Review Asthma, pp. 1-11, May 2015.

* cited by examiner

*Primary Examiner* — Elizabeth C Kemmerer
*Assistant Examiner* — Fozia Hamud
(74) *Attorney, Agent, or Firm* — Baker Hostetler LLP

(57) ABSTRACT

Disclosed herein are methods of treating moderate to severe eosinophilic asthma in a patient comprising administering a therapeutically effective dose of reslizumab to a patient whose symptoms are inadequately controlled with a current asthma therapeutic and wherein the patient's blood eosinophil levels are equal to or greater than 400/µL.

14 Claims, 27 Drawing Sheets

USE OF RESLIZUMAB TO TREAT MODERATE TO SEVERE EOSINOPHILIC ASTHMA

CROSS REFERENCE TO RELATED APPLICATIONS

This application claims priority to U.S. Provisional Application No. 62/047,248, filed Sep. 8, 2014, U.S. Provisional Application No. 62/091,150, filed Dec. 12, 2014, U.S. Provisional Application No. 62/168,007, filed May 29, 2015, and U.S. Provisional Application No. 62/191,690, filed Jul. 13, 2015. The contents of each of these applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 23, 2015, is named 101889.000452_SL.txt and is 6,432 bytes in size.

TECHNICAL FIELD

Disclosed herein are methods of treating moderate to severe eosinophilic asthma. More specifically, provided herein are methods of treating patients that are inadequately controlled with a current asthma therapeutic and who have a blood eosinophil level equal to or greater than 400/μL by administering to said patient a therapeutically effective dose of reslizumab.

BACKGROUND

Asthma is a common, chronic inflammatory condition that affects approximately 12% of adults and 10% of children and adolescents; it is estimated that 300 million people worldwide suffer from this condition. Each day in the United States, approximately 44,000 individuals have asthma attacks, resulting in missed school/work, emergency room visits or admission to a hospital, and even death. Asthma is characterized by inflammation, and narrowing, of the air passages leading to wheezing, chest tightness, shortness of breath, and coughing.

Common medications for the treatment of asthma include inhaled corticosteroids and/or long acting $\beta_2$-agonists. These medications, however, may inadequately control the patient's asthma symptoms. Patients with inadequately controlled severe persistent asthma are at risk of exacerbations, hospitalization and death, and often have impaired quality of life. Thus, new therapeutics are needed to treat patients whose asthma is inadequately controlled. The enclosed methods address these and other important needs.

SUMMARY

Disclosed herein are methods of treating moderate to severe eosinophilic asthma in a patient comprising: 1) identifying a patient having moderate to severe eosinophilic asthma, wherein the patient's symptoms are inadequately controlled with a current asthma therapeutic and wherein the patient's blood eosinophil levels are equal to or greater than 400/μL; and 2) administering to said patient a therapeutically effective dose of reslizumab.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods disclosed. In the drawings.

Figure 7A:
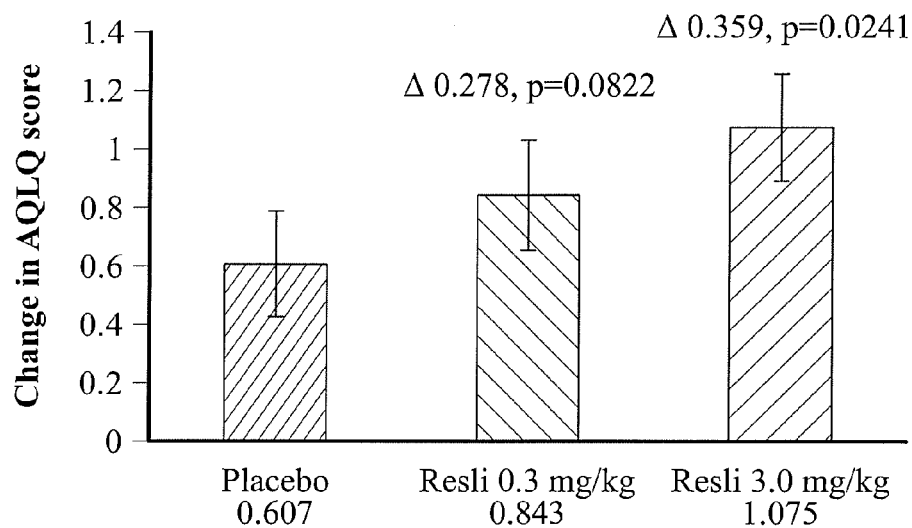
Figure 7B:
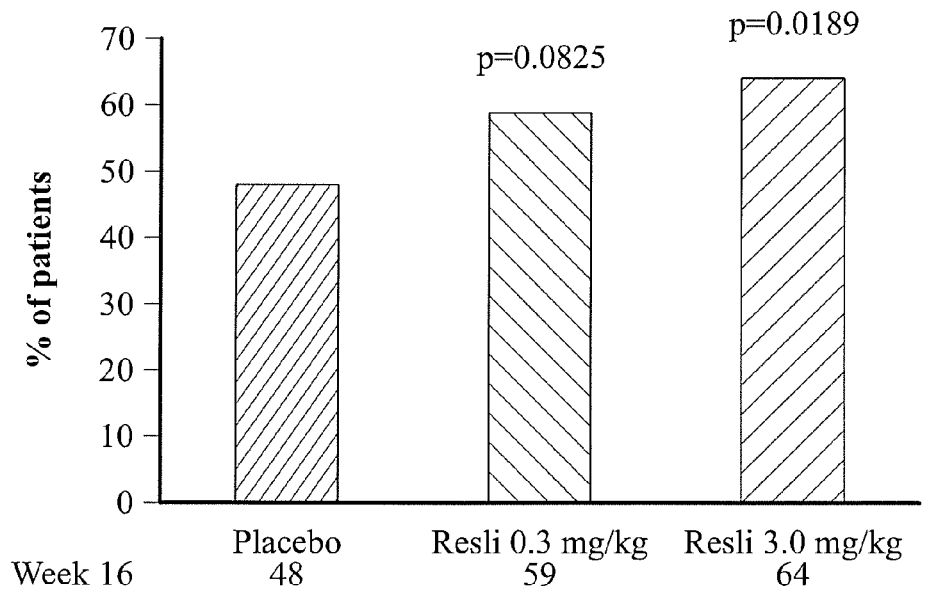

FIG. 7A and FIG. 7B represent the change from baseline to week 16 in asthma quality of life questionnaire (AQLQ) score (FIG. 7A) and the proportion of patients achieving at least 0.5 improvement from baseline to week 16 in AQLQ (FIG. 7B) by treatment group in study 1. AQLQ was only assessed at baseline and at week 16. The minimally clinical important difference for AQLQ is 0.5 units. Data are least-squared means±standard error.

Figure 8A:
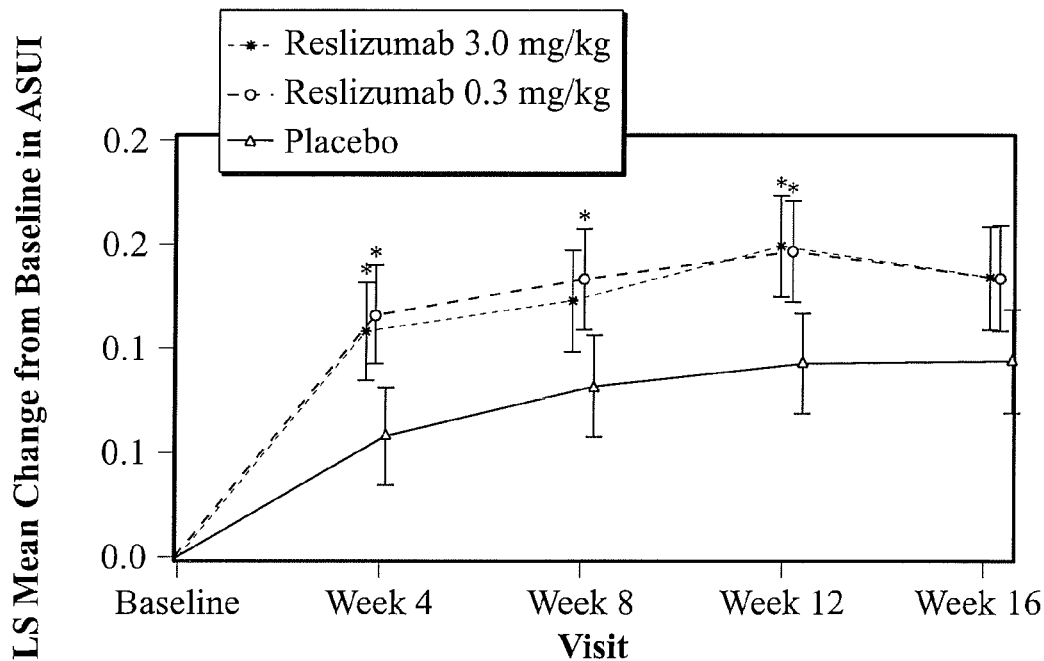
Figure 8B:
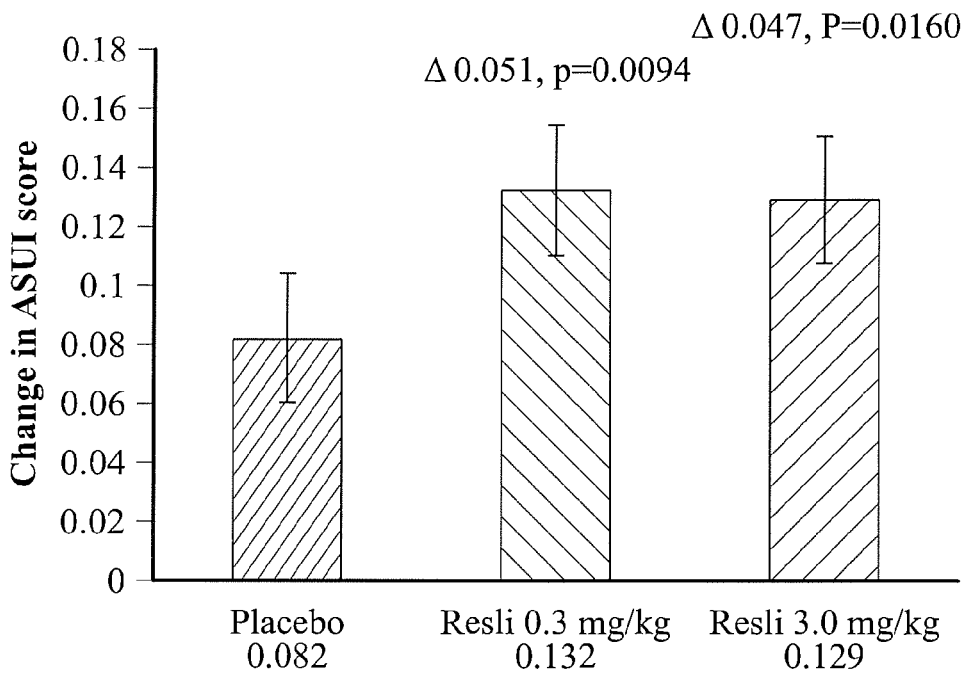

FIG. 8A and FIG. 8B represent the change (SE) from baseline to each visit in asthma symptom utility index (AUSI) score (FIG. 8A) and the overall change from baseline over 16 weeks of treatment in ASUI (FIG. 8B) by treatment group in study 1. SE=standard error; LS=Least Squares. * p≤0.05, ** p≤0.005 versus placebo. P values are not adjusted to control for multiplicity. Placebo=solid line; reslizumab 0.3 mg/kg=shorter hashes; reslizumab 3.0 mg/kg=longer hashes.

Figure 9A:
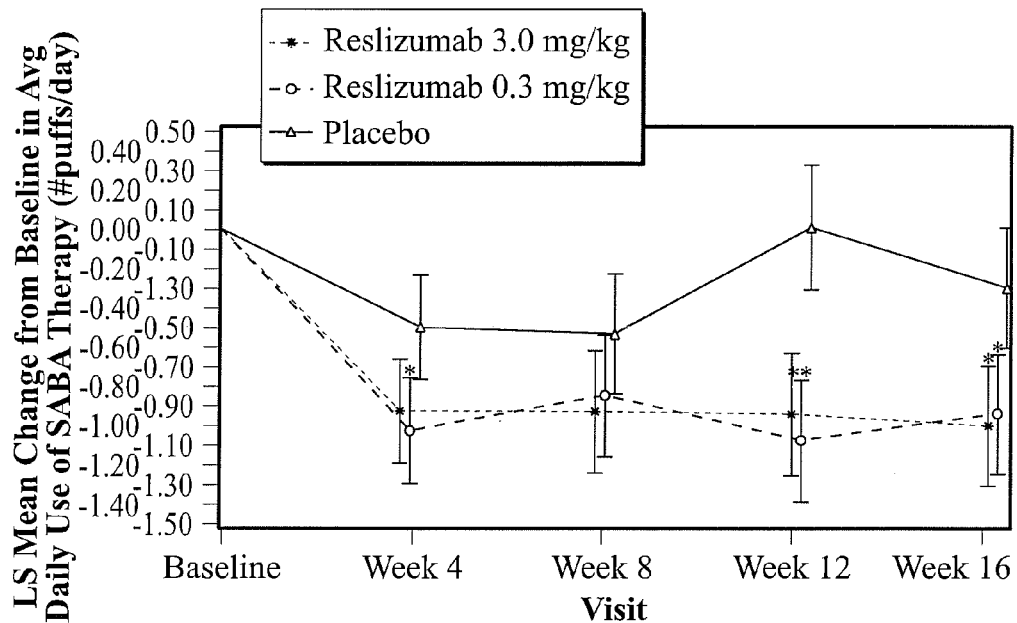
Figure 9B:
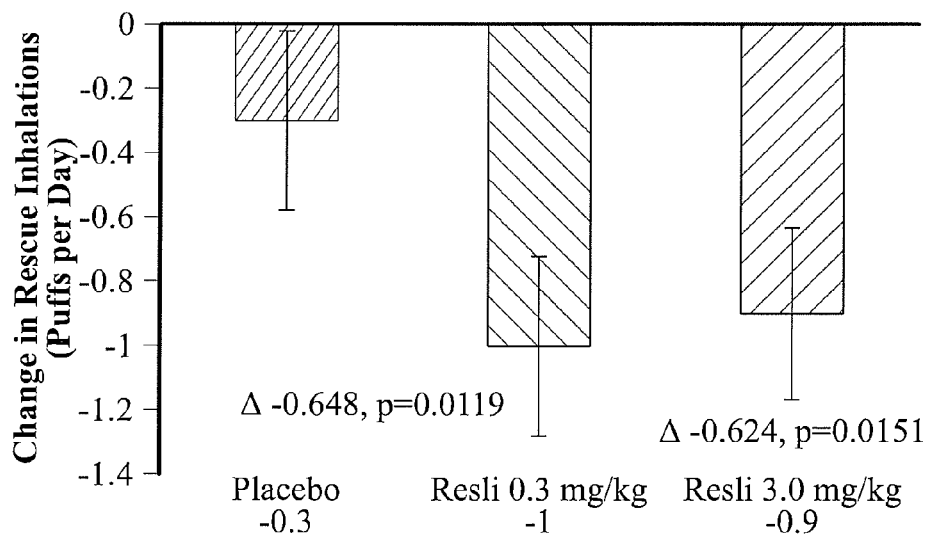

FIG. 9A and FIG. 9B represent the change (SE) from baseline to each visit in short acting beta agonist (SABA) use by visit and treatment group (FIG. 9A) and the change from baseline in average daily use of SABA by treatment group (FIG. 9B) in study 1. SE=standard error; LS=Least Squares. * p≤0.05, ** p≤0.005. P values are not adjusted to control for multiplicity. Placebo=solid line; reslizumab 0.3 mg/kg=shorter hashes; reslizumab 3.0 mg/kg=longer hashes.

Figure 10A:
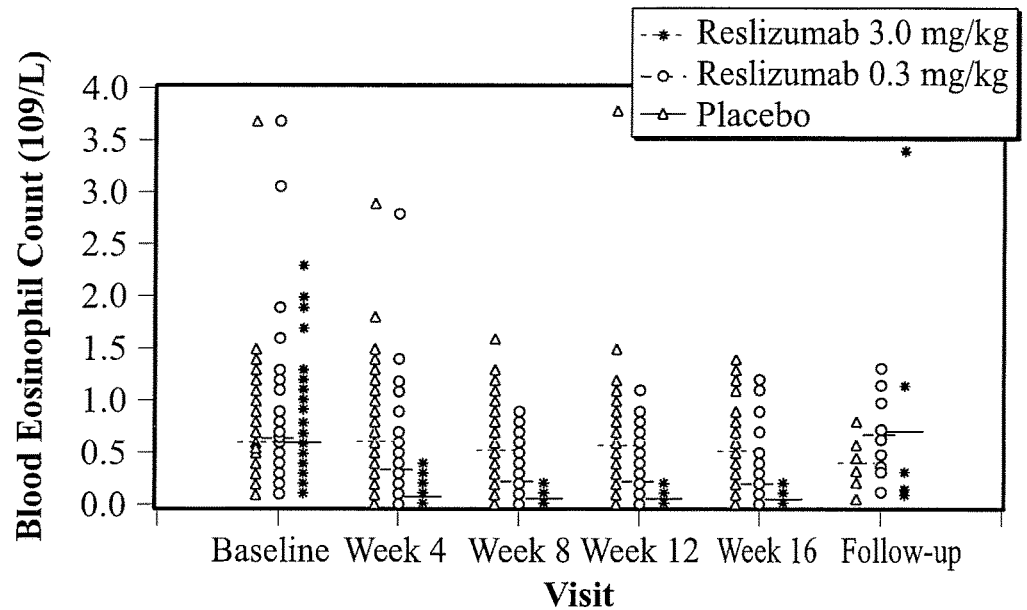
Figure 10B:
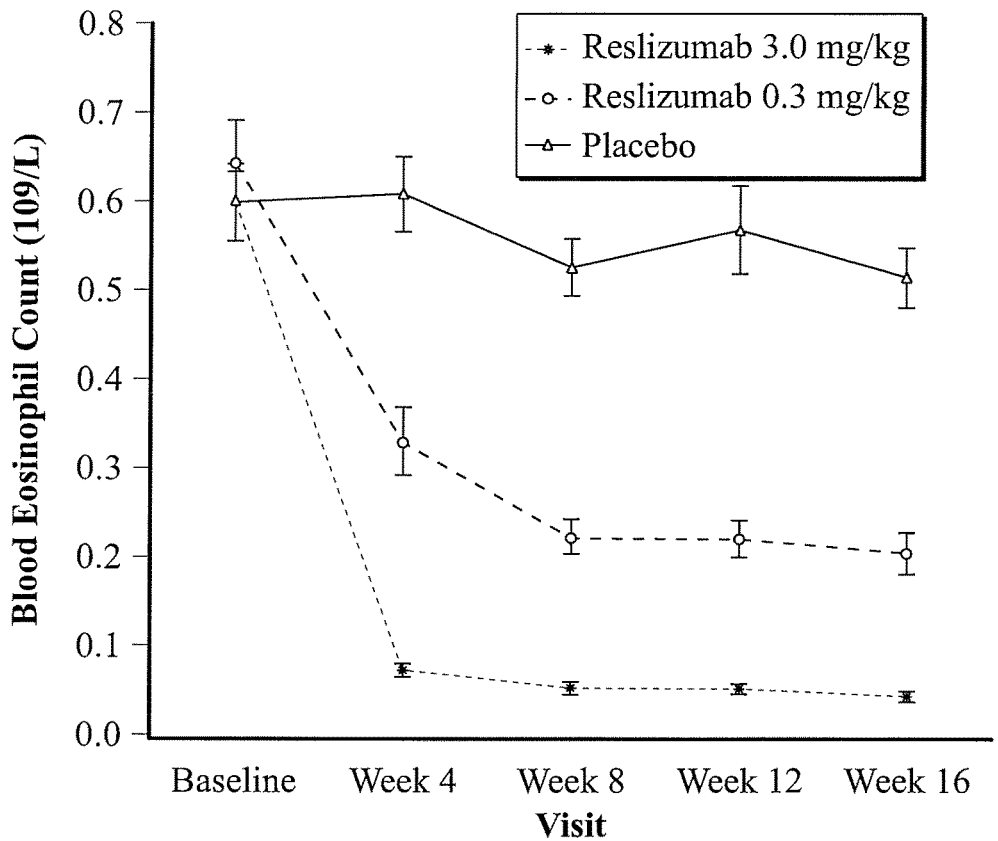

FIG. 10A and FIG. 10B represent the blood eosinophil counts over time by treatment group in study 1. The blood eosinophil counts were measured using a standard CBC with differential blood test at each scheduled visit. FIG. 10A) Placebo=left data set in each group; reslizumab 0.3 mg/kg=middle data set in each group; reslizumab 3.0 mg/kg=right data set in each group. FIG. 10B) Placebo=solid line; reslizumab 0.3 mg/kg=shorter hashes; reslizumab 3.0 mg/kg=longer hashes.

Figure 11A:
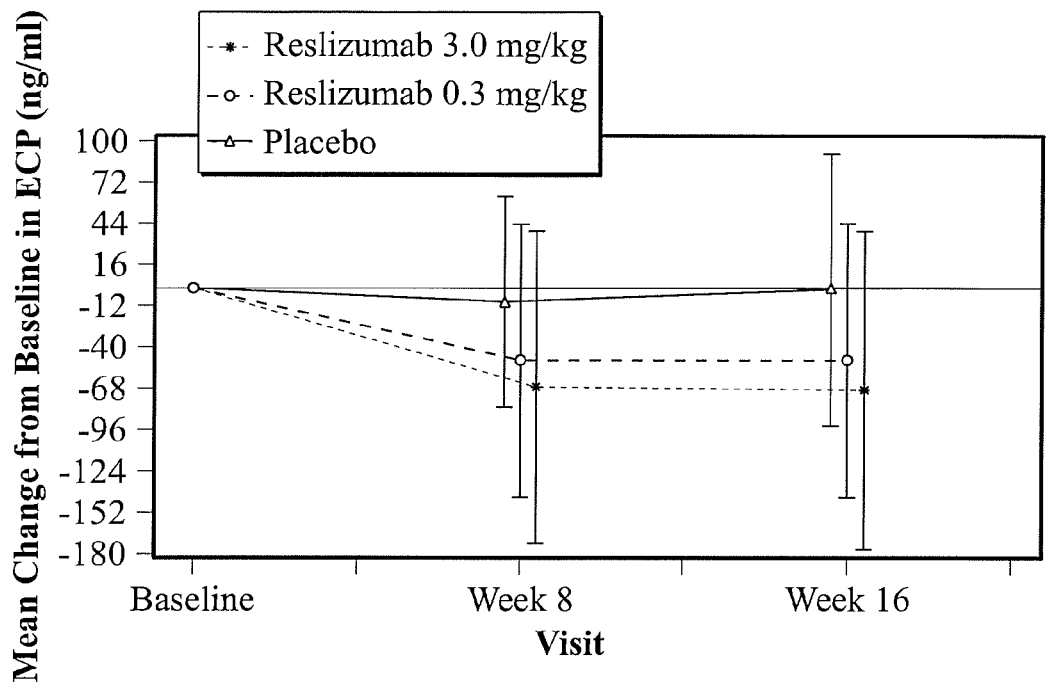
Figure 11B:
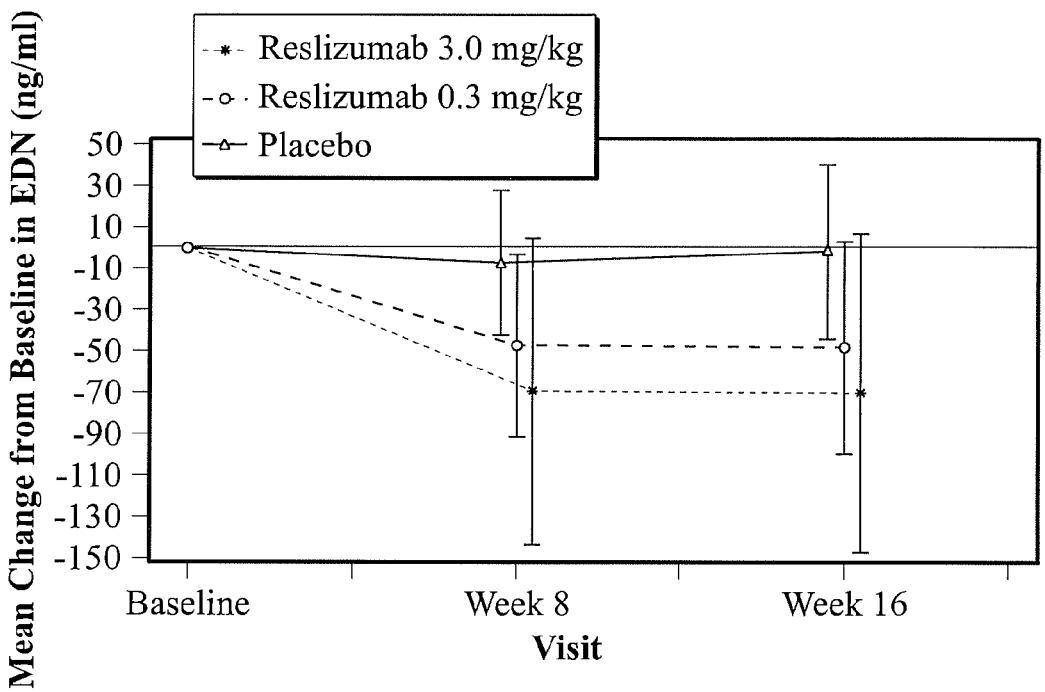

FIG. 11A and FIG. 11B represent the mean change from baseline (+/−SD) in serum ECP at Week 8 and 16 (FIG. 11A) and Serum EDN at Week 8 and 16 (FIG. 11B) in study 1. Placebo=solid line; reslizumab 0.3 mg/kg=shorter hashes; reslizumab 3.0 mg/kg=longer hashes.

Figure 12A:
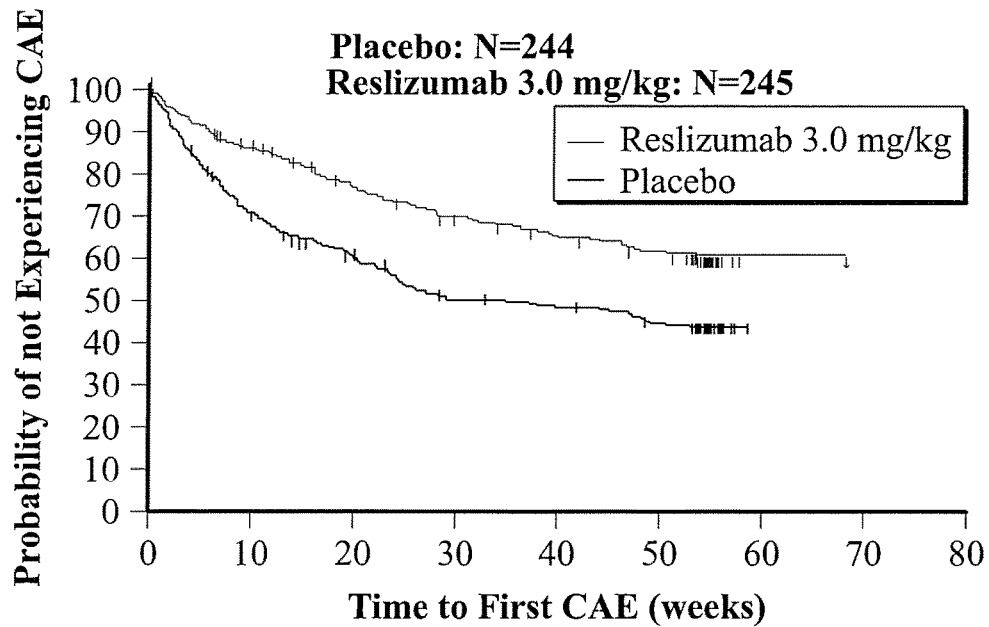
Figure 12B:
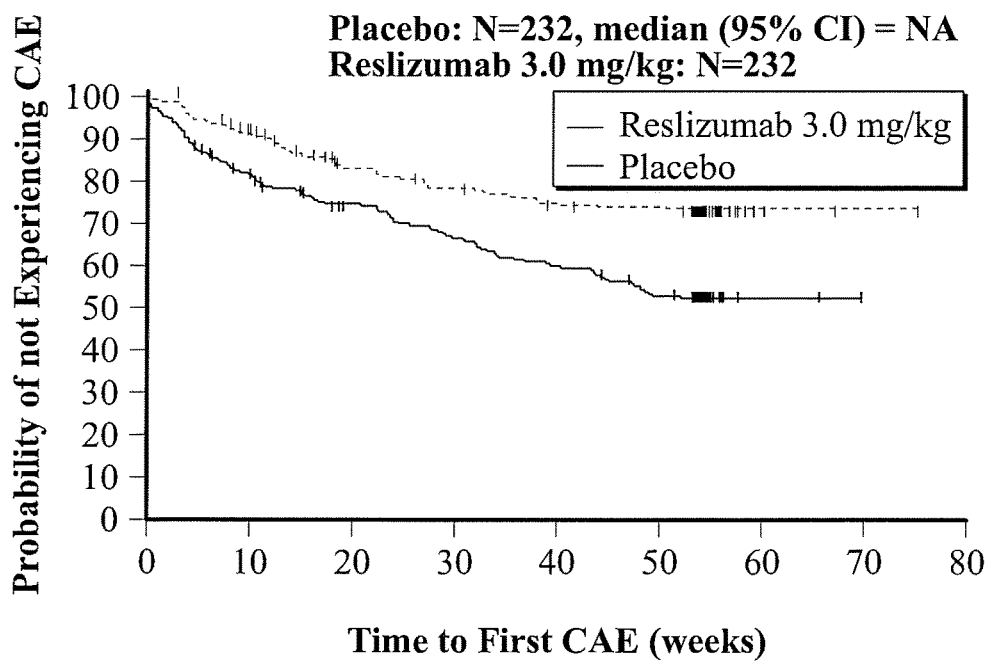
Figure 12C:
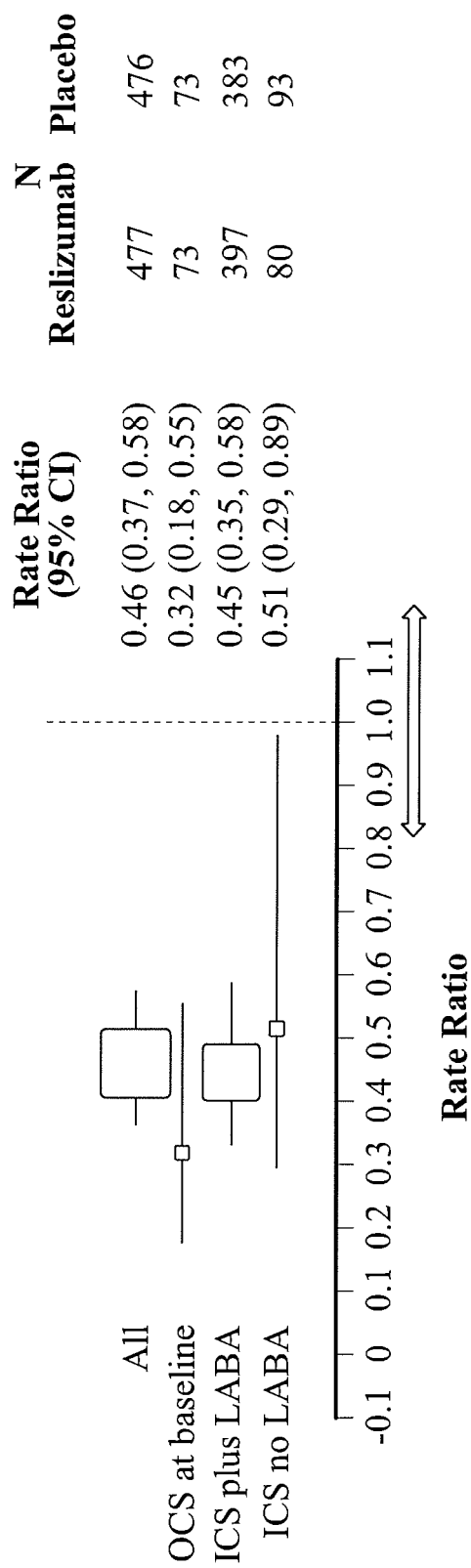

FIG. 12A, FIG. 12B and FIG. 12C represent the time to First Clinical Asthma Exacerbation in (FIG. 12A) Study 2 and (FIG. 12B) Study 3 plus pooled analyses (studies 2 and 3) of CAE rate ratios (FIG. 12C). FIG. 12A and FIG. 12B show the time to first CAE against the probability of not experiencing an exacerbation. Median (95% CI) times to first CAE are presented. FIG. 12C presents the CAE rate-ratios for pooled populations Study 2 plus Study 3 according to major background therapy. *P≤0.05, P≤0.01, *P≤0.001. CI, confidence interval; NA, not available. In FIG. 12A and FIG. 12B placebo=top line; reslizumab 3.0 mg/kg=bottom line.

Figure 13A:
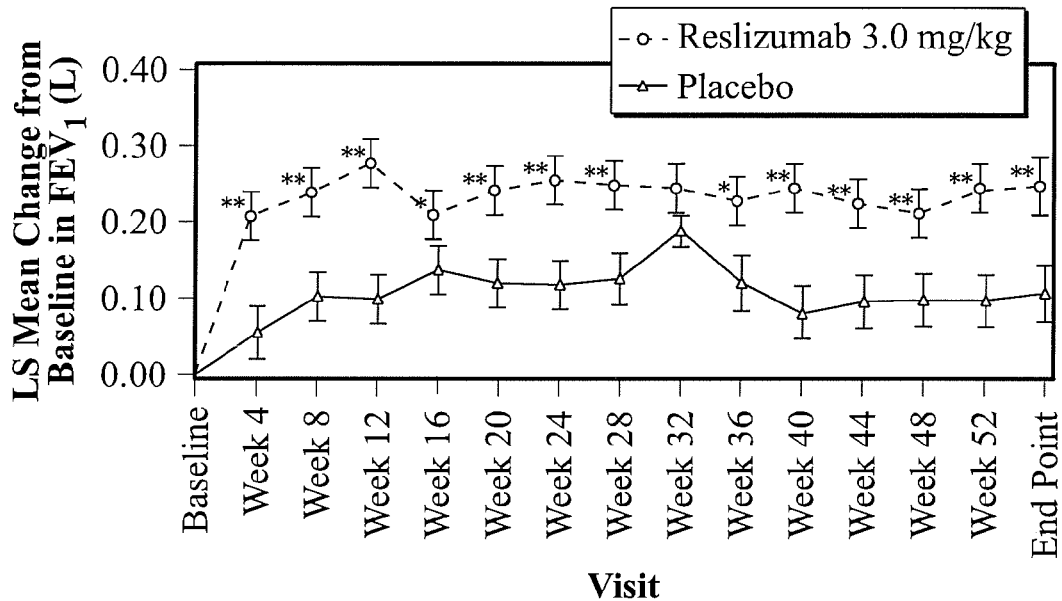
Figure 13B:
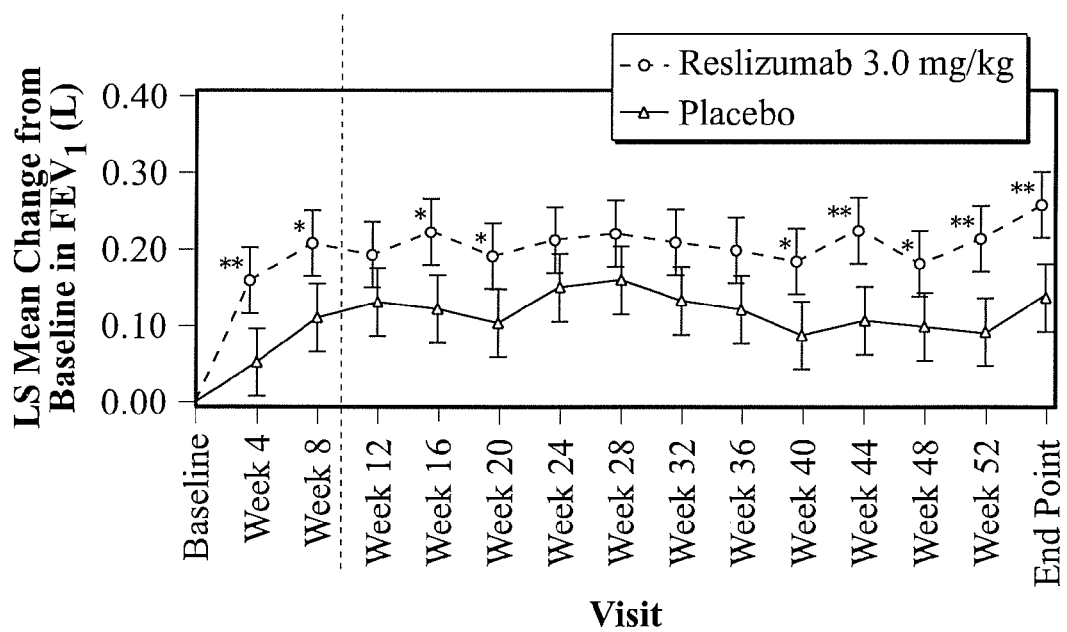
Figure 13C:
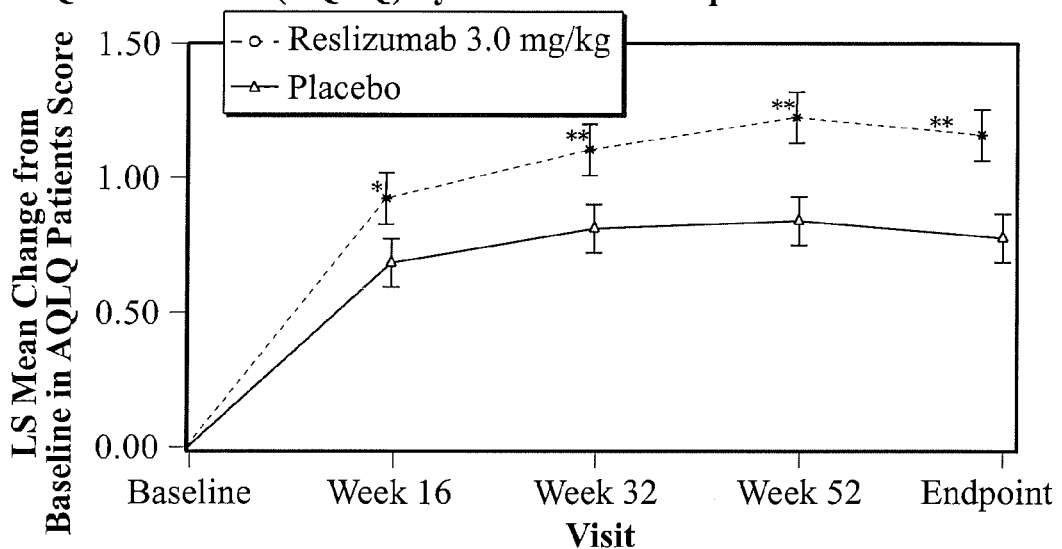
Figure 13D:
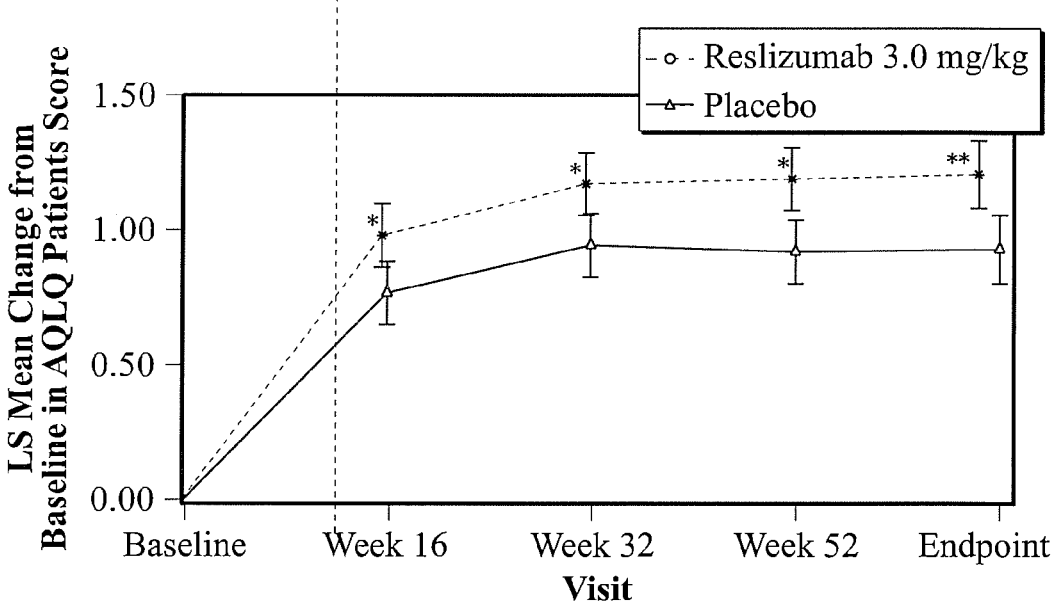

FIG. 13A, FIG. 13B, FIG. 13C, and FIG. 13D represent changes in $FEV_1$ and AQLQ over 52 weeks for Study 2 (FIG. 13A and FIG. 13C respectively) and Study 3 (FIG. 13B and FIG. 13D respectively). The secondary efficacy—$FEV_1$ over time—from study 2 (FIG. 13A) and study 3 (FIG. 13B), comparing the LS mean change from baseline in $FEV_1$ at baseline and for each visit. Changes in key lung function parameters throughout the 52-Week study. In both studies $FEV_1$ improved by Week 4 and was maintained until study end. Quality of life was improved at the first measured time point (Week 16) and was maintained until Week 52. In each of FIG. 13A-FIG. 13D, placebo=solid, bottom line; reslizumab=hashed, top line.

Figure 14A:
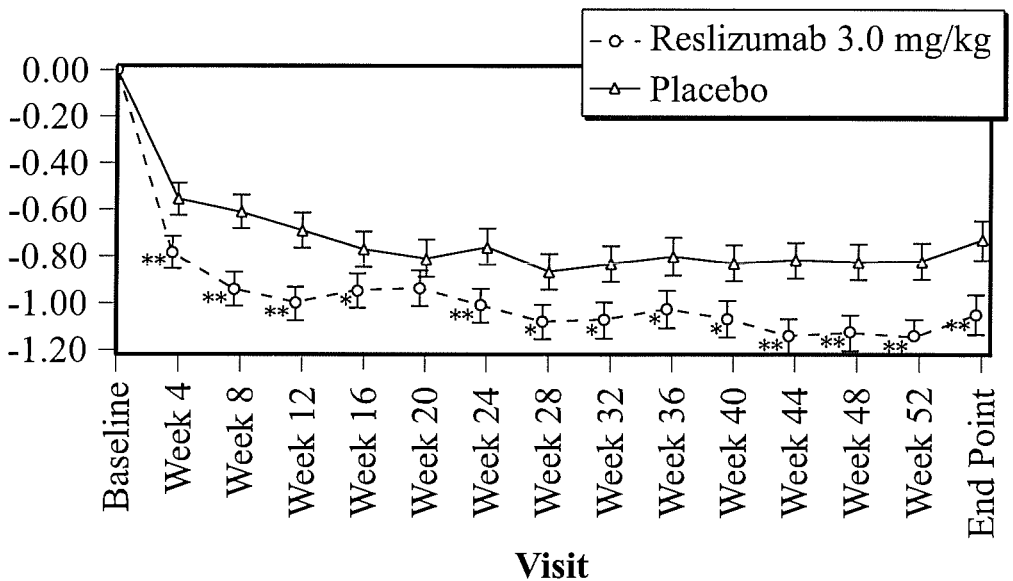
Figure 14B:
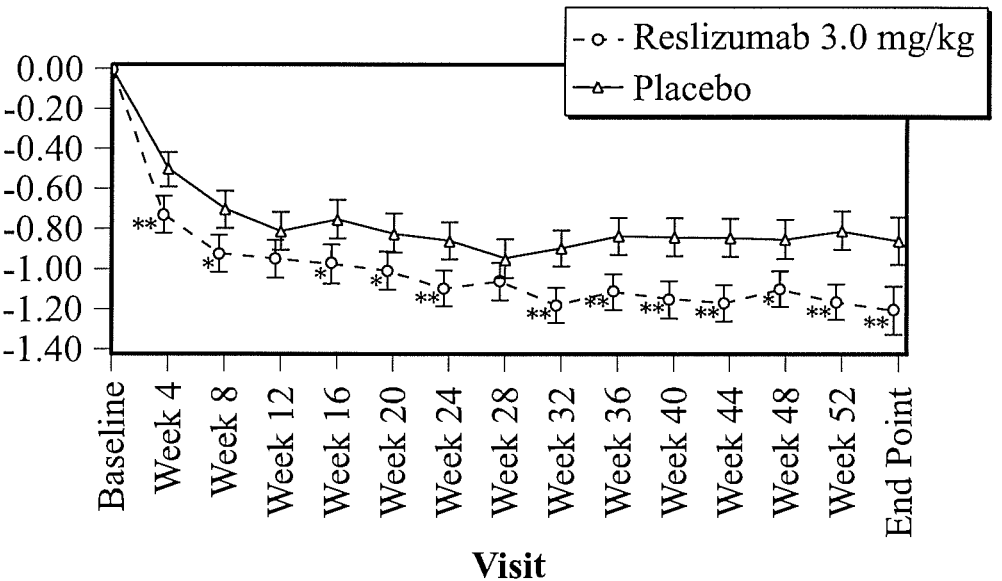

FIG. 14A and FIG. 14B represent the change from Baseline in Asthma Control Questionnaire Score over the 52-Week Treatment Period in (FIG. 14A) Study 2 and (FIG. 14B) Study 3 (Intention-to-Treat Population). The panels show the least-square mean (standard error) change from baseline in Asthma Control Questionnaire score over the 52-week study period and at end-of-treatment. *P≤0.05, P≤0.01, *P≤0.001. In each of FIG. 14A-FIG. 14B, placebo=solid, top line; reslizumab=hashed, bottom line.

Figure 15A:
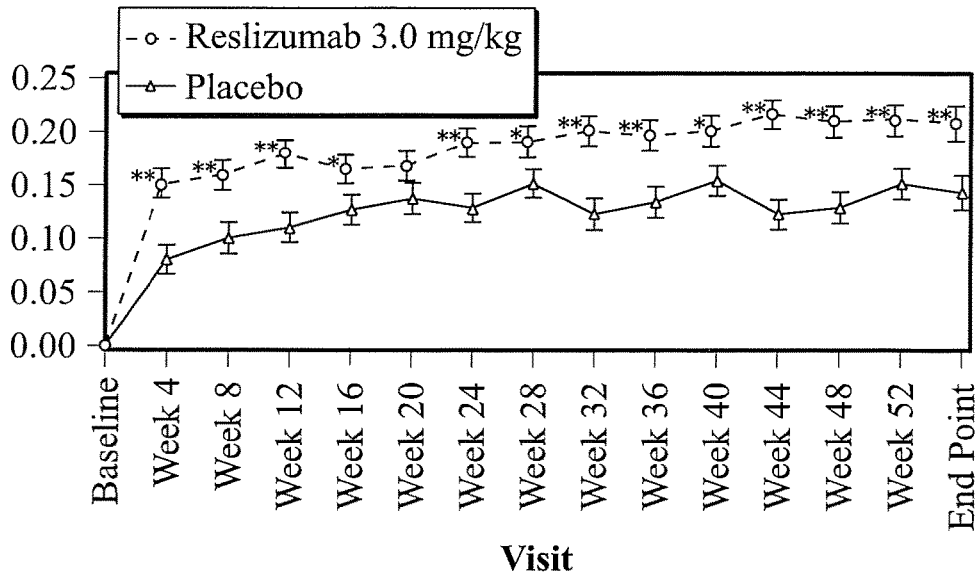
Figure 15B:
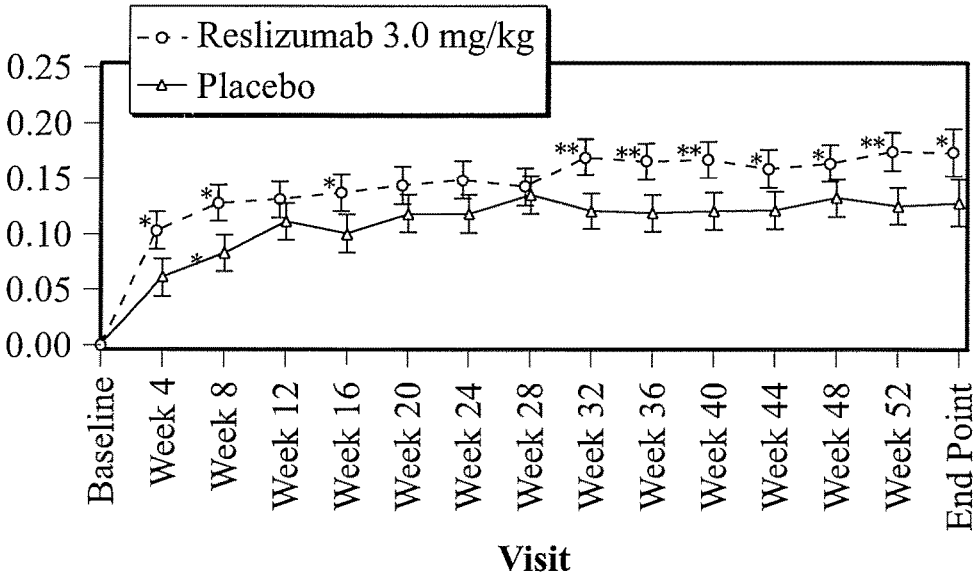

FIG. 15A and FIG. 15B represent the change from Baseline in Asthma Symptom Utility Index Score over the 52-Week Treatment Period in (FIG. 15A) Study 2 and (FIG. 15B) Study 3 (Intention-to-Treat Population). The panels show the least-square mean (standard error) change from baseline in Asthma Symptom Utility Index score over the 52-week study period and at end-of-treatment. *P≤0.05, P≤0.01, *P≤0.001. In each of FIG. 15A-FIG. 15B, placebo=solid, bottom line; reslizumab=hashed, top line.

Figure 16A:
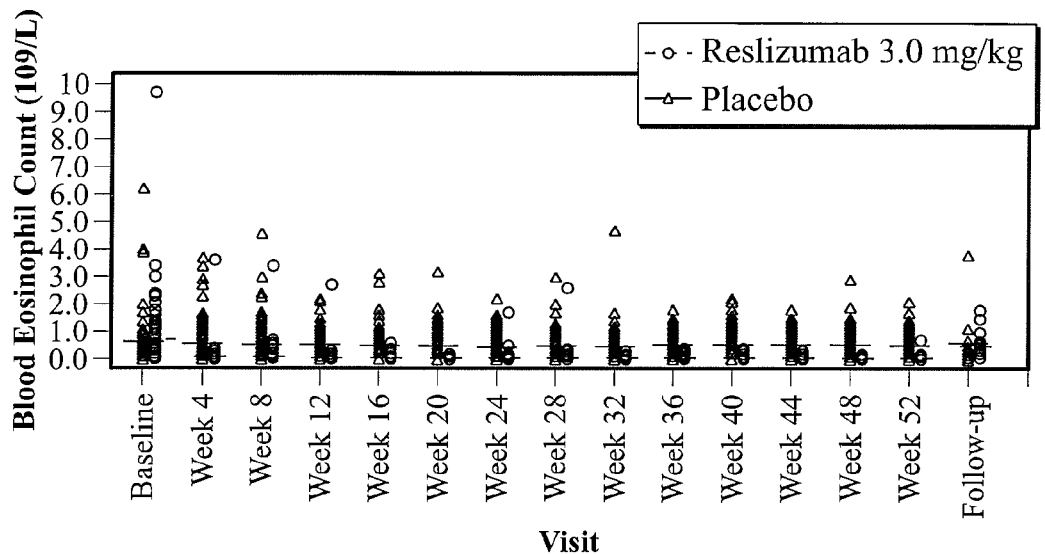
Figure 16B:
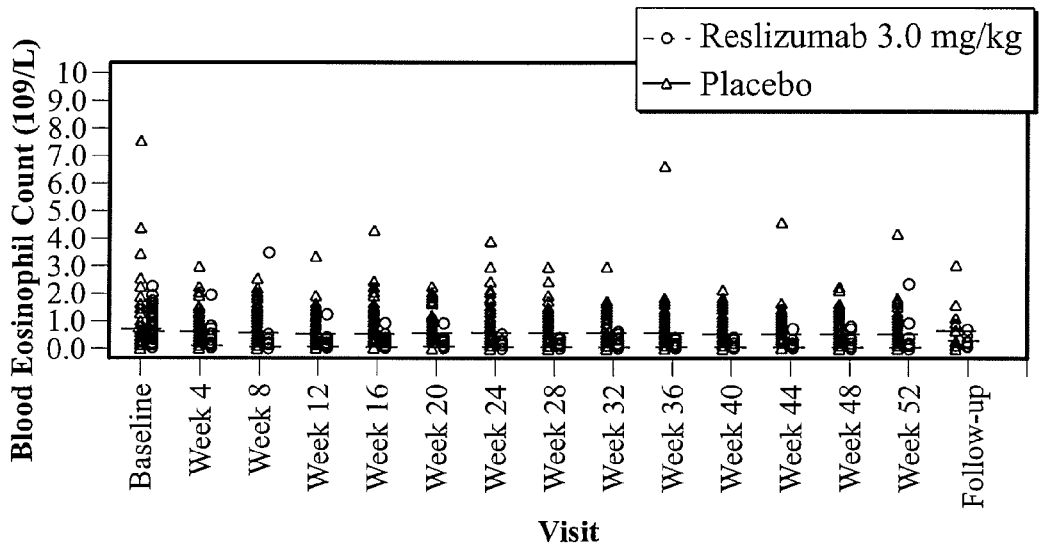

FIG. 16A and FIG. 16B represent scatter Plot of Blood Eosinophil Count over the 52-Week Treatment Period in (FIG. 16A) Study 2 and (FIG. 16B) Study 3 (Intention-to-Treat Population). The panels show individual blood eosinophil counts in both treatment arms over the 52-week study period and treatment follow-up. Patients were required to have a blood eosinophil count of at least 400/μL at least once during the screening period prior to being randomized. As this value did not necessarily occur at baseline, the baseline eosinophil counts depicted for the randomized population in the figure include some patients with values below 400/μL. In each of FIG. 16A-FIG. 16B, placebo=left data points in each group; reslizumab=right data points in each group.

Figure 17:
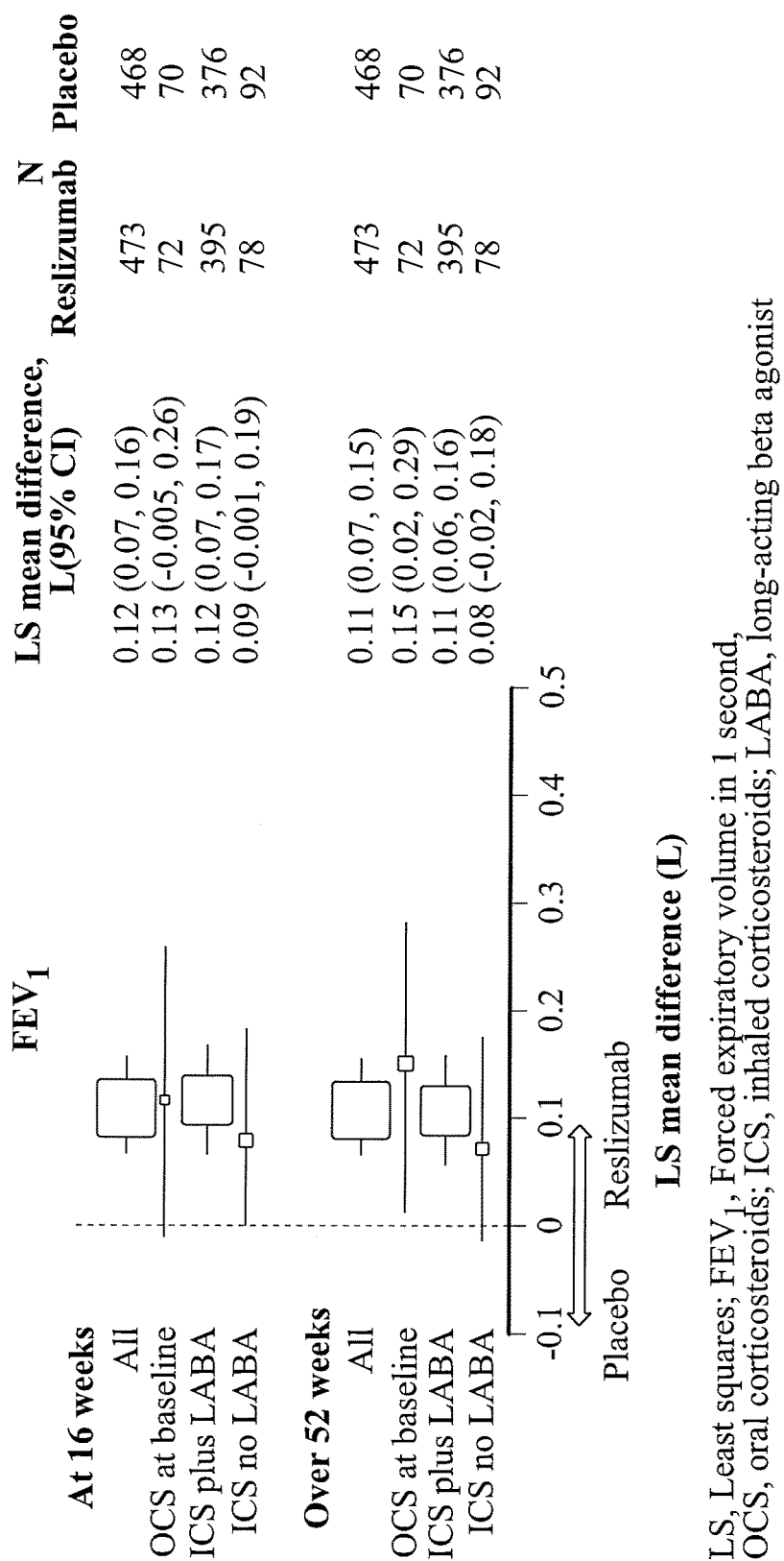

FIG. 17 represents a pooled sub-analyses of $FEV_1$ least-squares means at over the first 16 weeks and from baseline to study end (week 52) for patient populations with different concomitant medication profiles.

Figure 18A:
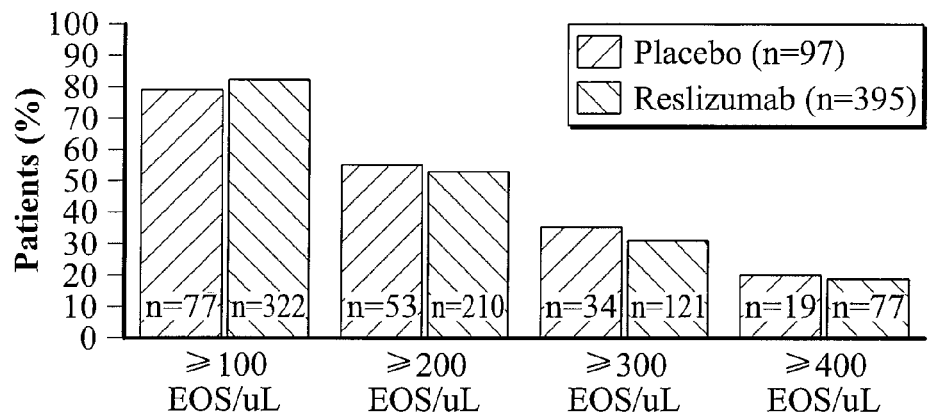
Figure 18B:
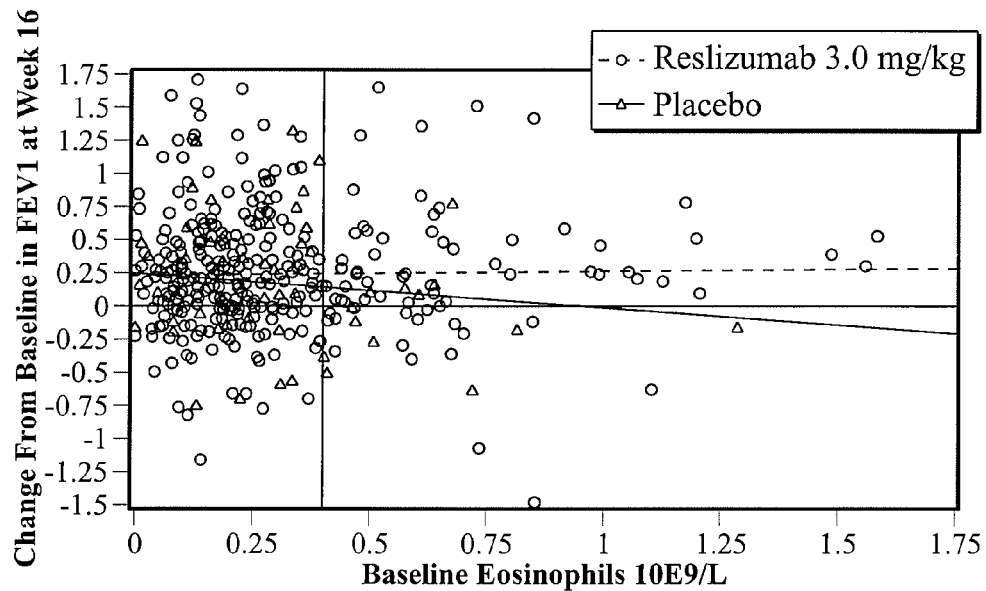
Figure 18C:
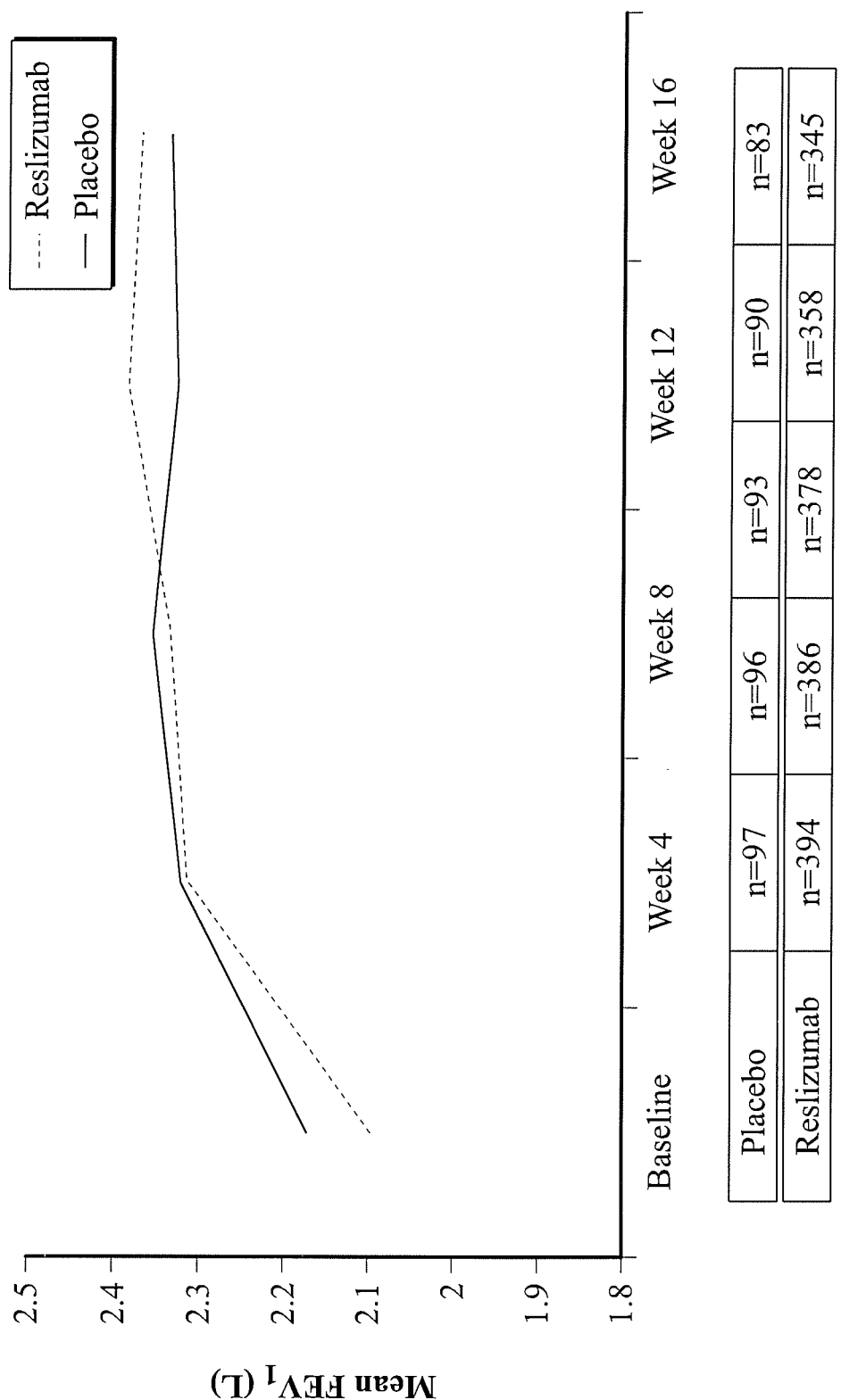
Figure 18D:
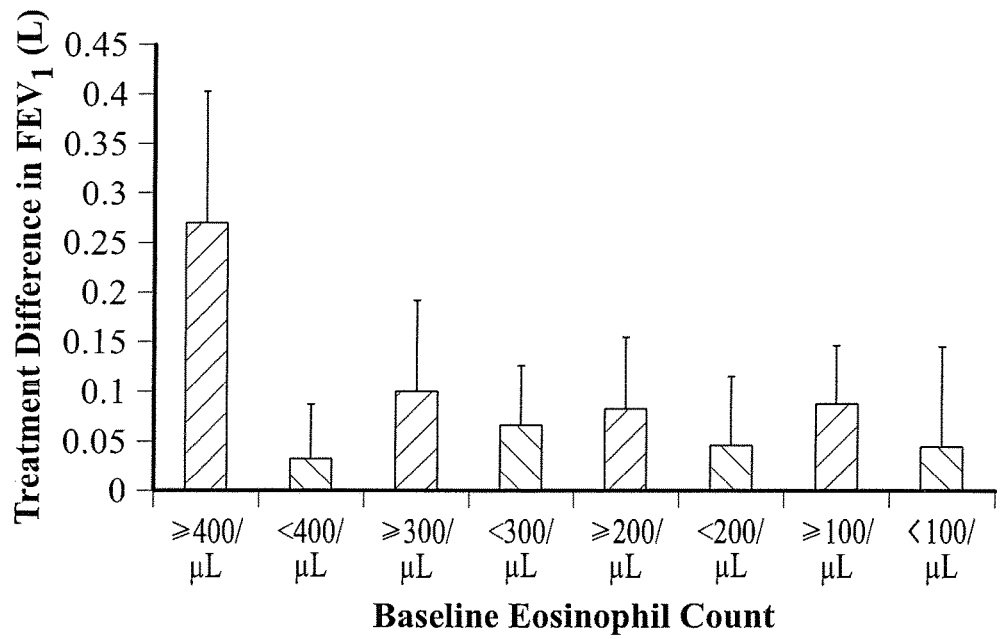
Figure 18E:
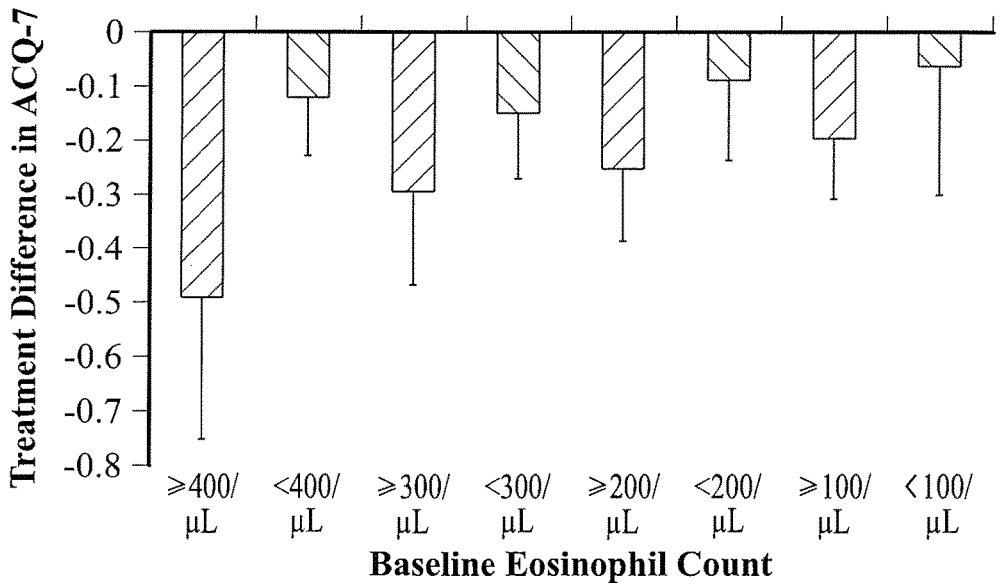
Figure 18F:
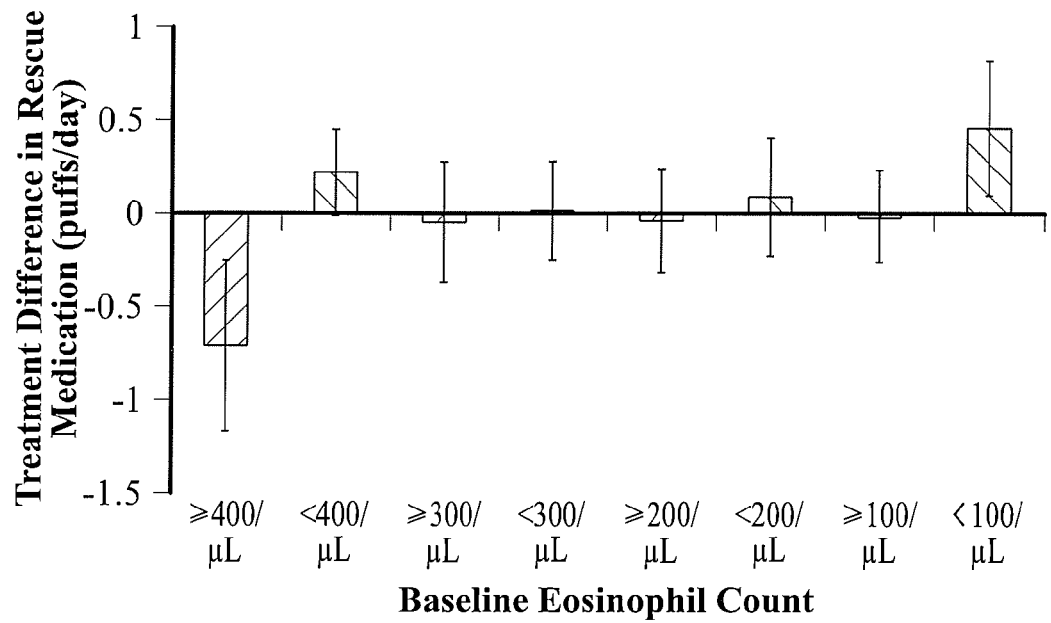
Figure 18G:
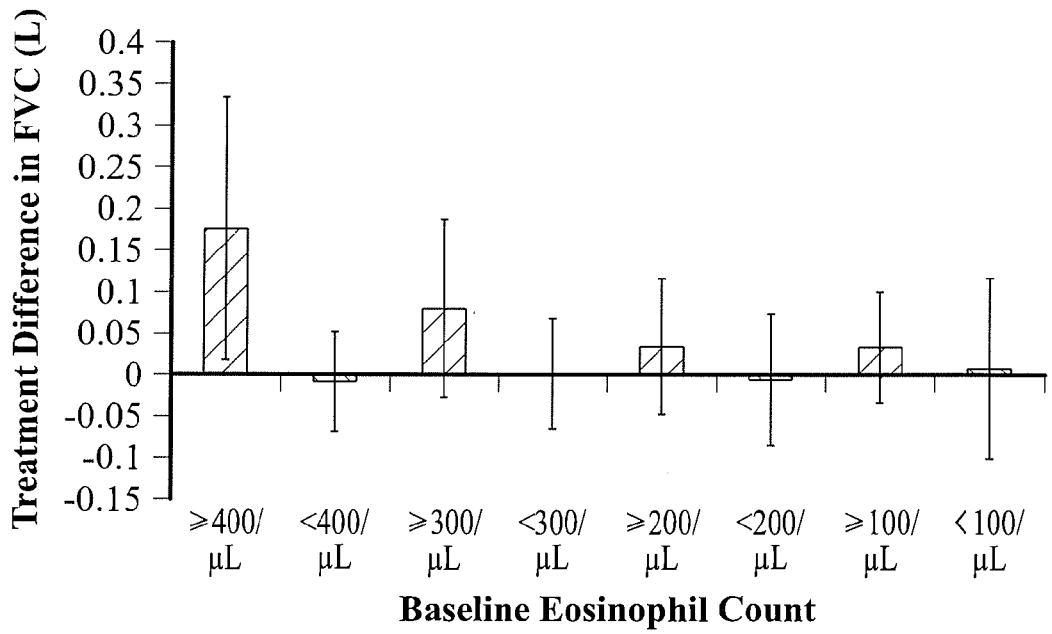

FIG. 18A, FIG. 18B, FIG. 18C, FIG. 18D, FIG. 18E, FIG. 18F, and FIG. 18G represent the baseline blood eosinophil category (FIG. 18A), the change in $FEV_1$ (week 16) vs. baseline eosinophils: linear regression model (FIG. 18B); the mean $FEV_1$ over time by treatment: overall population (FIG. 18C) (error bars are standard error of mean); reslizumab treatment effect by baseline eosinophil count at week 16: $FEV_1$ (FIG. 18D) (*P=0.0436; Error bars are standard error of the difference between reslizumab and placebo; Treatment difference, corresponding SE, and P value are from MMRM); the reslizumab treatment effect by baseline eosinophil count at week 16: ACQ-7 (FIG. 18E) (Error bars are standard error of the difference between reslizumab and placebo; Treatment difference and corresponding SE are from MMRM); the reslizumab treatment effect by baseline eosinophil count at week 16: rescue medication (FIG. 18F) (Error bars are standard error of the difference between reslizumab and placebo; Treatment difference and corresponding SE are from MMRM); and the reslizumab treatment effect by baseline eosinophil count at week 16: FVC (FIG. 18G) (Error bars are standard error of the difference between reslizumab and placebo; Treatment difference and corresponding SE are from MMRM). In FIG. 18A) placebo=left bar in each group; reslizumab=right bar in each group. In FIG. 18B) placebo=triangles; reslizumab=circles.

Figure 19A:
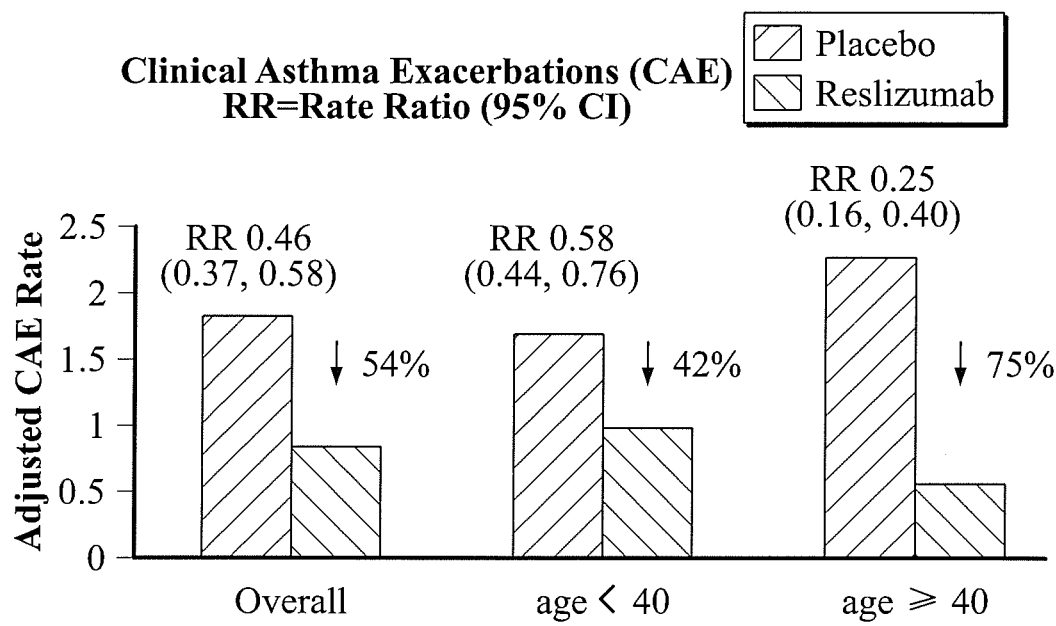
Figure 19B:
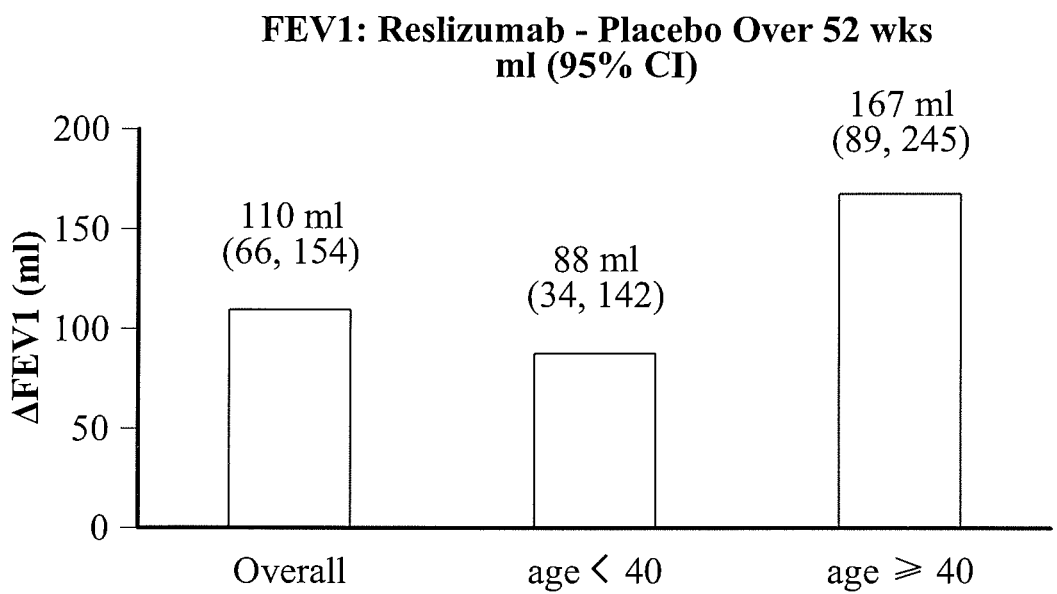

FIG. 19A and FIG. 19B represents (FIG. 19A) annual rate of asthma exacerbations (clinical asthma exacerbations: CAE) and (FIG. 19B) overall change in lung function ($FEV_1$) in the overall patient population, patients not having late-onset asthma (less than 40 years old at time of diagnosis "age <40") and patients having late-onset asthma (greater than or equal to 40 years old at time of diagnosis "age ≥40").

Figure 20A:
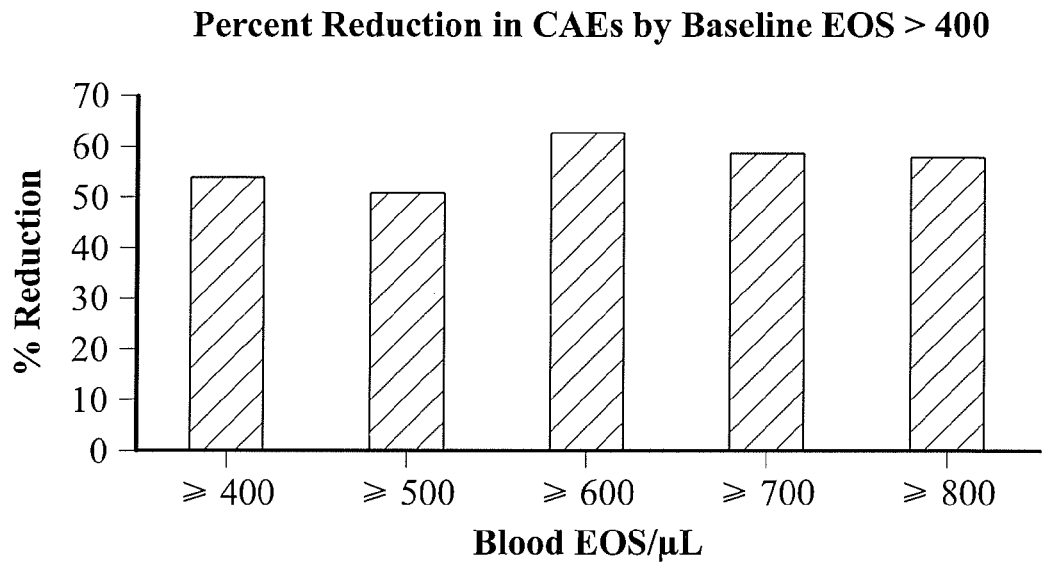
Figure 20B:
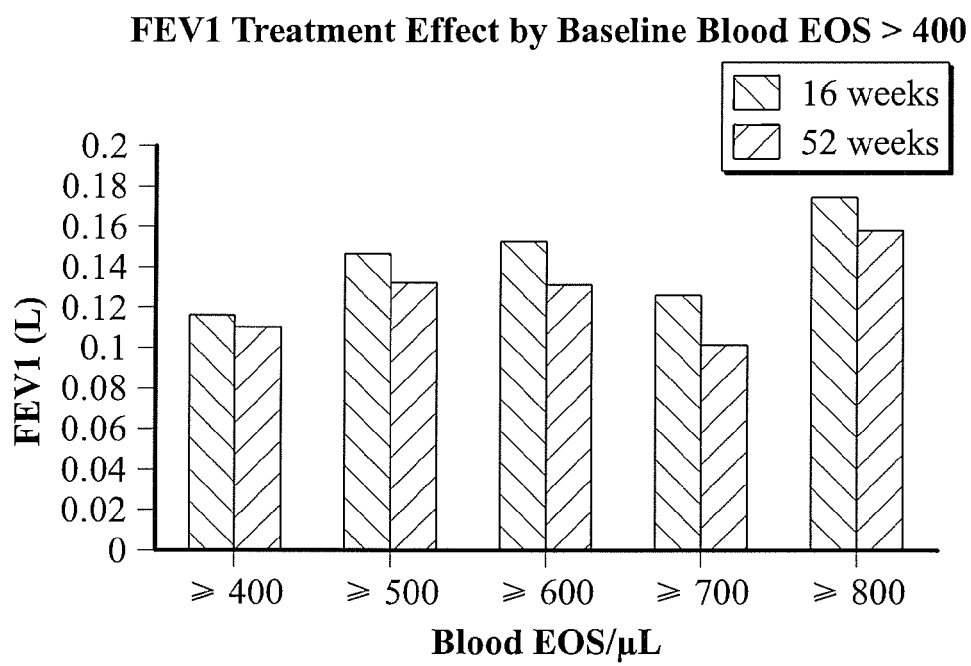

FIG. 20A and FIG. 20B represents the influence of baseline eosinophil counts higher than a 400/μl cut-off, in pooled 52 week exacerbation studies, on (FIG. 20A) percent reduction in CAEs and (FIG. 20B) $FEV_1$. In B), 16 weeks=left bar in each group; 52 weeks=right bar in each group.

Figure 21A:
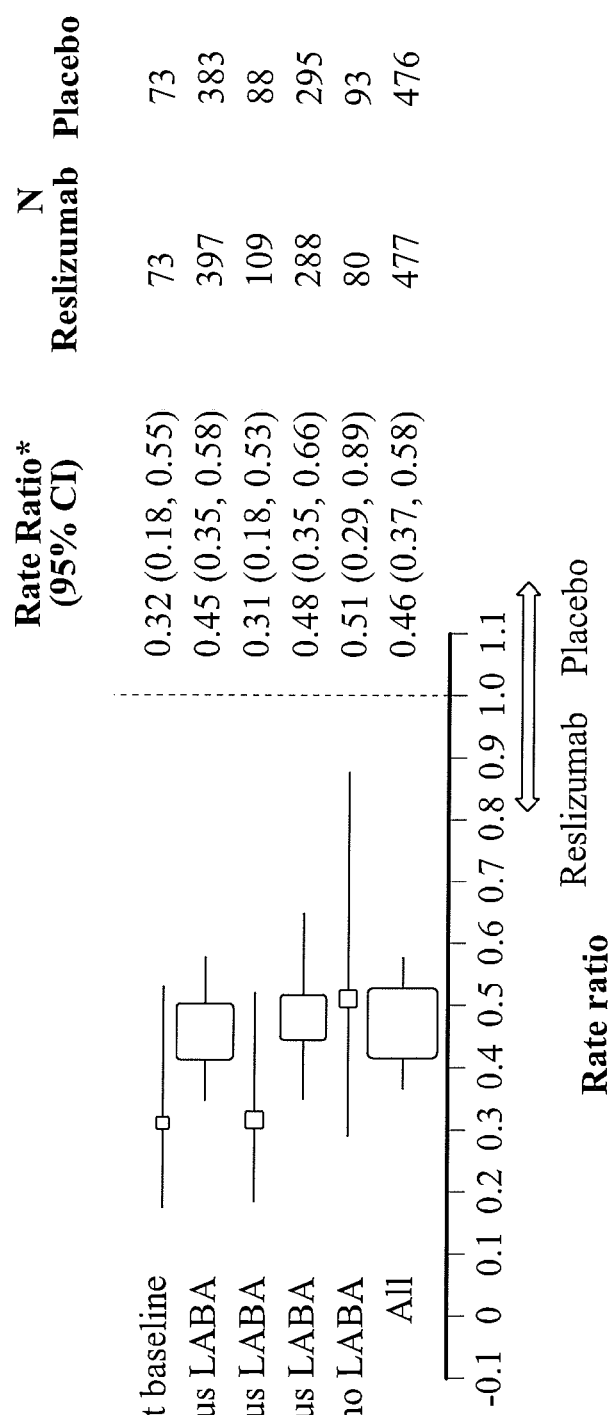
Figure 21B:
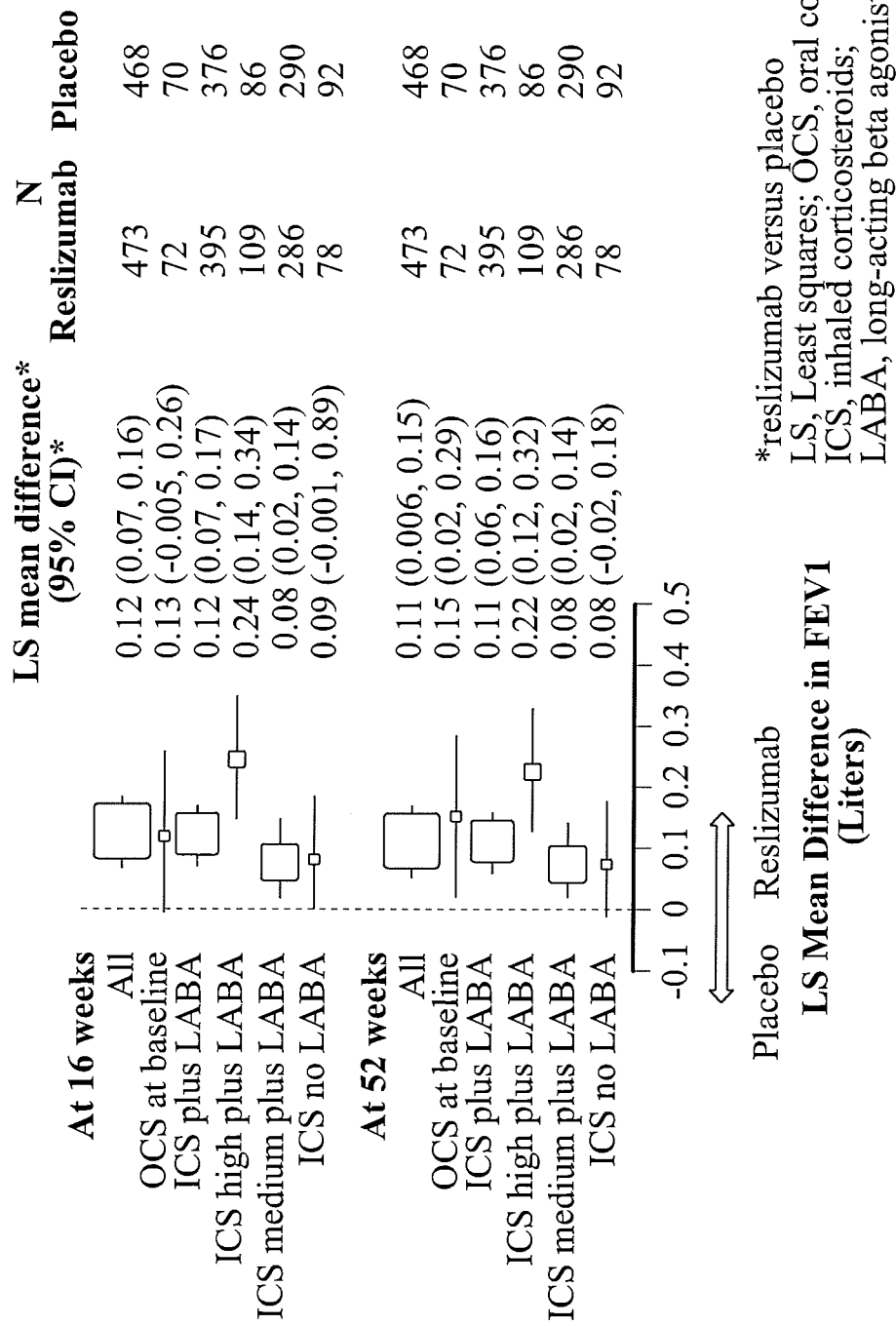

FIG. 21A and FIG. 21B illustrates the influence of disease severity (based on background controller medication) on reslizumab efficacy on (FIG. 21A) CAE (clinical asthma exacerbation) and (FIG. 21B) $FEV_1$. Pooled results (across studies 2 and 3) for CAE rate ratios by level of asthma therapy at entry. The background medication requirement for reslizumab was at least medium dose ICS (≥440 μg fluticasone or equivalent)±another controller. The majority of patients were using a LABA. *reslizumab relative to placebo, CAE (clinical asthma exacerbations), OCS (oral corticosteroids), ICS (inhaled corticosteroids), LABA (long-acting beta agonist), LS (least squares).

In the above figures and the results that follow herein, all inferential statistics are derived from mixed model repeated measures (MMRM) with treatment, visit, treatment by visit interaction, age group, history of asthma exacerbation in the previous 12 months, height, baseline, sex, and patient as a random effect.

DETAILED DESCRIPTION OF ILLUSTRATIVE EMBODIMENTS

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Similarly, unless specifically otherwise stated, any description as to a possible mechanism or mode of action or reason for improvement is meant to be illustrative only, and the disclosed methods are not to be constrained by the correctness or incorrectness of any such suggested mechanism or mode of action or reason for improvement.

When a range of values is expressed, another embodiment includes from the one particular value and/or to the other particular value. Further, reference to values stated in ranges include each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

The following abbreviations are used throughout the disclosure: ACQ (Asthma Control Questionnaire); AQLQ (Asthma Quality of Life Questionnaire); ASUI (Asthma Symptom Utility Index); CAE (clinical asthma exacerbation); $FEV_1$ (forced expiratory volume in 1 second); FVC (forced vital capacity); Forced Expiratory Flow Rate ($FEF_{25\%-75\%}$); ICS (inhaled corticosteroid); LABA (long-acting beta-agonist); SABA (short-acting beta-agonist); AE (adverse event).

The term "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

As used herein, "treating" and like terms refer to a reducing the severity and/or frequency of asthma symptoms, eliminating asthma symptoms and/or the underlying cause of said symptoms, reducing the frequency or likelihood of asthma symptoms and/or their underlying cause, and improving or remediating damage caused, directly or indirectly, by asthma.

As used herein, "administering to said patient" and similar terms indicate a procedure by which reslizumab is injected into a patient such that target cells, tissues, or segments of the body of the subject are contacted with reslizumab.

As used herein, "injected" includes intravenous (iv) or subcutaneous (sub-Q) administration. In some embodiments, for example, reslizumab can be administered to said patient intravenously. In other embodiments, reslizumab can be administered to said patient subcutaneously.

As used herein, the phrase "therapeutically effective dose" refers to an amount of a reslizumab, as described herein, effective to achieve a particular biological or therapeutic result such as, but not limited to, biological or therapeutic results disclosed, described, or exemplified herein. The therapeutically effective dose may vary according to factors such as the disease state, age, sex, and weight of the individual, and the ability of the composition to cause a desired response in a subject. Such results include, but are not limited to, the treatment of moderate to severe eosinophilic asthma, as determined by any means suitable in the art.

As used herein, forced expiratory volume in 1 second ($FEV_1$) refers to the maximal amount of air that can forcefully be exhaled in one second.

As used herein, asthma control questionnaire (ACQ) refers to a questionnaire used to measure the adequacy of asthma control and change in asthma control which occurs either spontaneously or as a result of treatment.

As used herein, forced vital capacity (FVC) refers to the volume delivered during an expiration made as forcefully and completely as possible starting from full inspiration.

As used herein, forced expiratory flow ($FEF_{25\%-75\%}$) refers to the average forced expiratory flow during the mid (25-75%) portion of the FVC.

As used herein, asthma quality of life questionnaire (AQLQ) refers to a disease-specific health-related quality of life instrument that evaluates both physical and emotional impact of disease.

As used herein, asthma symptom utility index (AUSI) refers to a brief, interviewer-administered, patient preference-based scale assessing frequency and severity of selected asthma-related symptoms and treatment side effects.

As used herein, clinical asthma exacerbations (CAEs) refers to a medical intervention (either additional therapy beyond the patients usual care and/or and emergency room visit or hospital admission due to asthma) that was clinically judged (adjudicated by a committee independent of Teva) precipitated by a deterioration in lung function and/or worsening patient symptoms. Medical interventions that were considered as definitive of asthma exacerbations included either or both of:

1) use of systemic, or an increase in the use of inhaled, corticosteroid treatment for 3 or more days. For patients already being treated with systemic or inhaled corticosteroids, the dose of corticosteroids will need to be increased 2 or more fold for at least 3 or more days; and/or
2) asthma-related emergency treatment including at least 1 of: an unscheduled visit to the physician's office for nebulizer treatment or other urgent treatment to prevent worsening of asthma symptoms; a visit to the emergency room for asthma-related treatment; or an asthma-related hospitalization.

Disclosed herein are methods of treating moderate to severe eosinophilic asthma in a patient comprising: 1) identifying a patient having moderate to severe eosinophilic asthma, wherein the patient's symptoms are inadequately controlled with a current asthma therapeutic and wherein the patient's blood eosinophil levels are equal to or greater than about 400/µl; and 2) administering to said patient a therapeutically effective dose of reslizumab.

Patients with eosinophilic asthma have elevated eosinophils in the lung, sputum and blood. As used herein, "moderate to severe asthma" is defined by a baseline medication requirement of at least medium dose inhaled corticosteroid (for example, ICS ≥440 micrograms of fluticasone daily dose) with or without another asthma controller. In some embodiments, for example, moderate to severe asthma can be a baseline medication requirement of at least medium dose inhaled corticosteroid (for example, ICS ≥440 micrograms of fluticasone daily dose) with another asthma controller. In other embodiments, moderate to severe asthma can be a baseline medication requirement of at least medium dose inhaled corticosteroid (for example, ICS ≥440 micrograms of fluticasone daily dose) without another asthma controller. As used herein, "moderate to severe eosinophilic asthma" is defined as moderate to severe asthma with a baseline blood eosinophil count of at least about 400/µL.

Suitable patients to be treated with the disclosed methods are those whose asthma symptoms are inadequately controlled using their current asthma therapeutic. As used herein, "inadequately controlled" refers to an Asthma Control Questionnaire (ACQ) score of ≥1.5.

The patient's current therapeutic can be an inhaled corticosteroid (ICS) with or without another controller. In some embodiments, the patient's current asthma therapeutic can comprise an inhaled corticosteroid without another controller. In some embodiments, the patient's current asthma therapeutic can comprise an inhaled corticosteroid with another controller. The patient's current therapeutic can be a medium dose of inhaled corticosteroid. For example, the inhaled corticosteroid can be at least equivalent to about 440 µg fluticasone. The patient's current therapeutic can be a high dose of inhaled corticosteroid. Exemplary cut-offs for high doses of inhaled corticosteroids are provided, for example, in Table 18. In embodiments wherein the patient's current asthma therapeutic comprises an inhaled corticosteroid with another controller, the other controller can comprise a long acting beta 2 adrenoceptor agonist (LABA). In some embodiments, the patient's current asthma therapeutic can comprise equal to or greater than about 440 µg fluticasone and a long acting beta 2 adrenoceptor agonist (LABA).

Suitable patients also include those having an elevated level of blood eosinophils. An "elevated level of blood eosinophils" refers to an eosinophil level that selects patients with currently active eosinophilic airway inflammation with high specificity. For example, an elevated level of blood eosinophils can include a higher level of blood eosinophils in the patient compared to an individual, or population of individuals, that does not have asthma. In some embodiments, the patient's blood eosinophil level can be equal to or greater than about 400/µL. In some embodiments, the patient's blood eosinophil level can be equal to or greater than about 450/µl. In some embodiments, the patient's blood eosinophil level can be equal to or greater than about 500/µl. In some embodiments, the patient's blood eosinophil level can be equal to or greater than about 550/µl. In some embodiments, the patient's blood eosinophil level can be equal to or greater than about 600/µl. In some embodiments, the patient's blood eosinophil level can be equal to or greater than about 650/µl. In some embodiments, the patient's blood eosinophil level can be equal to or greater than about 700/µl. In some embodiments, the patient's blood eosinophil level can be equal to or greater than about 750/µl. In some embodiments, the patient's blood eosinophil level can be equal to or greater than about 800/µL. In some embodiments, the patient's blood eosinophil level can be equal to or greater than about 850/µl. In some embodiments, the patient's blood eosinophil level can be equal to or greater than about 900/µl. In some embodiments, the patient's blood eosinophil level can be equal to or greater than about 950/µl. In some embodiments, the patient's blood eosinophil level can be equal to or greater than about 1000/µl. In some embodiments, the patient's blood eosinophil level can be equal to or greater than about 1500/µl.

As used herein, "reslizumab" refers to a "humanized" (from rat) divalent monoclonal antibody (mAb) with an IgG4 kappa isotype, with binding affinity for a specific epitope on the human interleukin-5 (IL-5) molecule. Reslizumab is a neutralizing antibody that is believed to block IL-5 dependent cell proliferation and/or eosinophil production. Reslizumab is described in, for example, Walsh, G M (2009) "Reslizumab, a humanized anti-IL-5 mAb for the treatment of eosinophil-mediated inflammatory conditions" *Current opinion in molecular therapeutics* 11 (3): 329-36; U.S. Pat. No. 6,056,957 (Chou); U.S. Pat. No. 6,451,982 (Chou); U.S. RE39,548 (Bodmer), each of which is incorporated herein by reference.

The sequences of the heavy and light chains of reslizumab are as follows:

| Heavy Chain (SEQ ID NO: 1) | EVQLVESGGGLVQPGGSLRLSCAVSGLSLTSNSVNWI RQAPGKGLEWVGLIWSNGDTDYNSAIKSRFTISRDTS KSTVYLQMNSLRAEDTAVYYCAREYYGYFDYWGQGTL VTVSSASTKGPSVFPLAPCSRSTSESTAALGCLVKDY FPEPVTVSWNSGALTSGVHTFPAVLQSSGLYSLSSVV TVPSSSLGTKTYTCNVDHKPSNTKVDKRVESKYGPPC PSCPAPEFLGGPSVFLFPPKPKDTLMISRTPEVTCVV VDVSQEDPEVQFNWYVDGVEVHNAKTKPREEQFNSTY RVVSVLTVLHQDWLNGKEYKCKVSNKGLPSSIEKTIS KAKGQPREPQVYTLPPSQEEMTKNQVSLTCLVKGFYP SDIAVEWESNGQPENNYKTTPPVLDSDGSFFLYSRLT VDKSRWQEGNVFSCSVMHEALHNHYTQKSLSLSLGK |

Light Chain
(SEQ ID
NO: 2)
```
DIQMTQSPSSLSASVGDRVTITCLASEGISSYLAWYQ
QKPGKAPKLLIYGANSLQTGVPSRFSGSGSATDYTLT
ISSLQPEDFATYYCQQSYKFPNTFGQGTKVEVKRTVA
APSVFIFPPSDEQLKSGTASVVCLLNNFYPREAKVQW
KVDNALQSGNSQESVTEQDSKDSTYSLSSTLTLSKAD
YEKHKVYACEVTHQGLSSPVTKSFNRGEC
```

A therapeutically effective dose of reslizumab can be between about 0.3 mg/kg to about 3 mg/kg. In some embodiments, the therapeutically effective dose of reslizumab can be about 0.3 mg/kg. In some embodiments, the therapeutically effective dose of reslizumab can be about 0.5 mg/kg. In some embodiments, the therapeutically effective dose of reslizumab can be about 0.7 mg/kg. In some embodiments, the therapeutically effective dose of reslizumab can be about 1 mg/kg. In some embodiments, the therapeutically effective dose of reslizumab can be about 1.2 mg/kg. In some embodiments, the therapeutically effective dose of reslizumab can be about 1.4 mg/kg. In some embodiments, the therapeutically effective dose of reslizumab can be about 1.6 mg/kg. In some embodiments, the therapeutically effective dose of reslizumab can be about 1.8 mg/kg. In some embodiments, the therapeutically effective dose of reslizumab can be about 2.0 mg/kg. In some embodiments, the therapeutically effective dose of reslizumab can be about 2.2 mg/kg. In some embodiments, the therapeutically effective dose of reslizumab can be about 2.4 mg/kg. In some embodiments, the therapeutically effective dose of reslizumab can be about 2.6 mg/kg. In some embodiments, the therapeutically effective dose of reslizumab can be about 2.8 mg/kg. In other embodiments, the therapeutically effective dose of reslizumab can be about 3 mg/kg.

Numerous routes of administration are suitable including, but not limited to, intravenously (iv) or subcutaneously (sub-Q). In some embodiments, the therapeutically effective dose of reslizumab can be administered intravenously. In other embodiments, the therapeutically effective dose of reslizumab can be administered subcutaneously.

Suitable dosing schedules include, but are not limited to, one dose of a therapeutically effective dose of reslizumab once about every four weeks. In some embodiments, for example, the therapeutically effective dose of reslizumab is about 0.3 mg/kg to about 3 mg/kg administered intravenously or subcutaneously once about every 4 weeks. In some aspects, for example, the therapeutically effective dose of reslizumab is about 0.3 mg/kg administered intravenously or subcutaneously once about every 4 weeks. In some aspects, for example, the therapeutically effective dose of reslizumab is about 3 mg/kg administered intravenously or subcutaneously once about every 4 weeks.

Numerous criteria can be used to evaluate the efficacy of the disclosed methods. Suitable efficacy determinations include, but are not limited to, the frequency of clinical asthma exacerbations (CAEs), lung function (forced expiratory volume in 1 second ($FEV_1$), forced vital capacity (FVC), and forced expiratory flow rate ($FEF_{25\%-75\%}$)), asthma quality of life questionnaire score (AQLQ), asthma control questionnaire score (ACQ), time to first CAE, asthma symptom score (ASUI), use of rescue inhaler, blood eosinophil counts, or any combination thereof. In some embodiments, for example, administration of the therapeutically effective dose of reslizumab leads to an improvement in lung function, as assessed by improvements in forced expiratory volume in 1 second, forced vital capacity, forced expiratory mid-flow rate ($FEF_{25\%-75\%}$), or any combination thereof by about 5% or greater. For example, in some embodiments, administration of the therapeutically effective dose of reslizumab leads to an about 5% improvement in lung function. In some embodiments, administration of the therapeutically effective dose of reslizumab leads to an about 10% improvement in lung function. In some embodiments, administration of the therapeutically effective dose of reslizumab leads to an about 15% improvement in lung function. In some embodiments, administration of the therapeutically effective dose of reslizumab leads to an about 20% improvement in lung function. In some embodiments, administration of the therapeutically effective dose of reslizumab leads to an about 25% improvement in lung function. In some embodiments, administration of the therapeutically effective dose of reslizumab leads to an about 30% improvement in lung function. In some embodiments, administration of the therapeutically effective dose of reslizumab leads to an about 35% improvement in lung function. In some embodiments, administration of the therapeutically effective dose of reslizumab leads to an about 40% improvement in lung function. In some embodiments, administration of the therapeutically effective dose of reslizumab leads to an about 45% improvement in lung function. In some embodiments, administration of the therapeutically effective dose of reslizumab leads to an about 50% improvement in lung function.

In other embodiments, administration of the therapeutically effective dose of reslizumab leads to an about 5% to about 50% improvement in lung function. In other embodiments, administration of the therapeutically effective dose of reslizumab leads to an about 10% to about 50% improvement in lung function. In other embodiments, administration of the therapeutically effective dose of reslizumab leads to an about 20% to about 50% improvement in lung function. In other embodiments, administration of the therapeutically effective dose of reslizumab leads to an about 30% to about 50% improvement in lung function. In other embodiments, administration of the therapeutically effective dose of reslizumab leads to an about 40% to about 50% improvement in lung function.

Administration of the therapeutically effective dose of reslizumab can lead to reduced clinical asthma exacerbations, reduced use of systemic corticosteroids, improved asthma control questionnaire score, improved asthma quality of life questionnaire score, or any combination thereof. In some aspects, the clinical asthma exacerbations can be reduced by about 50% as compared to a patient not receiving reslizumab. In other aspects, the use of systemic corticosteroids can be reduced by about 50% as compared to a patient not receiving reslizumab.

The disclosed methods can be used to treat a patient having late-onset asthma. Accordingly, in some embodiments the methods of treating moderate to severe eosinophilic asthma in a patient can comprise: 1) identifying a patient having moderate to severe eosinophilic asthma, wherein the patient's symptoms are inadequately controlled with a current asthma therapeutic, wherein the patient's blood eosinophil levels are equal to or greater than about 400/µl, and wherein the patient has late-onset asthma; and 2) administering to said patient a therapeutically effective dose of reslizumab.

As used herein, "late-onset asthma" refers to an asthma diagnosis in a patient that is 40 years old or older at the time of initial diagnosis.

Administration of the therapeutically effective dose of reslizumab to a patient having late-onset asthma can lead to an improvement in lung function compared to a patient not receiving reslizumab. In some embodiments, administration of the therapeutically effective dose of reslizumab to a patient having late-onset asthma leads to greater than about 90 ml change in forced expiratory volume in 1 second ($\Delta FEV_1$) compared to a patient not receiving reslizumab. In some embodiments, administration of the therapeutically effective dose of reslizumab to a patient having late-onset asthma leads to greater than about 105 ml change in forced expiratory volume in 1 second ($\Delta FEV_1$) compared to a patient not receiving reslizumab. In some embodiments, administration of the therapeutically effective dose of reslizumab to a patient having late-onset asthma leads to greater than about 125 ml change in forced expiratory volume in 1 second ($\Delta FEV_1$) compared to a patient not receiving reslizumab. In some embodiments, administration of the therapeutically effective dose of reslizumab to a patient having late-onset asthma leads to greater than about 135 ml change in $\Delta FEV_1$ compared to a patient not receiving reslizumab. In some embodiments, administration of the therapeutically effective dose of reslizumab to a patient having late-onset asthma leads to greater than about 145 ml change in $\Delta FEV_1$ compared to a patient not receiving reslizumab. In some embodiments, administration of the therapeutically effective dose of reslizumab to a patient having late-onset asthma leads to greater than about 155 ml change in $\Delta FEV_1$ compared to a patient not receiving reslizumab. In some embodiments, administration of the therapeutically effective dose of reslizumab to a patient having late-onset asthma leads to greater than about 165 ml change in $\Delta FEV_1$ compared to a patient not receiving reslizumab. In some embodiments, administration of the therapeutically effective dose of reslizumab to a patient having late-onset asthma leads to greater than about 175 ml change in $\Delta FEV_1$ compared to a patient not receiving reslizumab. In some embodiments, administration of the therapeutically effective dose of reslizumab to a patient having late-onset asthma leads to greater than about 190 ml change in forced expiratory volume in 1 second ($\Delta FEV_1$) compared to a patient not receiving reslizumab. In some embodiments, administration of the therapeutically effective dose of reslizumab to a patient having late-onset asthma leads to greater than about 205 ml change in forced expiratory volume in 1 second ($\Delta FEV_1$) compared to a patient not receiving reslizumab. In some embodiments, administration of the therapeutically effective dose of reslizumab to a patient having late-onset asthma leads to greater than about 220 ml change in forced expiratory volume in 1 second ($\Delta FEV_1$) compared to a patient not receiving reslizumab. In some embodiments, administration of the therapeutically effective dose of reslizumab to a patient having late-onset asthma leads to greater than about 235 ml change in forced expiratory volume in 1 second ($\Delta FEV_1$) compared to a patient not receiving reslizumab. In some embodiments, administration of the therapeutically effective dose of reslizumab to a patient having late-onset asthma leads to greater than about 245 ml change in forced expiratory volume in 1 second ($\Delta FEV_1$) compared to a patient not receiving reslizumab.

Administration of the therapeutically effective dose of reslizumab to a patient having late-onset asthma can lead to an about 90 ml to about 250 ml change in $\Delta FEV_1$ compared to a patient not receiving reslizumab. Administration of the therapeutically effective dose of reslizumab to a patient having late-onset asthma can lead to an about 125 ml to about 250 ml change in $\Delta FEV_1$ compared to a patient not receiving reslizumab. Administration of the therapeutically effective dose of reslizumab to a patient having late-onset asthma can lead to an about 150 ml to about 250 ml change in $\Delta FEV_1$ compared to a patient not receiving reslizumab. Administration of the therapeutically effective dose of reslizumab to a patient having late-onset asthma can lead to an about 175 ml to about 250 ml change in $\Delta FEV_1$ compared to a patient not receiving reslizumab. Administration of the therapeutically effective dose of reslizumab to a patient having late-onset asthma can lead to an about 200 ml to about 250 ml change in $\Delta FEV_1$ compared to a patient not receiving reslizumab. Administration of the therapeutically effective dose of reslizumab to a patient having late-onset asthma can lead to an about 90 ml to about 200 ml change in $\Delta FEV_1$ compared to a patient not receiving reslizumab. Administration of the therapeutically effective dose of reslizumab to a patient having late-onset asthma can lead to an about 90 ml to about 175 ml change in $\Delta FEV_1$ compared to a patient not receiving reslizumab. Administration of the therapeutically effective dose of reslizumab to a patient having late-onset asthma can lead to an about 90 ml to about 150 ml change in $\Delta FEV_1$ compared to a patient not receiving reslizumab. Administration of the therapeutically effective dose of reslizumab to a patient having late-onset asthma can lead to an about 90 ml to about 125 ml change in $\Delta FEV_1$ compared to a patient not receiving reslizumab.

Administration of the therapeutically effective dose of reslizumab to a patient having late-onset asthma can lead to a reduction of clinical asthma exacerbations compared to a patient not receiving reslizumab. In some aspects, administration of the therapeutically effective dose of reslizumab to a patient having late-onset asthma leads to an about 50% reduction in clinical asthma exacerbations compared to a patient not receiving reslizumab. In some aspects, administration of the therapeutically effective dose of reslizumab to a patient having late-onset asthma leads to greater than about 50% reduction in clinical asthma exacerbations compared to a patient not receiving reslizumab. For example, administration of the therapeutically effective dose of reslizumab to a patient having late-onset asthma can lead to a 50% reduction in clinical asthma exacerbations compared to a patient not receiving reslizumab. Administration of the therapeutically effective dose of reslizumab to a patient having late-onset asthma can lead to a 55% reduction in clinical asthma exacerbations compared to a patient not receiving reslizumab. Administration of the therapeutically effective dose of reslizumab to a patient having late-onset asthma can lead to a 60% reduction in clinical asthma exacerbations compared to a patient not receiving reslizumab. Administration of the therapeutically effective dose of reslizumab to a patient having late-onset asthma can lead to a 65% reduction in clinical asthma exacerbations compared to a patient not receiving reslizumab. Administration of the therapeutically effective dose of reslizumab to a patient having late-onset asthma can lead to a 70% reduction in clinical asthma exacerbations compared to a patient not receiving reslizumab. Administration of the therapeutically effective dose of reslizumab to a patient having late-onset asthma can lead to a 75% reduction in clinical asthma exacerbations compared to a patient not receiving reslizumab. Administration of the therapeutically effective dose of reslizumab to a patient having late-onset asthma can lead to a 80% reduction in clinical asthma exacerbations compared to a patient not receiving reslizumab. In some embodiments, administration of the therapeutically effective dose of reslizumab to a patient having late-onset asthma leads to an about 50% to about 80% reduction in clinical asthma exacerbations compared to a patient not receiving reslizumab. In some embodiments, administration of the therapeutically effective dose of reslizumab to a patient having late-onset asthma leads to an about 60% to about 75% reduction in clinical asthma exacerbations compared to a patient not receiving reslizumab. In some embodiments, administration of the therapeutically effective dose of reslizumab to a patient having late-onset asthma leads to an about 70% to about 80% reduction in clinical asthma exacerbations compared to a patient not receiving reslizumab.

EXAMPLES

Example 1: Study 1—Treatment with Placebo, Reslizumab 0.3 Mg/Kg, or Reslizumab 3.0 Mg/Kg Once Every 4 Weeks for a Total of 4 Doses (16 Weeks)

Aim

Studies were conducted to determine whether reslizumab, at a dosage of 0.3 mg/kg or 3.0 mg/kg administered once every 4 weeks for a total of 4 doses, is more effective than placebo in improving pulmonary function and asthma control in asthma patients with elevated eosinophil levels.

Study Design

A global Phase 3, multicenter, randomized, double-blind, placebo-controlled, parallel-group, fixed dosage study was performed to compare the efficacy and safety of reslizumab (RES) vs placebo (PBO) in subjects with moderate to severe, persistent asthma with elevated eosinophil levels. Eligible subjects were randomized (1:1:1) to receive placebo, reslizumab 0.3 mg/kg, or reslizumab 3.0 mg/kg administered once every 4 weeks for a total of 4 doses. Subjects had the option to enroll in an open-label extension study after completing the 16-week double-blind treatment period.

Subjects

Eligible subjects were between the ages of 12 and 75 and had moderate to severe asthma based on prior medication requirement: ≥440 μg per day of fluticasone or equivalent±another controller (e.g., LABA). The asthma had to be inadequately controlled based on an Asthma Control Questionnaire (ACQ) score of ≥1.5. Subjects were required to have a baseline blood eosinophil count of ≥400/μL. There was no specific forced expiratory volume in 1 second ($FEV_1$) or asthma exacerbation exclusion.

Outcome Variables

The primary efficacy variable was the change from baseline in $FEV_1$. Secondary efficacy variables included: ACQ score (the self-administered portion of the ACQ-7 consists of 5 items scoring symptoms and 1 item scoring rescue medication use, as well as other lung function ($FEV_1$ measurements conducted in the clinic; forced vital capacity (FVC); forced expiratory flow 25-75% ($FEF_{25\%-75\%}$); asthma quality of life questionnaire (AQLQ); asthma symptoms (via the ASUI tool); use of reliever short acting beta agonist (SABA); and safety (adverse events).

Statistics

The efficacy analyses were based on the full analysis set (all randomized patients who were treated with at least 1 dose of study drug) and treatment group as randomized. Efficacy variables were analyzed using mixed model repeated measures (MMRM) with fixed effects (treatment, stratification factors, sex, visit, interaction of treatment and visit), covariates (height, baseline value), and patient as the block factor for the repeated measurements. An unstructured covariance matrix was used for within-patient correlation modeling. The overall treatment effect for each reslizumab dose was compared with placebo using a 2-sided test at the significance level of 0.05. A stratified Cochran-Mantel-Haenszel (CMH) test was used to analyze the proportion of patients achieving at least a 0.5-point reduction in ACQ.

Results

Of the 1025 subjects who were screened, 315 met eligibility criteria and were randomized. Of the 315 patients who were randomized, 268 (85%) completed the study (81%, 89%, and 85% in the placebo, reslizumab 0.3 mg/kg, and reslizumab 3.0 mg/kg groups, respectively). Overall, the most common reason for discontinuation was adverse events (n=19 overall; n=11 placebo; n=1 reslizumab 0.3 mg/kg; n=7 reslizumab 3.0 mg/kg), followed by withdrawn consent (n=7 overall; n=2 placebo; n=1 reslizumab 0.3 mg/kg; n=4 reslizumab 3.0 mg/kg), lack of efficacy (n=6 overall; n=2 placebo; n=3 reslizumab 0.3 mg/kg; n=1 reslizumab 3.0 mg/kg), and protocol violation (n=6 overall; n=2 placebo; n=3 reslizumab 0.3 mg/kg; n=1 reslizumab 3.0 mg/kg). The full analysis set and the safety population included 311 subjects (placebo: n=105; reslizumab 0.3 mg/kg: n=103; reslizumab 3.0 mg/kg: n=103). Results are based on the full analysis set, unless otherwise specified. Baseline subject demographics and disease characteristics are summarized in Tables 1 and 2.

TABLE 1

|  | PBO (105) | Resli 0.3 mg/kg (104) | Resli 3.0 mg/kg (106) | Total (315) |
|---|---|---|---|---|
| Age | 44.2 | 44.5 | 43 | 43.9 |
| 12-17 n (%) | 5 (5) | 5 (5) | 5 (5) | 15 (5) |
| F/M (%) | 59/41 | 57/43 | 58/42 | 58/42 |
| Race (%) | | | | |
| white | 81 | 77 | 85 | 81 |
| black | 7 | 6 | 5 | 6 |
| remaining | 12 | 17 | 10 | 13 |
| Predominant Ethnicities | | | | |
| Non-hispanic non-latino | 70 | 70 | 71 | 70 |
| Hispanic or Latino | 28 | 28 | 29 | 28 |
| BMI (kg/m$^2$) | 27.7 | 27.6 | 27.4 | 27.6 |

TABLE 2

|  | PBO (105) | Resli 0.3 mg/kg (104) | Resli 3.0 mg/kg (106) | Total (315) |
|---|---|---|---|---|
| Time since Dx (yr) | 20 | 20.7 | 20.4 | 20.4 |
| Asthma EXAC prior 12 mo? YES (%) | 56 | 55 | 55 | 55 |
| ACQ | 2.5 | 2.5 | 2.6 | 2.5 |
| AQLQ | 4.374 | 4.479 | 4.164 | — |
| ASUI | 0.674 | 0.675 | 0.657 | — |
| Reversibility (%) | 25.2 | 24.2 | 26.2 | 25.3 |
| $FEV_1$ (L) | 2.22 | 2.16 | 2.17 | — |
| $FEV_1$ % predicted | 71.1 | 68.8 | 70.4 | 70.1 |
| Rescue use (puff/day) | 2.3 | 1.9 | 2.3 | — |
| Blood EOS × 10$^9$/L (range) | 0.6 (0.1-3.7) | 0.6 (0.1-3.7) | 0.6 | 0.6 (0-1.6) |
| % on a LABA* | 82 | 80 | 78 | — |

*Long acting beta agonist: not specifically programmed

Change from Baseline in $FEV_1$

The analysis of the primary efficacy variable, overall change from baseline in $FEV_1$ over 16 weeks of treatment (obtained from the MMRM estimation) showed significant improvement (increase) in $FEV_1$ for patients in both reslizumab treatment groups compared with placebo (Table 3). The overall change from baseline in $FEV_1$ was 0.126 L, 0.242 L, and 0.286 L for the patients in the placebo, 0.3 mg/kg reslizumab, and 3.0 mg/kg reslizumab treatment groups, respectively. The overall treatment effect was larger for patients in the reslizumab 3.0 mg/kg treatment group (0.160 L, p=0.0018) than for patients in the reslizumab 0.3 mg/kg treatment group (0.115 L, p=0.0237).

Figure 1A:
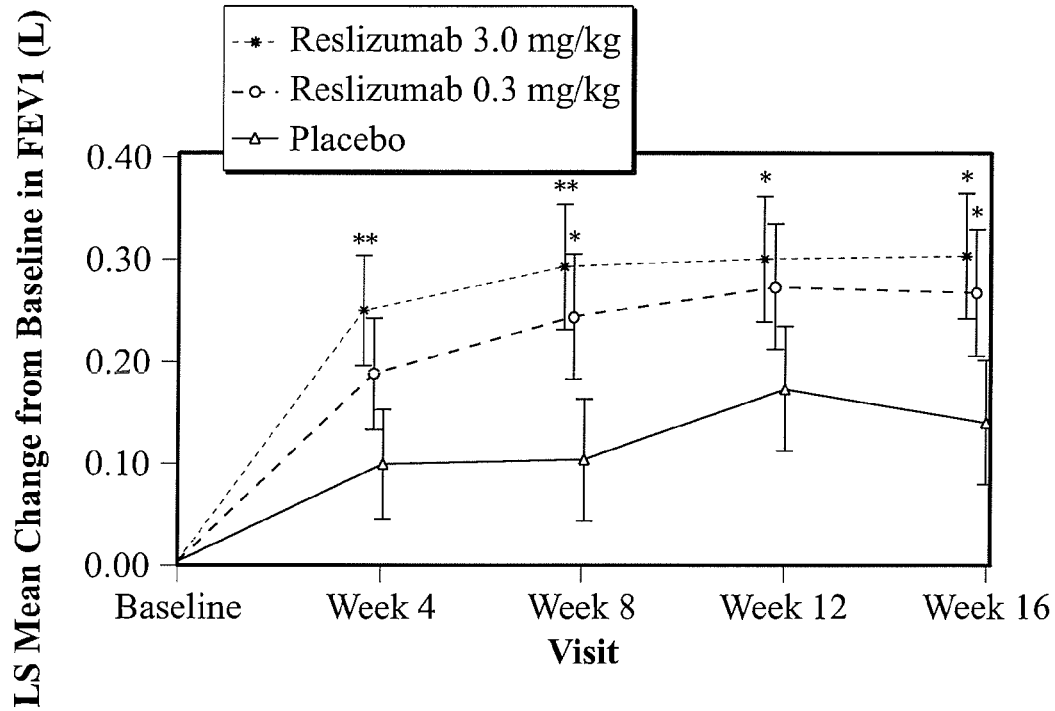
FIG. 1A and FIG. 1B represent the change (SE) from baseline in $FEV_1$ by treatment group and visit (FIG. 1A) and overall change from baseline (primary efficacy) in $FEV_1$ (FIG. 1B) after 16 weeks of treatment in study 1. All inferential statistics are derived from MMRM with treatment, visit, treatment by visit interaction, age group, history of asthma exacerbation in the previous 12 months, height, baseline, sex, and patient as a random effect. Data are least-squared means±standard error. Δ=treatment difference (reslizumab–placebo). SE=standard error; LS=Least Squares. * p≤0.05, ** p≤0.005 versus placebo. P values are not adjusted to control for multiplicity. Placebo=solid line; reslizumab 0.3 mg/kg=shorter hashes; reslizumab 3.0 mg/kg=longer hashes.
Figure 1B:
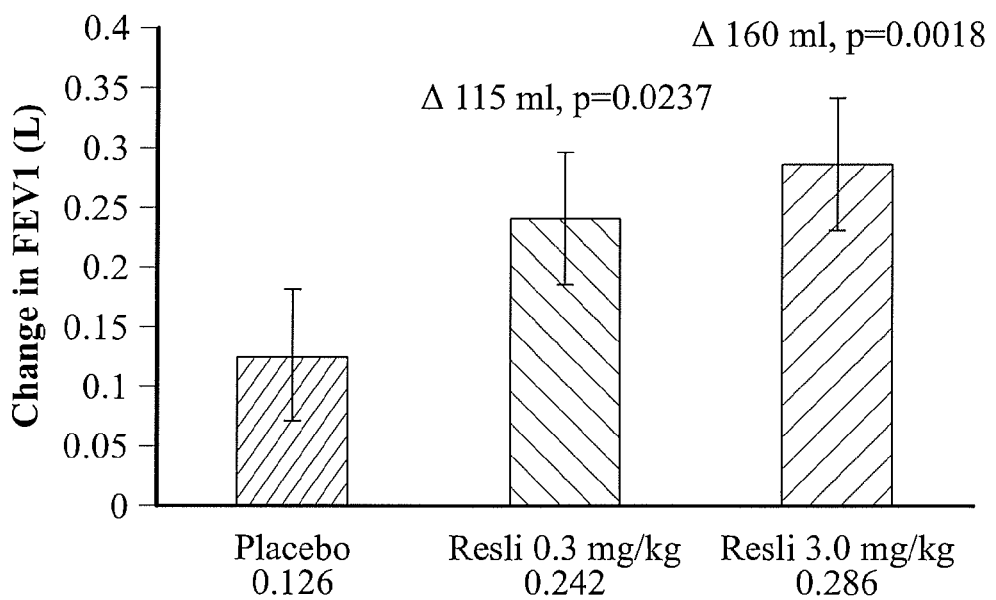

The treatment effect for change in $FEV_1$ from baseline to weeks 4, 8, 12, 16, and endpoint for patients in the 0.3 mg/kg and 3.0 mg/kg reslizumab treatment groups were analyzed secondarily (FIG. 1 and Table 3). A treatment effect in $FEV_1$ was seen after the first dose of 3.0 mg/kg reslizumab at the first scheduled 4-week assessment (0.153 L, p=0.003) that was sustained at the 16-week assessment (0.165 L, p=0.0118). Improvements for patients in the 0.3 mg/kg reslizumab treatment group were more variable, but numerically greater than those for patients in the placebo treatment group at every clinic visit.

Substantial placebo effects are not unexpected given that patients were allowed to continue SoC Tx and likely become more compliant during the study. Significant improvements in $FEV_1$ were observed in subjects as early as 4 weeks after treatment with reslizumab 3.0 mg/kg compared with placebo (treatment difference: 153 ml, P=0.003 and maintained over the duration of the study.

TABLE 3

| Variable (unit) | Statistic | Placebo (N = 105) | Reslizumab 0.3 mg/kg (N = 103) | Reslizumab 3.0 mg/kg (N = 103) |
| --- | --- | --- | --- | --- |
| Baseline $FEV_1$ (liters) | Mean | 2.222 | 2.157 | 2.169 |
| | SD | 0.8125 | 0.8506 | 0.7815 |
| | SE of mean | 0.0793 | 0.0838 | 0.0770 |
| | Median | 2.120 | 2.060 | 2.140 |
| | Min, max | 0.600, 4.510 | 0.560, 4.500 | 0.570, 4.022 |
| Change in $FEV_1$ (liters) Over 16 Weeks | $n^{a)}$ | 103 | 101 | 102 |
| | LS mean | 0.126 | 0.242 | 0.286 |
| | SE of LS mean | 0.0549 | 0.0556 | 0.0548 |
| | Treatment difference (active − placebo) | | 0.115 | 0.160 |
| | SE of difference | | 0.0508 | 0.0507 |
| | 95% CI | | (0.016, 0.215) | (0.060, 0.259) |
| | p-value | | 0.0237 | 0.0018 |
| Week 16 change in $FEV_1$ (liters) | n | 84 | 92 | 91 |
| | Mean | 0.052 | 0.188 | 0.243 |
| | SD | 0.3944 | 0.5568 | 0.4782 |
| | SE of mean | 0.0430 | 0.0581 | 0.0501 |
| | Median | 0.000 | 0.105 | 0.170 |
| | Min, max | −0.760, 1.430 | −1.080, 2.670 | −0.890, 1.970 |
| | LS mean | 0.137 | 0.266 | 0.302 |
| | SE of LS mean | 0.0622 | 0.0624 | 0.0616 |
| | Treatment difference (Active − Placebo) | | 0.129 | 0.165 |
| | SE of difference | | 0.0651 | 0.0651 |
| | 95% CI | | (0.001, 0.257) | (0.037, 0.293) |
| | p-value | | 0.0481 | 0.0118 |

$^{a)}$n denotes number of patients who contributed at least once to the analysis.

$FEV_1$ = forced expiratory volume in 1 second; SD = standard deviation; SE = standard error; min = minimum; max = maximum; LS = Least Squares; CI = confidence interval Note:

Endpoint = Week 16 or early withdrawal.

Change from Baseline in FVC by Visit

Figure 2A:
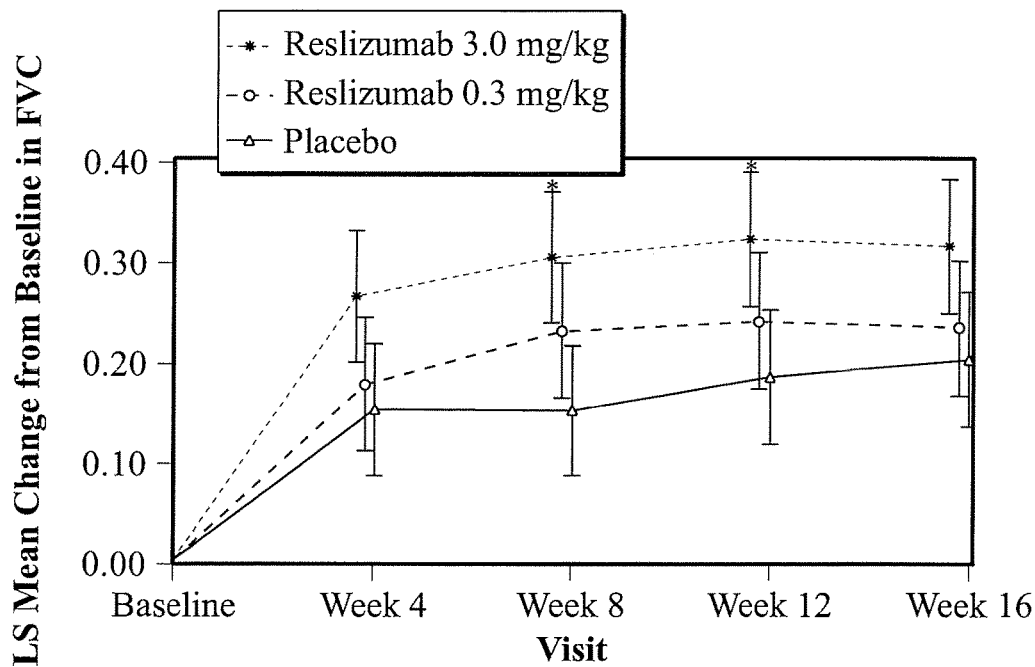
FIG. 2A and FIG. 2B represent the change (SE) from baseline to each visit in FVC by treatment group (FIG. 2A) and overall change from baseline in FVC (FIG. 2B) after 16 weeks of treatment in study 1. SE=standard error; LS=Least Squares. * p≤0.05 versus placebo. P values are not adjusted to control for multiplicity. Placebo=solid line; reslizumab 0.3 mg/kg=shorter hashes; reslizumab 3.0 mg/kg=longer hashes.
Figure 2B:
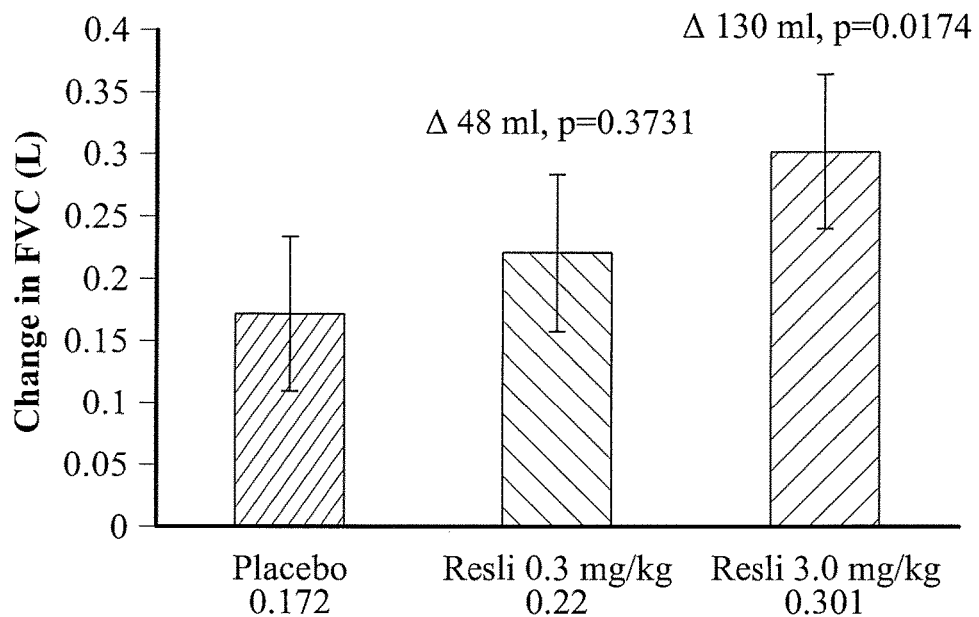

The overall change from baseline in FVC over 16 weeks of treatment showed improvement (increase) in the reslizumab 3.0 mg/kg treatment group compared with placebo (0.130 L, p=0.0174) (Table 4). The overall treatment effect for the 0.3 mg/kg reslizumab group compared with placebo was 0.048 L (p=0.3731). Improvement in FVC by visit was observed for patients in the reslizumab 3.0 mg/kg treatment group by 8 weeks after the second dose of reslizumab (0.153 L, p=0.0190) that was sustained throughout the 16 week treatment period. Improvements for patients in the reslizumab 0.3 mg/kg treatment group were numerically greater than placebo at every clinic visit (FIG. 2).

TABLE 4

| Variable (unit) | Statistic | Placebo (N = 105) | Reslizumab 0.3 mg/kg (N = 103) | Reslizumab 3.0 mg/kg (N = 103) |
|---|---|---|---|---|
| Baseline FVC | Mean | 3.288 | 3.289 | 3.199 |
| | SD | 1.0503 | 1.1232 | 1.0097 |
| | SE of mean | 0.1025 | 0.1107 | 0.0995 |
| | Median | 3.200 | 3.230 | 3.020 |
| | Min, max | 0.880, 6.180 | 1.290, 6.010 | 0.660, 5.640 |
| Overall change in FVC | n[a] | 103 | 101 | 102 |
| | LS mean | 0.172 | 0.220 | 0.301 |
| | SE of LS mean | 0.0614 | 0.0623 | 0.0613 |
| | Treatment difference (active − placebo) | | 0.048 | 0.130 |
| | SE of difference | | 0.0543 | 0.0543 |
| | 95% CI | | (−0.058, 0.155) | (0.023, 0.237) |
| | p-value | | 0.3731 | 0.0174 |
| Week 16 change in FVC | n | 84 | 92 | 90 |
| | LS mean | 0.201 | 0.233 | 0.315 |
| | SE of LS mean | 0.0678 | 0.0681 | 0.0672 |
| | Treatment difference (Active − Placebo) | | 0.032 | 0.114 |
| | SE of difference | | 0.0675 | 0.0676 |
| | 95% CI | | (−0.101, 0.165) | (−0.019, 0.247) |
| | p-value | | 0.6382 | 0.0930 |

[a]n denotes number of patients who contributed at least once to the analysis.
SD = standard deviation; SE = standard error; min = minimum; max = maximum; LS = Least Squares; CI = confidence interval.

Change from Baseline in $FEF_{25\%-75\%}$ by Visit

Figure 3A:
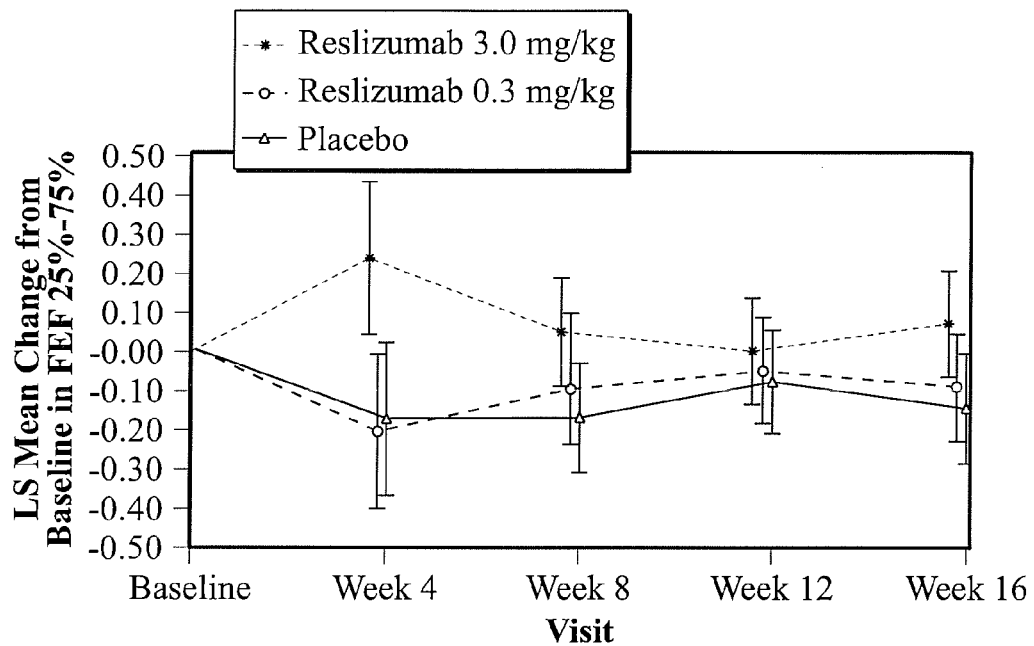
FIG. 3A and FIG. 3B represent the change (SE) from baseline to each visit in $FEF_{25\%-75\%}$ by visit and treatment group (FIG. 3A) and the overall change from baseline in $FEF_{25\%-75\%}$ (FIG. 3B) after 16 weeks of treatment in study 1. All inferential statistics are derived from MMRM with treatment, visit, treatment by visit interaction, age group, history of asthma exacerbation in the previous 12 months, height, baseline, sex, and patient as a random effect. Data are least-squared means±standard error. Δ=treatment difference (reslizumab–placebo). Placebo=solid line; reslizumab 0.3 mg/kg=shorter hashes; reslizumab 3.0 mg/kg=longer hashes.
Figure 3B:
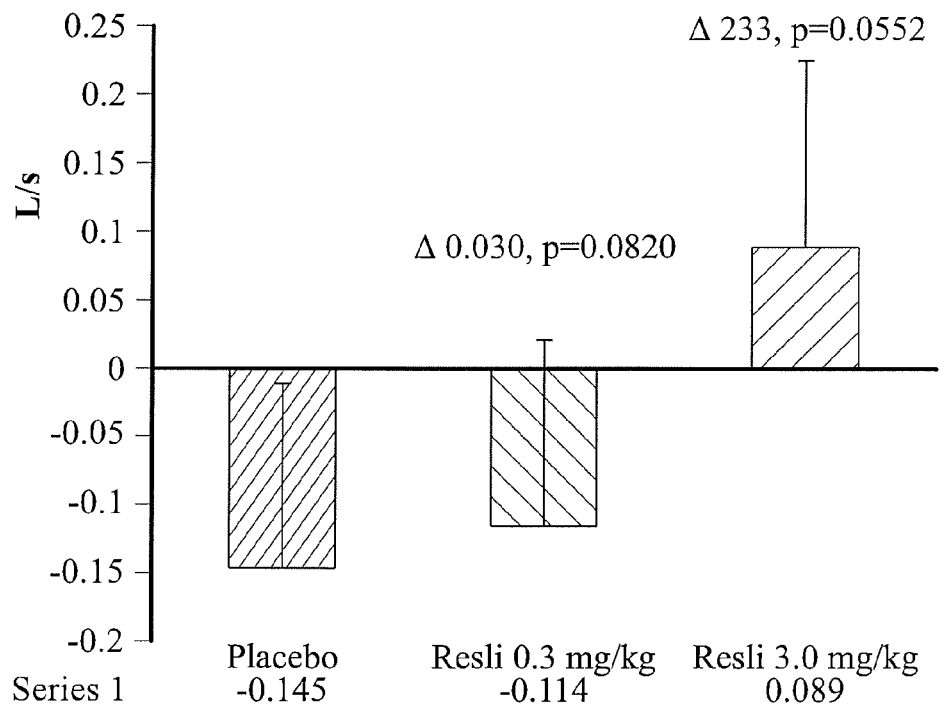

The overall LS mean change from baseline in $FEF_{25\%-75\%}$ over 16 weeks of treatment was numerically improved for patients in the reslizumab 3.0 mg/kg treatment group compared with placebo (0.233 L/second, p=0.0552). The overall treatment effect for the 0.3 mg/kg reslizumab treatment group was small (0.030 L/second, p=0.8020) (Table 5). Treatment differences were not sizable for either reslizumab treatment group compared with placebo at any of the 4-week visits following week 4 (FIG. 3).

TABLE 5

| Variable (L/s) | Statistic | Placebo (N = 105) | Reslizumab 0.3 mg/kg (N = 103) | Reslizumab 3.0 mg/kg (N = 103) |
|---|---|---|---|---|
| Baseline $FEF_{25\%-75\%}$ | Mean | 1.657 | 2.337 | 1.705 |
| | SD | 0.9201 | 8.9642 | 1.5396 |
| | SE of mean | 0.0898 | 0.8833 | 0.1517 |
| | Median | 1.510 | 1.250 | 1.450 |
| | Min, max | 0.270, 4.370 | 0.210, 92.000 | 0.360, 14.600 |
| Overall change in $FEF_{25\%-75\%}$ | n[a] | 103 | 101 | 102 |
| | LS mean | −0.145 | −0.114 | 0.089 |
| | SE of LS mean | 0.1342 | 0.1361 | 0.1342 |
| | Treatment difference (active − placebo) | | 0.030 | 0.233 |
| | SE of difference | | 0.1215 | 0.1212 |
| | 95% CI | | (−0.209, 0.270) | (−0.005, 0.472) |
| | p-value | | 0.8020 | 0.0552 |

TABLE 5-continued

| Variable (L/s) | Statistic | Placebo (N = 105) | Reslizumab 0.3 mg/kg (N = 103) | Reslizumab 3.0 mg/kg (N = 103) |
|---|---|---|---|---|
| Week 16 change in $FEF_{25\%-75\%}$ | n | 84 | 92 | 90 |
| | LS mean | −0.147 | −0.095 | 0.069 |
| | SE of LS mean | 0.1372 | 0.1384 | 0.1366 |
| | Treatment difference (Active − Placebo) | | 0.052 | 0.216 |
| | SE of difference | | 0.1276 | 0.1276 |
| | 95% CI | | (−0.199, 0.303) | (−0.035, 0.468) |
| | p-value | | 0.6818 | 0.0908 |

[a]n denotes number of patients who contributed at least once to the analysis.
$FEF_{25\%-75\%}$ = forced expiratory flow at 25% to 75% forced vital capacity; SD = standard deviation; SE = standard error; min = minimum; max = maximum; LS = Least Squares; CI = confidence interval Overall Change from Baseline in $FEV_1$ Subpopulation ($FEV_1$% Predicted ≤85%)

Figure 4:
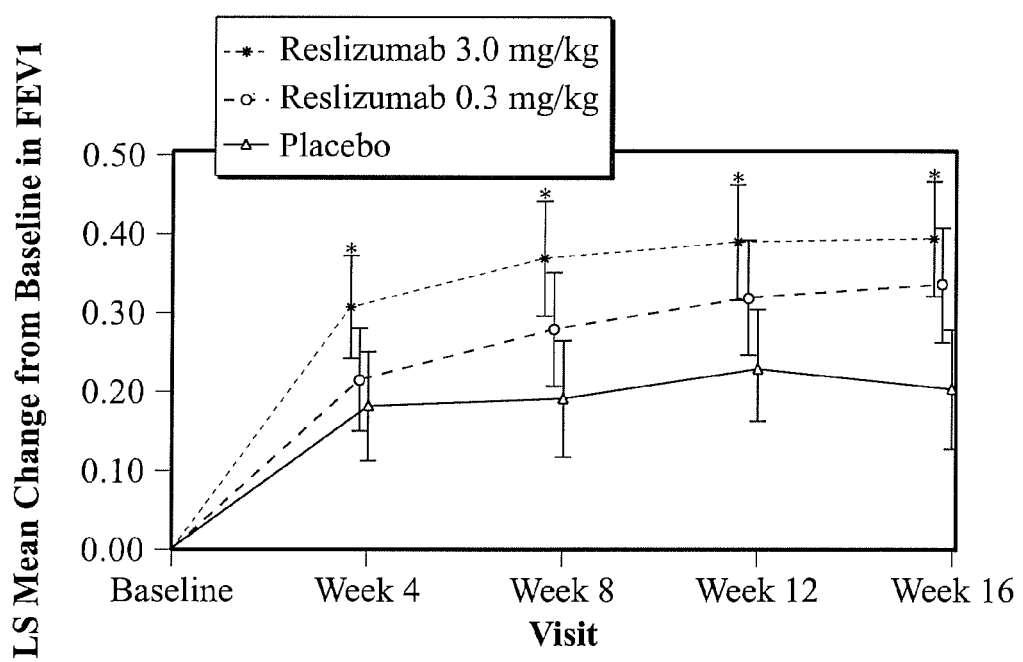
FIG. 4 represents the change from baseline in $FEV_1$ over 16 weeks by treatment group (subpopulation analysis set–patients with a baseline $FEV_1\%$ predicted of ≤85%)—in study 1. LS=Least Squares; SE=standard error. Placebo=solid line; reslizumab 0.3 mg/kg=shorter hashes; reslizumab 3.0 mg/kg=longer hashes.

No specific baseline $FEV_1$ inclusion criterion was mandated for this study. Therefore, a secondary analysis obtained from the MMRM estimation, was performed for the primary efficacy variable for patients included in the $FEV_1$ FAS with % predicted $FEV_1$≤85% at baseline to gain insight around efficacy in patients with more impaired lung function (i.e., $FEV_1$ subpopulation). The overall change from baseline in $FEV_1$ by subpopulation analysis was 0.199 L, 0.285 L, and 0.364 L for the patients in the placebo, 0.3 mg/kg reslizumab, and 3.0 mg/kg reslizumab treatment groups, respectively. Results showed numerical improvement in $FEV_1$ for both reslizumab treatment groups compared with placebo (Table 6); however, significant improvement was only observed for the reslizumab 3.0 mg/kg treatment group (treatment difference 0.165 L, p=0.0066) (FIG. 4). Of note, this analysis was performed on a smaller population for which the study was not powered.

TABLE 6

| Variable (unit) | Statistic | Placebo (N = 81) | Reslizumab 0.3 mg/kg (N = 86) | Reslizumab 3.0 mg/kg (N = 82) |
|---|---|---|---|---|
| Overall change in $FEV_1$ (liters) | n[a] | 79 | 84 | 81 |
| | LS mean | 0.199 | 0.285 | 0.364 |
| | SE of LS mean | 0.0692 | 0.0661 | 0.0666 |
| | Treatment difference (active − placebo) | | 0.087 | 0.165 |

TABLE 6-continued

| Variable (unit) | Statistic | Placebo (N = 81) | Reslizumab 0.3 mg/kg (N = 86) | Reslizumab 3.0 mg/kg (N = 82) |
|---|---|---|---|---|
| | SE of difference | | 0.0597 | 0.0603 |
| | 95% CI | | (−0.031, 0.204) | (0.046, 0.284) |
| | p-value | | 0.1479 | 0.0066 |

Change from Baseline in Asthma Control Questionnaire

Figure 5A:
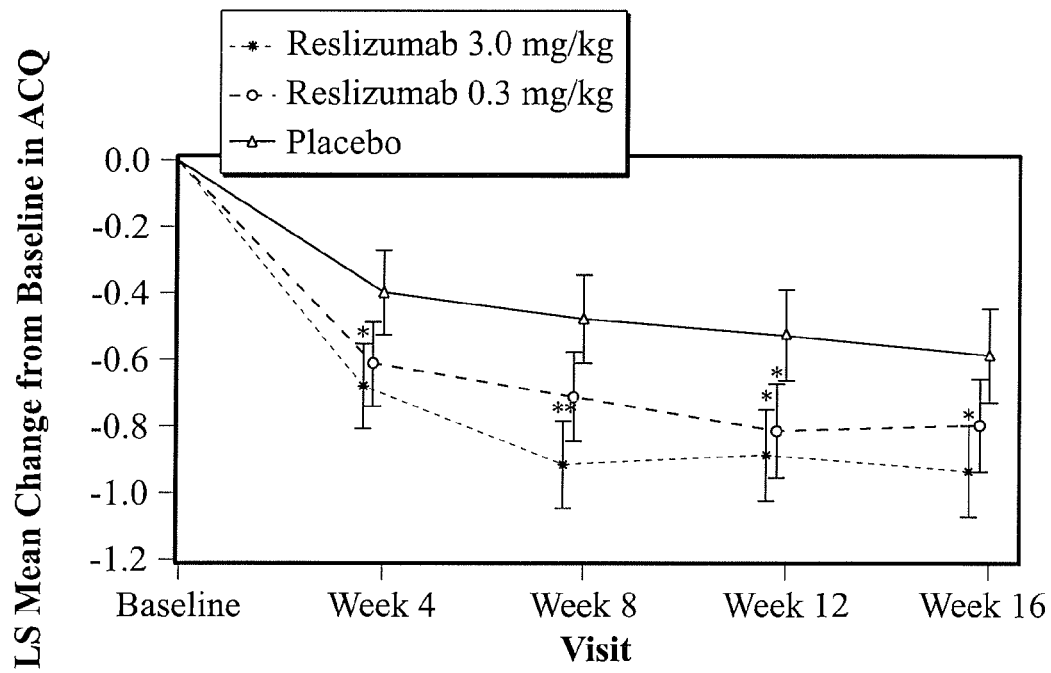
FIG. 5A and FIG. 5B represent change (SE) from baseline to each visit in asthma control questionnaire (ACQ) score by treatment group (FIG. 5A) and the overall change from baseline in ACQ scores (FIG. 5B) after 16 weeks of treatment in study 1. All inferential statistics are derived from MMRM with treatment, visit, treatment by visit interaction, age group, history of asthma exacerbation in the previous 12 months, height, baseline, sex, and patient as a random effect. Data are least-squared means±standard error. Negative changes in ACQ indicate improved asthma control. The minimal clinically important difference for ACQ is 0.5 units. Δ=treatment difference (reslizumab–placebo). * p≤0.05, ** p≤0.005 versus placebo. P values are not adjusted to control for multiplicity. Placebo=solid line; reslizumab 0.3 mg/kg=shorter hashes; reslizumab 3.0 mg/kg=longer hashes.
Figure 5B:
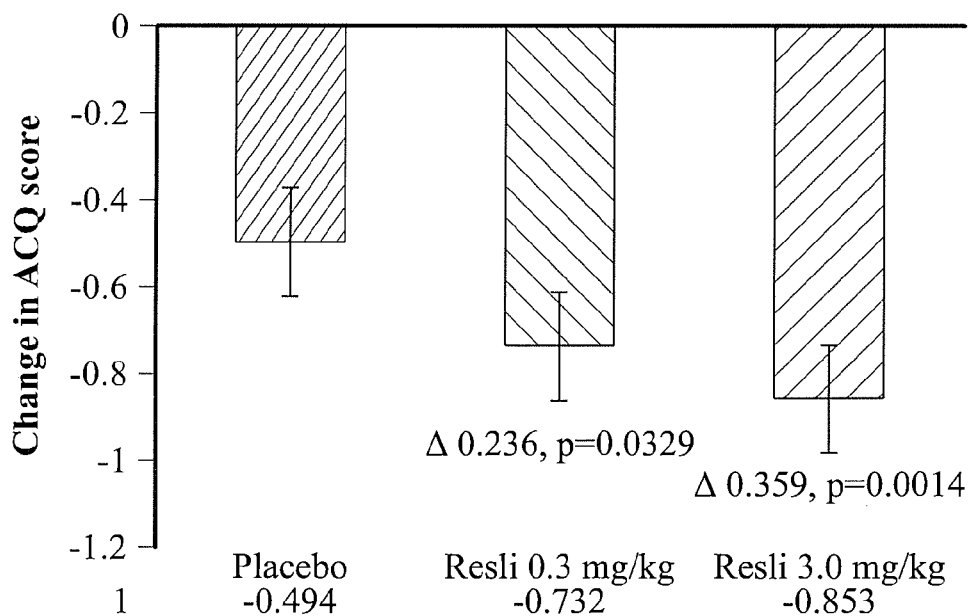

The analysis overall mean change from baseline in ACQ score over 16 weeks of treatment showed improvement (decrease) for patients in the reslizumab 0.3 mg/kg and 3.0 mg/kg treatment groups compared with placebo (−0.238 units, p=0.0329 and −0.359 units, p=0.0014, respectively) (Table 7). The treatment effect for change in ACQ from baseline to weeks 4, 8, 12, and 16 for the 0.3 mg/kg and 3.0 mg/kg reslizumab treatment groups was also analyzed (FIG. 5). Improvement in ACQ was seen after the first dose of reslizumab 3.0 mg/kg at the first scheduled 4-week assessment (p=0.0153) which was sustained throughout the 16-week treatment period. Improvements for patients in the reslizumab 0.3 mg/kg treatment group were more variable, but numerically greater than placebo at every clinic visit. Improvement in ACQ scores at 16 weeks was observed for the 3 mg/kg but not for the 0.3 mg/kg dose level (p=0.0129 and p=0.1327, respectively).

Figure 6:
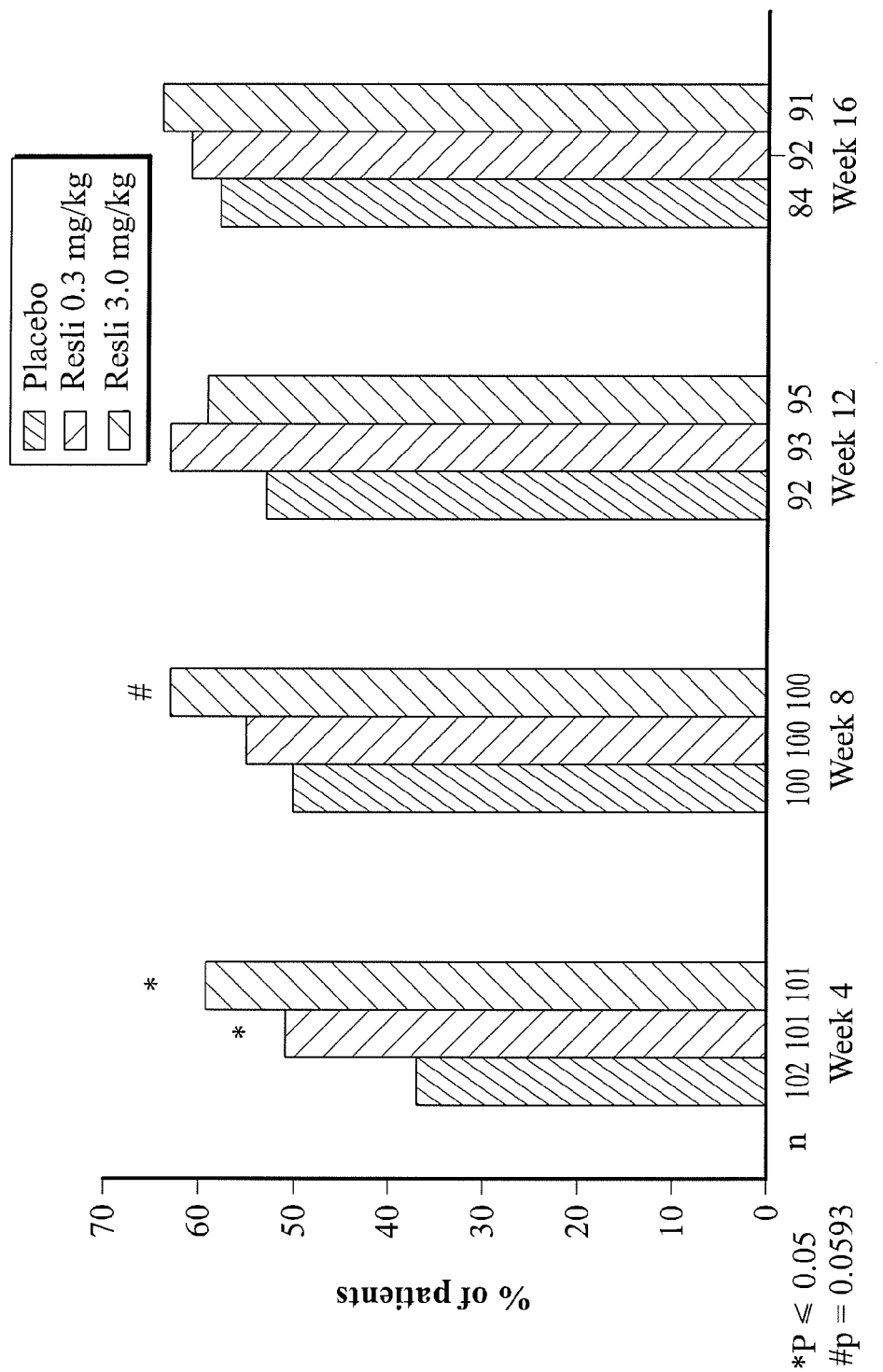
FIG. 6 represents the proportion of subjects completing study 1 and achieving minimal clinically important differences (0.5 Units) in ACQ score from baseline. * p≤0.05; # p=0.0593. P value for comparison of active and placebo groups is obtained from the CMH test stratified by age group and history of asthma exacerbation in the previous 12 months. Placebo=left bar in each group; reslizumab 0.3 mg/kg=middle bar in each group; reslizumab 3.0 mg/kg=right bar in each group.

In an analysis of subjects remaining in the trial at each visit, the proportion of subjects that achieved the minimal clinically important difference in ACQ score (0.5 units) was significantly greater with either dose of reslizumab (51-59%) compared with placebo (37%) at week 4 (FIG. 6). Numeric differences observed versus placebo at later visits were not significant, noting that placebo results improved over time as a disproportionate number of placebo subjects withdrew from the study.

TABLE 7

| Variable (unit) | Statistic | Placebo (N = 105) | Reslizumab 0.3 mg/kg (N = 103) | Reslizumab 3.0 mg/kg N = 103) |
|---|---|---|---|---|
| Baseline ACQ score | Mean | 2.471 | 2.499 | 2.591 |

TABLE 7-continued

| Variable (unit) | Statistic | Placebo (N = 105) | Reslizumab 0.3 mg/kg (N = 103) | Reslizumab 3.0 mg/kg N = 103) |
|---|---|---|---|---|
| | SD | 0.8301 | 0.8903 | 0.8861 |
| | SE of mean | 0.0810 | 0.0877 | 0.0873 |
| | Median | 2.286 | 2.429 | 2.429 |
| | Min, max | 0.857, 5.286 | 0.429, 5.000 | 0.429, 5.286 |
| Overall change | n[a] | 103 | 101 | 101 |
| | LS mean | −0.494 | −0.732 | −0.853 |
| | SE of LS mean | 0.1231 | 0.1250 | 0.1233 |
| | Treatment difference (active − placebo) | | −0.238 | −0.359 |
| | SE of difference | | 0.1108 | 0.1110 |
| | 95% CI | | (−0.456, −0.019) | (−0.577, −0.140) |
| | p-value | | 0.0329 | 0.0014 |
| Week 16 change in ACQ score | n[a] | 84 | 92 | 91 |
| | LS mean | −0.584 | −0.795 | −0.935 |
| | SE of LS mean | 0.1377 | 0.1381 | 0.1366 |
| | Treatment difference (active − placebo) | | −0.211 | −0.351 |
| | SE of difference | | 0.1399 | 0.1402 |
| | 95% CI | | (−0.487, 0.064) | (−0.627, −0.075) |
| | p-value | | 0.1327 | 0.0129 |

[a]n denotes number of patients who contributed at least once to the analysis.
SD = standard deviation; SE = standard error; min = minimum; max = maximum; LS = Least Squares; CI = confidence interval Change from Baseline to Week 16 in Asthma Quality of Life Questionnaire The AQLQ assesses the effect of reslizumab on quality of life metrics including overall activity, asthma symptoms, emotional function, and response to environmental stimuli. The AQLQ score was only assessed once during the study at week 16 or at early withdrawal if it met endpoint criteria for efficacy assessments: i.e., last post-baseline assessment if within 3 to 5 weeks of the last dose of study drug. A treatment difference was observed in AQLQ total score compared with placebo for the 3.0 mg/kg reslizumab treatment group (0.359 units, p=0.0241); (FIG. 7 and Table 8). AQLQ scores for the subdomains of asthma symptoms and emotional function scores were also improved (increased) for the reslizumab 0.3 mg/kg and 3.0 mg/kg treatment groups compared with placebo. The proportion of patients achieving at least 0.5 improvement from baseline to week 16 in AQLQ (FIG. 7B).

TABLE 8

| Variable (unit) | Statistic | Placebo (N = 105) | Reslizumab 0.3 mg/kg (N = 103) | Reslizumab 3.0 mg/kg (N = 103) |
|---|---|---|---|---|
| Baseline AQLQ total score | n | 105 | 102 | 103 |
| | Mean | 4.374 | 4.479 | 4.164 |
| | SD | 1.2047 | 1.2266 | 1.2233 |
| | SE of mean | 0.1176 | 0.1215 | 0.1205 |
| | Median | 4.531 | 4.578 | 4.250 |
| | Min, max | 1.375, 6.563 | 1.438, 6.875 | 1.156, 6.531 |
| Week 16 change in AQLQ total score | n[a] | 101 | 96 | 99 |
| | LS mean | 0.779 | 1.057 | 1.138 |
| | SE of LS mean | 0.1817 | 0.1881 | 0.1829 |
| | Treatment difference (active − placebo) | | 0.278 | 0.359 |
| | SE of difference | | 0.1591 | 0.1582 |
| | 95% CI | | (−0.036, 0.591) | (0.047, 0.670) |
| | p-value | | 0.0822 | 0.0241 |

[a]n denotes number of patients who contributed at least once to the analysis.
SD = standard deviation; SE = standard error; min = minimum; max = maximum; LS = Least Squares; CI = confidence interval.

Change from Baseline in Asthma Symptom Utility Index by Visit

The overall LS mean change from baseline in ASUI (scores range from 0 [worst possible symptoms] to 1 [no symptoms]) over the 16 weeks of treatment was improved (increased) compared with placebo for the 0.3 mg/kg (0.051 units, p=0.0094) and 3.0 mg/kg (0.047 units, p=0.0160) reslizumab treatment groups (Table 9) (FIG. 8). This indicates that the patients in the reslizumab treatment groups had less frequent and less severe asthma related symptoms than patients treated with placebo, although the overall difference did not reach the minimal important difference (MID) of the ASUI, which has recently been determined to be 0.09 (Bime et al 2012).

Improvement in asthma related symptoms was seen at the first scheduled 4 week assessment (p≤0.05) after the first dose of reslizumab 0.3 mg/kg and 3.0 mg/kg that was generally sustained throughout the 16 week treatment period (FIG. 8).

TABLE 9

| Variable (unit) | Statistic | Placebo (N = 105) | Reslizumab 0.3 mg/kg (N = 103) | Reslizumab 3.0 mg/kg (N = 103) |
|---|---|---|---|---|
| Baseline ASUI score | Mean | 0.674 | 0.675 | 0.657 |
| | SD | 0.1897 | 0.2061 | 0.1913 |
| | SE of mean | 0.0185 | 0.0203 | 0.0188 |
| | Median | 0.692 | 0.694 | 0.686 |
| | Min, max | 0.088, 1.000 | 0.128, 1.000 | 0.101, 0.982 |
| Overall change in ASUI score | n[a] | 103 | 101 | 101 |
| | LS mean | 0.082 | 0.132 | 0.129 |
| | SE of LS mean | 0.0218 | 0.0221 | 0.0218 |
| | Treatment difference (active − placebo) | | 0.051 | 0.047 |
| | SE of difference | | 0.0193 | 0.0193 |
| | 95% CI | | (0.012, 0.089) | (0.009, 0.085) |
| | p-value | | 0.0094 | 0.0160 |
| Week 16 change in ASUI score | n[a] | 84 | 93 | 91 |
| | LS mean | 0.94 | 0.134 | 0.134 |
| | SE of LS mean | 0.0250 | 0.0250 | 0.0247 |
| | Treatment difference (active − placebo) | | 0.040 | 0.040 |
| | SE of difference | | 0.0257 | 0.0258 |
| | 95% CI | | (−0.010, 0.091) | (−0.011, 0.091) |
| | p-value | | 0.1177 | 0.1215 |

[a]n denotes number of patients who contributed at least once to the analysis.

SD = standard deviation; SE = standard error; min = minimum; max = maximum; LS = Least Squares; CI = confidence interval.

Change from Baseline in Short Acting Beta Agonist (SABA) Use by Visit

During each scheduled visit, patients were asked to recall the total number of puffs of SABA they used over the 3 days prior to each scheduled clinic visit. There was an overall reduction in daily SABA use (number of puffs per day) for the 0.3 mg/kg and 3.0 mg/kg reslizumab treatment groups compared with the placebo treatment group over 16 weeks of treatment (1.0 puff/day, p=0.0119 and 0.9 puff/day, p=0.0151, respectively) (Table 10, FIG. 9). Compared to placebo treated patients, a decrease in rescue SABA requirement was observed for reslizumab treated patients by the first assessment at week 4 and was sustained through week 16.

TABLE 10

| Variable (unit) | Statistic | Placebo (N = 105) | Reslizumab 0.3 mg/kg (N = 103) | Reslizumab 3.0 mg/kg (N = 103) |
|---|---|---|---|---|
| Baseline average daily SABA use | n | 104 | 103 | 103 |
| | Mean | 2.3 | 1.9 | 2.3 |
| | SD | 2.20 | 2.45 | 2.58 |
| | SE of mean | 0.22 | 0.24 | 0.25 |
| | Median | 2.0 | 1.3 | 1.7 |
| | Min, max | 0.0, 12.0 | 0.0, 15.0 | 0.0, 13.7 |
| Overall change in average daily SABA use (#puffs/day) | n[a] | 102 | 101 | 102 |
| | LS mean | −0.3 | −1.0 | −0.9 |
| | SE of LS mean | 0.28 | 0.28 | 0.27 |
| | Treatment difference (active − placebo) | | −0.648 | −0.624 |
| | SE of difference | | 0.2559 | 0.2551 |
| | 95% CI | | (−1.152, −0.144) | (−1.126, −0.121) |
| | p-value | | 0.0119 | 0.0151 |
| Week 16 change in average daily SABA use (#puffs/day) | n[a] | 83 | 93 | 91 |
| | LS mean | −0.3 | −0.9 | −1.0 |
| | SE of LS mean | 0.31 | 0.31 | 0.30 |
| | Treatment difference (active − placebo) | | −0.648 | −0.708 |
| | SE of difference | | 0.3200 | 0.3201 |
| | 95% CI | | (−1.278, −0.017) | (−1.339, −0.077) |
| | p-value | | 0.0442 | 0.0280 |

[a] n denotes number of patients who contributed at least once to the analysis.
SD = standard deviation; SE = standard error; min = minimum; max = maximum; LS = Least Squares; CI = confidence interval.

Change from Baseline in Blood Eosinophil Count

Overall change from baseline in blood eosinophil count ($10^9$/L) over the 16 weeks of treatment showed treatment differences (reductions in blood eosinophil count) for the 0.3 mg/kg (p=0.0000) and 3.0 mg/kg (p=0.0000) reslizumab treatment groups compared with placebo, which were greatest for the 3.0 mg/kg group (Table 11, FIG. 10).

TABLE 11

| Variable (unit) | Statistic | Placebo (N = 105) | Reslizumab 0.3 mg/kg (N = 103) | Reslizumab 3.0 mg/kg (N = 103) |
|---|---|---|---|---|
| Baseline Eosinophil Count ($10^9$/L) | Mean | 0.601 | 0.644 | 0.595 |
| | SD | 0.4331 | 0.4926 | 0.3931 |
| | SE of mean | 0.0423 | 0.0485 | 0.0387 |
| | Median | 0.504 | 0.500 | 0.500 |
| | Min, max | 0.100, 3.700 | 0.100, 3.700 | 0.100, 2.300 |
| Overall change in Eosinophil Count ($10^9$/L) | n[a] | 103 | 101 | 102 |
| | LS mean | −0.035 | −0.358 | −0.529 |
| | SE of LS mean | 0.0271 | 0.0277 | 0.0270 |
| | Treatment difference (active − placebo) | | −0.323 | −0.494 |
| | SE of difference | | 0.0243 | 0.0242 |
| | 95% CI | | (−0.370, −0.275) | (−0.542, −0.447) |
| | p-value | | 0.0000 | 0.0000 |
| Week 16 change in Eosinophil Count ($10^9$/L) | n[a] | 81 | 90 | 87 |
| | LS mean | −0.078 | −0.398 | −0.538 |
| | SE of LS mean | 0.0310 | 0.0313 | 0.0308 |
| | Treatment difference (active − placebo) | | −0.320 | −0.460 |

TABLE 11-continued

| Variable (unit) | Statistic | Placebo (N = 105) | Reslizumab 0.3 mg/kg (N = 103) | Reslizumab 3.0 mg/kg (N = 103) |
|---|---|---|---|---|
| | SE of difference | | 0.0320 | 0.0322 |
| | 95% CI | | (−0.383, −0.257) | (−0.523, −0.396) |
| | p-value | | 0.0000 | 0.0000 |

[a]n denotes number of patients who contributed at least once to the analysis.
SD = standard deviation; SE = standard error; min = minimum; max = maximum; LS = Least Squares; CI = confidence interval.

Treatment differences were also observed for both the 0.3 mg/kg and 3.0 mg/kg reslizumab treatment groups compared with placebo at each independent visit (weeks 4, 8, 12, and 16) (p=0.0000, all comparisons). As the vast majority of treated patients either elected to continue on to Study C38072/3085 open label extension after completing treatment at week 16 (86%), or failed to provide follow up for other reasons, the blood eosinophil data for the 90 day follow-up visit (6, 9, and 8 patients in the placebo, 0.3 mg/kg and 3 mg/kg treatment groups, respectively), were very limited. The mean changes in blood eosinophil counts from baseline to the follow up visit were −0.197×10$^9$/L, 0.119× 10$^9$/L, and 0.133×10$^9$/L for patients in the placebo, 0.3 mg/kg reslizumab group, and 3.0 mg/kg reslizumab group, respectively. These limited data indicate that blood eosinophils in both reslizumab groups returned to baseline by the follow up visit (i.e., approximately 4 months after the last dose of reslizumab).

Biomarkers

Eosinophil cationic protein (ECP), eosinophil derived neurotoxin (EDN), and eosinophil peroxidase (EP) present in serum and plasma were characterized as potential biomarkers. ECP and EDN, indicators of eosinophilic inflammation, may aid clinicians in the diagnosis, treatment, and monitoring of their patients with asthma (Kim 2013). Serum concentrations of ECP and EDN are presented in Table 12. The EP analyses were not performed due to the unavailability of a reliable, robust method.

All available ECP and EDN data were included for evaluation and missing or invalid results were not estimated for the biomarker analyses. The biomarker analyses included only patients in the FAS who had blood samples drawn for the determination of biomarkers.

Twelve biomarker measurements obtained from 5 patients (422102, placebo; 004112 and 181102, 0.3 mg/kg reslizumab; 019136 and 504113, 3.0 mg/kg reslizumab) were excluded due to a missing date of a post screening scheduled visit.

Serum ECP and EDN levels were similar in patients in all 3 study groups at baseline. From baseline to week 16, both biomarker levels remained about the same in patients in the placebo group, decreased slightly in patients treated with 0.3 mg/kg reslizumab, and decreased the most in patients treated with 3.0 mg/kg reslizumab (Table 12). The percentage decreases in serum ECP levels from baseline to week 16 were 8.5%, 52.0%, and 74.1% in the placebo, 0.3 mg/kg reslizumab, and 3.0 mg/kg reslizumab groups, respectively. The percentage decreases in serum EDN levels from baseline to week 16 were 6.3%, 51.4%, and 73.9% in the placebo, 0.3 mg/kg reslizumab, and 3.0 mg/kg reslizumab groups, respectively. The mean changes from baseline in serum levels of ECP and EDN are represented graphically in FIG. 11A and FIG. 11B, respectively.

TABLE 12

| Assay | Time-point | Statistic | Placebo (N = 105) | Reslizumab 0.3 mg/kg (N = 103) | Reslizumab 3.0 mg/kg (N = 103) |
|---|---|---|---|---|---|
| Serum ECP (ng/mL) | Baseline | n[a] | 103 | 100 | 100 |
| | | Mean | 88.2 | 92.7 | 94.6 |
| | | SD | 98.09 | 93.27 | 114.87 |
| | | SE of mean | 9.67 | 9.33 | 11.49 |
| | | Median | 58.7 | 64.4 | 61.6 |
| | | Min, max | 4.0, 675.1 | 4.0, 728.3 | 4.1, 694.3 |
| | Week 16 | n | 93 | 94 | 94 |
| | | Mean | 80.7 | 44.5 | 24.5 |
| | | SD | 68.42 | 50.28 | 18.70 |
| | | SE of mean | 7.09 | 5.19 | 1.93 |
| | | Median | 60.7 | 27.3 | 17.3 |
| | | Min, max | 8.2, 351.6 | 1.5, 308.4 | 2.3, 110.5 |
| Serum EDN (ng/mL) | Baseline | n[a] | 103 | 100 | 100 |
| | | Mean | 89.3 | 93.9 | 97.9 |
| | | SD | 59.71 | 60.17 | 82.82 |
| | | SE of mean | 5.88 | 6.02 | 8.28 |
| | | Median | 73.2 | 81.9 | 74.6 |
| | | Min, max | 22.2, 455.4 | 26.7, 434.9 | 22.8, 593.5 |
| | Week 16 | n | 93 | 94 | 94 |
| | | Mean | 83.7 | 45.6 | 25.6 |
| | | SD | 48.31 | 32.32 | 12.87 |
| | | SE of mean | 5.01 | 3.33 | 1.33 |
| | | Median | 72.3 | 36.2 | 21.9 |
| | | Min, max | 22.2, 288.5 | 11.4, 205.7 | 7.5, 78.4 |

[a]n denotes number of patients who contributed at least once to the analysis.
SD = standard deviation; SE = standard error; min = minimum; max = maximum.

Adverse Events

The most common adverse events were asthma, headache, nasopharyngitis, upper respiratory tract infection, and sinusitis (Table 13). Serious adverse events included: acute myocardial infarction (n=1; placebo); pneumonia (n=1; reslizumab 3.0 mg/kg) occurred 11 days after the first dose of reslizumab, patient discontinued (during the 90-day follow-up in same patient: road traffic accident; rib fracture; asthma exacerbation); sinusitis (n=1; reslizumab 3.0 mg/kg); and asthma (n=2; reslizumab 3.0 mg/kg). No deaths occurred during the study.

TABLE 13

| Adverse event n (%) | Placebo n = 105 | Reslizumab 0.3 mg/kg n = 103 | Reslizumab 3.0 mg/kg n = 103 |
|---|---|---|---|
| ≥1 AE, ANY | 66 (63) | 59 (57) | 61 (59) |
| ≥1 treatment related AE | 8 (8) | 6 (6) | 12 (12) |

TABLE 13-continued

| Adverse event n (%) | Placebo n = 105 | Reslizumab 0.3 mg/kg n = 103 | Reslizumab 3.0 mg/kg n = 103 |
|---|---|---|---|
| ≥1 serious AE | 1 (<1) | 0 | 4 (4) |
| ≥1 discontinuation AE | 10 (10) | 1 (<1) | 6 (6) |
| Adverse events in >2% of subjects in any reslizumab group (preferred term) | | | |
| Asthma | 20 (19) | 6 (6) | 16 (16) |
| Headache | 6 (6) | 8 (8) | 11 (11) |
| Nasopharyngitis | 4 (4) | 6 (6) | 6 (6) |
| Upper respiratory tract infection | 3 (3) | 3 (3) | 5 (5) |
| Sinusitis | 3 (3) | 3 (3) | 4 (4) |
| Bronchitis | 5 (5) | 5 (5) | 2 (2) |
| Allergic rhinitis | 4 (4) | 4 (4) | 1 (<1) |
| Pharyngitis | 3 (3) | 3 (3) | 1 (<1) |
| Dyspnea | 1 (<1) | 1 (<1) | 4 (4) |
| Acute sinusitis | 2 (2) | 3 (3) | 1 (<1) |
| Nausea | 0 | 3 (3) | 2 (2) |
| Vomiting | 0 | 3 (3) | 0 |
| Musculoskeletal and connective tissue[1] | 4 (4) | 3 (3) | 7 (7) |
| Nervous system disorders[2] | 11 (10) | 10 (10) | 16 (16) |

[1] 3 mg/group accrued additional cases (<1% each) of arthralgia, joint stiffness, Musculoskeletal chest pain, Myalgia, and tendonitis.
[2] Primarily accounted for by additional headaches: PBO, 0.3 and 3 mg/kg at 6, 8% and 11% respectively.

The frequency of overall AEs were essentially balanced across SOCs excepting. Treatment-related AE (as assessed by investigator): the slight excess in treatment related AE seen in the reslizumab 3 mg/kg group (12%) vs. placebo (8%) was generally related to accrual of single AEs (incidence <1%) across multiple SOCs without apparent pattern. Serious AE for reslizumab all occurred in the 3 mg/kg dose; none related. Same patient: 1 each—pneumonia; road accident/rib fracture; asthma exacerbation—not related; 1 sinusitis—not related; 2 asthma exacerbation—not related. Discontinuation AEs for reslizumab included asthma (4), myalgia (1) and pneumonia (1). Conclusion: No specific safety concerns. The topline safety results for 3081 are consistent with the known safety profile for reslizumab Conclusion In subjects with elevated blood eosinophils, 4 monthly doses of reslizumab were well tolerated and associated with improvements in pulmonary function and patient-reported asthma control on top of standard-of-care therapies. Primary efficacy was met for both 0.3 mg/kg and 3 mg/kg. However, improvements were generally larger for the 3 mg/kg dose, and met statistical significance, for all clinically important metrics. Reslizumab onset of action occurred within one month across both lung function and patient-centric measures. The 3 mg/kg dose produced a greater effect on blood eosinophil lowering than the 0.3 mg/kg dose.

Example 2: Studies 2 and 3—Treatment with Placebo or Reslizumab 3.0 Mg/Kg Once Every 4 Weeks for a Total of 13 Doses (52 Weeks)

Study Drugs

Study drugs were provided as sterile solutions for infusion. Reslizumab was presented as 100 milligrams (10 milliliters) per vial, formulated at 10 milligrams per milliliter in 20 millimolar sodium acetate, 7% sucrose, and pH 5.5 buffer. Placebo was presented as 10 milliliters per vial, formulated in 20 millimolar sodium acetate, 7% sucrose, and pH 5.5 buffer. Both study drugs were added and mixed with sterile saline for infusion and then administered via an intravenous infusion line outfitted with a sterile, non-pyrogenic infusion, single-use, low-protein binding filter (0.20 to 1 micrometer in diameter). Prior to use, reslizumab and placebo were stored in a refrigerator at a controlled temperature (2° to 8° Celsius).

Inclusion and Exclusion Criteria and Patients

Two duplicate randomized, double-blind, placebo-controlled, parallel-group trials (studies 2 and 3) were conducted.

Patients enrolled in either study had to meet the following inclusion criteria:

Male or female patients aged 12 to 75 years with a previous diagnosis of asthma;

At least one asthma exacerbation requiring oral, intramuscular, or intravenous corticosteroid use for ≥3 days over the past 12 months before screening;

Current blood eosinophil level of ≥400 per microliter (at screening);

Airway reversibility of ≥12% to beta-agonist administration (airway reversibility was demonstrated by withholding long-acting beta-agonist (LABA) therapy for ≥12 hours and short-acting beta-agonist therapy (SABA) for ≥6 hours before measuring forced expiratory volume in 1 second ($FEV_1$), and then repeating the $FEV_1$ measurement after receiving SABA therapy (up to four puffs). If a patient's $FEV_1$ improved by ≥12% between the two tests, the patient was deemed as having airway reversibility. One retest was permitted during the screening period);

Asthma Control Questionnaire (ACQ) score of ≥1.5 at screening and at baseline (before the first dose of study drug);

Use of inhaled fluticasone at a dosage of ≥440 micrograms, or equivalent, daily chronic oral corticosteroid use (≤10 milligrams per day of prednisone or equivalent) was allowed. If a patient was on a stable dose (e.g. ≥2 weeks of oral corticosteroid treatment) at the time of enrollment, the patient had to remain on this dose throughout the study. The patient's baseline asthma therapy regimen (including, but not limited to, inhaled corticosteroids, oral corticosteroids [up to a maximum dose of 10 milligrams of prednisone daily or equivalent], leukotriene antagonists, 5-lipoxygenase inhibitors, or cromolyn sodium) had to be stable for 30 days prior to screening and baseline, and had to continue without dosage changes throughout the study);

All female patients had to be surgically sterile, 2 years postmenopausal, or have a negative beta-human chorionic gonadotropin (β-HCG) pregnancy test at screening (serum) and at baseline (urine);

Female patients of childbearing potential (not surgically sterile or 2 years postmenopausal) had to use a medically accepted method of contraception and agree to continued use of this method for the duration of the study and for 30 days after completing the trial (acceptable methods of contraception included the barrier method with spermicide, abstinence, an intrauterine device (IUD), and steroidal contraceptives (oral, transdermal, implanted, or injected). Partner sterility alone was not acceptable for inclusion);

Provision of written informed consent (patients aged 12 to 17 years had to provide assent);

Reasonable health (except for the diagnosis of asthma), as judged by the investigator, and as determined by a medical history, medical examination, electrocardiogram evaluation (at screening), and serum chemistry, hematology, and urinalysis;

Willing and able to understand and comply with study restrictions, requirements, and procedures, as specified by the study center, and to remain at the study center for the required duration during the study period, and be willing to return to the center for the follow-up evaluation as specified in the protocol; and Patients who experienced an asthma exacerbation during the screening period were considered to have failed screening and were not randomized to study treatment (patients could only be rescreened once).

Patients who met any of the following criteria were excluded from the studies: Any clinically meaningful comorbidity that could interfere with the study schedule or procedures, or compromise safety; Known hypereosinophilic syndrome; Another confounding underlying lung disorder (e.g. chronic obstructive pulmonary disease, pulmonary fibrosis, or lung cancer) (Patients with pulmonary conditions with symptoms of asthma and blood eosinophilia (e.g. Churg-Strauss syndrome or allergic bronchopulmonary aspergillosis) were excluded); Current smoker (i.e. had smoked within the last 6 months prior to screening); Current use of systemic immunosuppressive, immunomodulating, or other biologic agents (including, but not limited to, anti-immunoglobulin E monoclonal antibodies, methotrexate, cyclosporine, interferon-a, or anti-tumor necrosis factor [anti-TNF] monoclonal antibodies) within 6 months prior to screening; Prior use of an anti-human interleukin-5 monoclonal antibody (e.g. reslizumab, mepolizumab, or benralizumab); Any inadequately controlled, aggravating medical factors (e.g. rhinitis, gastro-esophageal reflux disease, or uncontrolled diabetes); Participation in any investigative drug or device study within 30 days prior to screening, or any investigative biologics study within 6 months prior to screening; Female patients who were pregnant, nursing, or, if of childbearing potential, not using a medically accepted effective method of birth control (e.g. barrier method with spermicide, abstinence, IUD, or steroidal contraceptive [oral, transdermal, implanted, or injected]); Concurrent infection or disease that prevented assessment of active asthma; History of concurrent immunodeficiency (human immunodeficiency virus [HIV], acquired immunodeficiency syndrome [AIDS], or congenital immunodeficiency); Current suspected drug and alcohol abuse, as specified in the Diagnostic and Statistical Manual of Mental Disorders, Fourth Edition, Text Revision (DSM-IV-TR); Active parasitic infection within 6 months prior to screening; Receipt of any live attenuated vaccine within the 12-week period prior to screening; History of allergic reactions to or hypersensitivity to any component of the study drug; An infection within 4 weeks prior to screening or during the screening period necessitating admission to hospital for ≥24 hours, or treatment with intravenous or oral antibiotics; History of exposure to water-borne parasites within 6 weeks prior to screening or during the screening period, or a history of diarrheal illness of undetermined etiology within 3 months prior to screening or during the screening period; and Requirement for treatment for an asthma exacerbation within 4 weeks of screening or during the screening period.

Treatment

Patients were stratified by regular maintenance oral corticosteroid use at enrollment (yes' versus 'no') and by region (United States' versus 'Other'), and randomized 1:1 to receive an intravenous infusion of reslizumab 3 mg/kg or matching placebo, every 4 weeks (13 doses; last dose on week 48). Randomization was performed using interactive response technology with computerized central randomization. Study drugs (discussed above) were provided by the sponsor. Patients were required to continue their usual asthma treatment, including but not limited to, long-acting beta agonists (LABA), inhaled corticosteroids (ICS), OCS (≤10 mg per day of prednisone or equivalent), leukotriene modifiers, and cromolyn sodium, at constant doses. Treatments were required to be stable for 30 days prior to screening.

Endpoints and Assessments

The efficacy, safety and immunogenicity of reslizumab treatment for adolescent and adult patients with eosinophilic asthma whose symptoms are inadequately controlled with inhaled corticosteroids were evaluated. Primary efficacy was determined by the annual frequency of clinical asthma exacerbations (CAE), with events adjudicated by an independent review committee. CAE were defined as worsening of asthma resulting in use of systemic corticosteroids in patients not already receiving treatment, or a two-fold increase in the dose of either ICS or systemic corticosteroids for ≥3 days, and/or the need for asthma-related emergency treatment (emergency room visit, hospitalization, or unscheduled physician's office visit for nebulizer or other urgent treatment). The per protocol definition of exacerbations were that they were required to be associated with ≥1 of the following: decrease in $FEV_1$ of ≥20% from baseline; reduction in peak expiratory flow rate by ≥30% from baseline on 2 consecutive days; or worsening signs or symptoms per physician evaluation. Patients experiencing an exacerbation could continue in the study after receiving appropriate medical therapy, unless otherwise decided by the principal investigator.

Secondary efficacy determinations included lung function (Forced Expiratory Volume in 1 second ($FEV_1$), Asthma Quality of Life Questionnaire (AQLQ) total score, Asthma Control Questionnaire (ACQ-7) score, Asthma Symptom Utility Index (ASUI) score, time to first CAE, rescue use of short-acting beta-agonist (SABA), blood eosinophil count, Forced Vital Capacity (FVC), and Forced Expiratory Flow Rate ($FEF_{25\%-75\%}$)). SABA use was based on patient recall of treatment used in the 3 days prior to each visit. Blood eosinophil counts were measured using a standard complete blood count with differential blood test: the results of the differential were redacted after initiation of treatment to ensure the integrity of the double blinding was maintained. Additional secondary endpoints included safety (based on assessment of adverse events, laboratory tests, vital signs, electrocardiography, physical examinations, and concomitant medication use) and immunogenicity.

Prebronchodilator spirometry, ASUI and ACQ scores, SABA use, blood eosinophil count, and safety parameters were assessed every 4 weeks. AQLQ score was evaluated at baseline, and at weeks 16, 32, and 52/early withdrawal. Anti-reslizumab antibodies were measured at weeks 16, 32, and 52/early withdrawal, and also in any patient experiencing a serious adverse event, adverse event leading to discontinuation, or clinical asthma exacerbation.

Statistical Analyses

Efficacy endpoints were evaluated in the intention-to-treat population (all randomized patients) and safety endpoints were assessed in the safety population (all patients receiving ≥1 dose of study medication). Exacerbation frequency (primary endpoint) was analyzed using a negative binomial regression model, including treatment arm and randomization stratification factors as model factors, and logarithm of follow-up time excluding the summed duration of exacerbations in the treatment period as an offset variable. Rate ratios versus placebo and 95% confidence intervals (CI) were estimated from the model. Likelihood-based Chi-square tests (two-sided, α=0.05) were used to test for between-group differences. The analysis for secondary efficacy variables was prespecified for the 16 week time point for analysis of $FEV_1$ and for overall effect at 16 weeks for lung function, patient-reported asthma outcomes, SABA use, blood eosinophil counts, time to first CAE and CAE requiring use of systemic corticosteroids. Type I error was only controlled for at these predefined secondary time points. An analysis of covariance model was used to compare least-squares mean changes from baseline to end-of-treatment endpoint for the above outcomes. A stratified Cochran-Mantel-Haenszel test was used to analyze the proportion of patients achieving a ≥0.5-point improvement from baseline in AQLQ total score and a ≥0.5-point reduction in ACQ score. These changes represent minimal clinically important differences. Pooled data was used to perform sub-group analyses (Table 19) for CAE and $FEV_1$ analysis.
Baseline Demographics and Baseline Disease State Characteristics in the Randomized Patient Population Overall, 489 patients were randomized to reslizumab (n=245) or placebo (n=244) in Study 2, and 464 were randomized to reslizumab (n=232) or placebo (n=232) in Study 3 (intention-to-treat populations). All except one patient in the placebo arm in Study 2 received assigned study treatment; this patient was excluded from the safety analyses.

The baseline demographics and baseline disease state characteristics in the randomized patient populations for studies 2 and 3 are summarized in Table 14 below.

In each trial, baseline demographic characteristics were well balanced between the reslizumab and placebo arms. Baseline characteristics were also generally well balanced across the studies, except for numerical differences in race, oral corticosteroid use, and $FEV_1$. Baseline eosinophil counts were similar in both trials (660 and 649 cells/µl for Study 2 and 3 respectively). In Study 2, 85% of all randomized patients (placebo 84%, reslizumab 85%) received all 13 doses of study medication; in Study 3, 83% of patients (placebo 83%, reslizumab 82%) received all planned doses. The majority of patients in both trials were receiving a LABA (86% Study 2; 82% Study 3).

TABLE 14

|  | Study 2 | | Study 3 | |
| --- | --- | --- | --- | --- |
| Parameter | Placebo (n = 244) | Reslizumab (n = 245) | Placebo (n = 232) | Reslizumab (n = 232) |
| Median age (range)—yr | 49 (12-75) | 48 (12-76) | 48 (12-73) | 48 (12-74) |
| Subgroup—no. (%) | | | | |
| Male—no. (%) | 83 (34) | 103 (42) | 82 (35) | 88 (38) |
| Race—no. (%) | | | | |
| White | 182 (75) | 173 (71) | 169 (73) | 168 (72) |
| Black | 20 (8) | 14 (6) | 4 (2) | 6 (3) |
| Asian | 33 (14) | 50 (20) | 21 (9) | 16 (7) |
| Other | 9 (4) | 8 (3) | 38 (16) | 42 (18) |
| Body mass index—kilogram per square meter | 28.0 ± 6.2 | 27.7 ± 6.3 | 27.0 ± 5.1 | 27.0 ± 5.3 |
| Time since diagnosis—yr | 18.8 ± 14.2 | 19.7 ± 15.2 | 18.7 ± 13.3 | 18.2 ± 14.4 |
| All (mean) ICS use at enrollment—micrograms† | 847.7 ± 442.13 | 824.1 ± 380.28 | 756.9 ± 274.23 | 856.0 ± 588.40 |
| Oral corticosteroid use‡ | | | | |
| Use at enrollment—no. (%) | 46 (19) | 46 (19) | 27 (12) | 27 (12) |
| LABA use at enrollment—no. (%) | 207 (85) | 214 (87) | 192 (83) | 190 (82) |
| $FEV_1$ | | | | |
| Prebronchodilation—liters | 1.93 ± 0.80 | 1.89 ± 0.73 | 2.00 ± 0.67 | 2.13 ± 0.78 |
| Percent predicted value prebronchodilation | 65.0 ± 19.8 | 63.6 ± 18.6 | 68.0 ± 18.9 | 70.4 ± 21.0 |
| Reversibility—% | 26.3 ± 18.1 | 26.1 ± 15.5 | 28.7 ± 23.8 | 28.1 ± 16.1 |
| FVC—liters | 3.02 ± 1.13 | 2.96 ± 0.96 | 3.00 ± 0.91 | 3.19 ± 1.05 |
| AQLQ total score§ | 4.16 ± 1.09 | 4.30 ± 1.12 | 4.22 ± 1.08 | 4.35 ± 1.02 |
| ACQ score¶ | 2.76 ± 0.88 | 2.66 ± 0.85 | 2.61 ± 0.79 | 2.57 ± 0.89 |
| ASUI score** | 0.61 ± 0.20 | 0.63 ± 0.19 | 0.65 ± 0.19 | 0.66 ± 0.20 |
| SABA use in past 3 days | | | | |
| no. (%) | 188 (77) | 170 (69) | 181 (78) | 182 (78) |
| Puffs per day | 2.7 ± 3.2 | 2.4 ± 2.8 | 2.7 ± 2.4 | 2.9 ± 2.8 |

TABLE 14-continued

| Parameter | Study 2 | | Study 3 | |
|---|---|---|---|---|
| | Placebo (n = 244) | Reslizumab (n = 245) | Placebo (n = 232) | Reslizumab (n = 232) |
| Mean blood eosinophil count, SD—cells per microliter | 624 ± 590 | 696 ± 768 | 688 ± 682 | 610 ± 412 |
| CAEs in past 12 months—no./patient†† | 2.1 ± 2.3 | 1.9 ± 1.6 | 2.0 ± 1.8 | 1.9 ± 1.6 |

*Plus-minus values are given as means ± standard deviation.
†Fluticasone propionate or equivalent at screening visit.
‡Prednisone equivalent at screening visit.
§Asthma Quality of Life Questionnaire total and domain scores range from 1 to 7, with higher scores indicating better quality of life; a change of 0.5 points represents the minimal clinically important difference.
¶The Asthma Control Questionnaire score ranges from 0 to 6, with higher scores indicating worse control; a change of 0.5 points represents the minimal clinically important difference (Id.).
**The Asthma Symptom Utility Index summary score ranges from 0 to 1, with lower scores indicating worse symptoms; a change of 0.09 points represents the minimal clinically important difference.
††CAEs were defined as worsening of asthma requiring use of systemic corticosteroids (if not already receiving treatment) or a two-fold increase in the dose of inhaled or systemic corticosteroids for ≥3 days, and/or the need for asthma-related emergency treatment (emergency room visit, hospitalization, or unscheduled physician's office visit for nebulizer or other urgent treatment).

Efficacy

Reslizumab was associated with 50% (Study 2, CAE rate ratio of 0.90 versus 1.80; CI 0.37-0.67) and 59% (Study 3, 0.86 versus 2.11; CI 0.28-0.59) reductions in the adjudicated clinical asthma exacerbation rate compared with placebo over 52 weeks (both P<0.0001; primary endpoints) (Table 15). Reduction in CAEs defined by use of systemic corticosteroid for ≥3 days (the majority subgroup in both studies) was consistent with the primary efficacy result (Study 2, 55% reduction [0.72 (CI 0.53-0.99) versus 1.60 (CI 1.20-2.15)]; Study 3, 61% reduction [0.65 (CI 0.40-1.05) versus 1.66 (CI 1.00-2.74)]. No significant differences were observed between arms in terms of patients requiring hospitalization or emergency department treatment.

Time to first exacerbation was significantly longer following reslizumab treatment compared with placebo (FIG. 12). The probability of not experiencing an exacerbation by week 52 was 44% (CI 38, 51) with placebo and 61% (CI 55, 67) with reslizumab and 52% (CI 45.0, 58) and 73% (CI 66.8, 78.6), in Studies 2 and 3, respectively.

Pooled sub-analyses indicated that background (placebo) asthma exacerbation rates were influenced by disease severity based on background medication (1.63, 1.84, and 2.04 events per patient per year for ICS, ICS plus a LABA, and OCS-dependent categories, respectively); patients receiving reslizumab achieved better exacerbation rate-ratios versus placebo regardless of the treatment they were receiving at baseline (FIG. 12C; Table 16).

In both trials, improvement in $FEV_1$ was evident for reslizumab versus placebo by the first on-treatment assessment at Week 4 with meaningful improvements observed at 16 and 52 weeks (Table 15; FIG. 13). The results of studies 2 and 3 confirm the 16 week improvements in lung function seen for study 1. Furthermore, studies 2 and 3 demonstrate that lung function improvements are sustained through week 52.

Reslizumab treatment also resulted in marked improvements versus placebo in AQLQ total score, ACQ score, and ASUI score (Table 15). Improvements were also seen as early as the first on-treatment assessment (Week 4 for ACQ and ASUI; Week 16 for AQLQ) and overall effect vs placebo was demonstrated over the 16 and 52-week treatment periods (Table 15; FIG. 13; FIG. 14; FIG. 15). The proportion of patients with a ≥0.5-point improvement from baseline to end-of-treatment in AQLQ total score was higher in the reslizumab arms versus the placebo arms (Study 2: 74% versus 65%, P=0.03; Study 3: 73% versus 62%, P=0.02). Similarly, the proportion of patients achieving a ≥0.5-point reduction from baseline to end-of-treatment in ACQ score was significantly higher in the reslizumab arms (Study 2: 76% versus 63%, P≤0.002; Study 3: 77% versus 61%, P<0.002). Change in SABA use was not significantly different between arms (Table 15; FIG. 13).

Reslizumab was associated with a reduction in blood eosinophil counts compared with placebo (Table 15), which was apparent by the first on-treatment assessment at week 4 and sustained for the duration of the studies (FIG. 16).

Pooled sub-analyses demonstrated a trend for increasing $FEV_1$ improvement with increasing disease severity based on background medication, which was most evident at 52 weeks (0.081 L, 0.113 L and 0.151 L for ICS, ICS/LABA and OCS-dependent patients, respectively). (FIG. 17; Table 16).

TABLE 15

| Primary endpoint | Study 2 | | | Study 3 | | |
|---|---|---|---|---|---|---|
| | Placebo | Reslizumab | Rate ratio (95% CI)† | Placebo | Reslizumab | Rate ratio (95% CI)† |
| Number of patients with at least 1 CAE—n(%) | 132 (54.1%) | 92 (37.6%) | | 105 (45.3%) | 59 (25.4%) | |
| | | | Adjudicated CAE rate | | | |
| All episodes | 1.80 | 0.90 | 0.50 (0.37, 0.67)*** | 2.11 | 0.86 | 0.41 (0.28, 0.59)*** |

TABLE 15-continued

| | | | | | | |
|---|---|---|---|---|---|---|
| Episodes requiring systemic corticosteroids for ≥3 days | 1.60 | 0.72 | 0.45 (0.33, 0.62)*** | 1.66 | 0.65 | 0.39 (0.26, 0.58)*** |
| Episodes requiring hospitalization or ER treatment | 0.21 | 0.14 | 0.66 (0.32, 1.36) | 0.05 | 0.03 | 0.69 (0.29, 1.65) |

| Secondary endpoints‡ | Placebo | Reslizumab | Δ (95% CI)§ | Placebo | Reslizumab | Δ (95% CI)§ |
|---|---|---|---|---|---|---|
| Change in $FEV_1$ - liters | | | | | | |
| Week 16 | 0.110 | 0.248 | 0.137 (0.08, 0.198)*** | 0.094 | 0.187 | 0.093 (0.003, 0.155)** |
| Week 52 | 0.109 | 0.235 | 0.126 (0.06, 0.188)*** | 0.111 | 0.201 | 0.090 (0.003, 0.153)** |
| Change in AQLQ total score | | | | | | |
| Week 16[footnote] | | | | | | |
| Week 52 | 0.79 | 1.09 | 0.30 (0.14, 0.47)*** | 0.89 | 1.12 | 0.23 (0.07, 0.40)** |
| Change in ACQ score | | | | | | |
| Week 16 | −0.68 | −0.94 | −0.27 (−0.40, −0.13)*** | −0.66 | −0.86 | −0.20 (−0.33, −0.07)** |
| Week 52 | −0.76 | −1.02 | −0.26 (−0.39, −0.12)*** | −0.80 | −1.04 | −0.24 (−0.37, −0.11)*** |
| Change in ASUI score | | | | | | |
| Week 16 | 0.11 | 0.17 | 0.06 (0.03, 0.08)*** | 0.08 | 0.12 | 0.04 (0.01, 0.06)** |
| Week 52 | 0.13 | 0.19 | 0.06 (0.04, 0.08)*** | 0.11 | 0.15 | 0.04 (0.01, 0.06)** |
| Change in SABA use—puffs per day | | | | | | |
| Week 16 | −0.36 | −0.64 | −0.28 (−0.60, 0.05) | −0.44 | −0.50 | −0.06 (−0.41, 0.29) |
| Week 52 | −0.42 | −0.58 | −0.15 (−0.47, 0.16) | −0.55 | −0.73 | −0.18 (−0.50, 0.14) |
| Change in blood eosinophil count—cells per microliter | | | | | | |
| Week 16 | −118 | −584 | −466 (−5 14, −418)*** | −76 | −555 | −479 (−519, −439)*** |
| Week 52 | −127 | −582 | .455 (.491, .419)*** | −76 | −565 | −489 (−525, −453)*** |

*P ≤ 0.05,
**P ≤ 0.01,
***P ≤ 0.001.
††The rate ratio represents the ratio of adjudicated CAE rates between the reslizumab and placebo arms.
‡Values shown are least-squares mean changes over the specified period from baseline, except for the week 16 AQLQ that represents the change to week 16.
Week 16 was the first time point where AQLQ was assessed.
§The between-group difference is the absolute reduction in the reslizumab arm versus the placebo arm.

TABLE 16

Sub-population analysis (pooled Study 2 and Study 3 results)

| | Placebo (n) | | Reslizumab | | Rate ratio |
|---|---|---|---|---|---|
| | n | result | n | result | (95% CI)† |
| Adjudicated CAE rate | | | | | |
| ALL patients | 476 | 1.8118 | 477 | 0.8359 | 0.4613 (0.37, 0.58)*** |
| LABA YES | 383 | 1.84 | 397 | 0.83 | 0.45 (0.35, 0.58) |
| LABA NO | 93 | 1.63 | 80 | 0.84 | 0.51 (0.29, 0.89) |
| OCS dependent YES | 73 | 2.04 | 404 | 0.69 | 0.32 (0.18, 0.55) |
| $FEV_1$‡ | | | | | Δ (95% CI)§ |
| Overall change in $FEV_1$ ALL patients (L) | | | | | |
| Week 16 | 468 | 0.109 | 473 | 0.226 | 0.117 (0.073, 0.160)*** |
| Week 52 | | 0.115 | | 0.224 | 0.110 (0.066, 0.154)*** |

TABLE 16-continued

| | Sub- population analysis (pooled Study 2 and Study 3 results) | | | | |
|---|---|---|---|---|---|
| | Placebo (n) | | Reslizumab | | Rate ratio |
| | n | result | n | result | (95% CI)† |
| LABA NO patients | | | | | |
| Week 16 | 92 | 0.148 | 78 | 0.241 | 0.093 (−0.001, 0.188) |
| Week 52 | | 0.140 | | 0.221 | 0.081 (−0.020, 0.182) |
| LABA YES patients | | | | | |
| Week 16 | 376 | 0.109 | 395 | 0.230 | 0.120 (0.071, 0.169) |
| Week 52 | | 0.114 | | 0.227 | 0.113 (0.063, 0.162) |
| OCS YES patients | | | | | |
| Week 16 | 70 | 0.246 | 72 | 0.375 | 0.129 (−0.005, 0.263) |
| Week 52 | | 0.255 | | 0.406 | 0.151 (0.016, 0.286) |

*$P \leq 0.05$,
**$P \leq 0.01$,
***$P \leq 0.001$.
p-value were only calculated only for the entire population: it was not calculated for subgroup analyses.
†The rate ratio represents the ratio of adjudicated CAE rates between the reslizumab and placebo arms.
‡Values shown are least-square mean changes from baseline.
§The between-group difference is the absolute reduction in the reslizumab arm versus the placebo arm.

TABLE 17

| | $\Delta FEV_1$: Reslizumab 3 mg/kg − Placebo (Liters) | | | |
|---|---|---|---|---|
| | Overall change | | Change to time point | |
| Study | 16 weeks | 52 weeks | 16 weeks | 52 weeks |
| Study 2 | 0.137 (p < .0001) | 0.126 (p < .0001) | 0.072 (p = 0.0483) | 0.145 (p = 0.0004) |
| Study 3 | 0.093 (p = 0.0037) | 0.090 (p = 0.0057) | 0.101 (p = 0.0109) | 0.123 (p = 0.0016) |
| Study 1* | 0.160 (p = 0.0018) | — | 0.165 (p = 0.018) | — |

Overall change takes into consideration all time points up to 16 or 52 weeks

Influence of Disease Severity (Based on Background Controller Medication) on Reslizumab Efficacy As illustrated in FIGS. 21A and 21B, subjects who commenced reslizumab treatment with a high dosage of inhaled corticosteroids (those subjects requiring a higher steroid dosage to maintain control before treatment with reslizumab) benefited more from reslizumab treatment than those who were on a medium dosage of inhaled corticosteroids. "ICS," "ICS medium," and "ICS high" as used in FIGS. 21A and 21B encompasses all six of the ICSs in Table 18. The definition of medium and high ICS dose are provided in Table 18.

TABLE 18

| | ICS cutoffs for subgroup analysis | | |
|---|---|---|---|
| | Total Daily dose (mcg) | | |
| | Low/Medium ICS | High ICS (GINA/NAEPP) | High[e] (ATS/ERS severe asthma guidance) |
| Fluticasone[a] | ≤500 | >500 | ≥1000 |
| Mometasone[b] | ≤440 | >440 | >800 |
| Budesonide[c] | ≤800 | >800 | ≥1600 |
| Ciclesonide | ≤320 | >320 | ≥320 |
| Beclomethasone[d] | ≤400 | >400 | ≥1000 |
| Triamcinolone | ≤2000 | >2000 | ≥2000 |

ICS (inhaled corticosteroid); ATS/ERS (American Thoracic Society/European Respiratory Society); GINA/NAEPP (Global Initiative on Asthma/National Asthma Education and Prevention Program)

[a]Although fluticasone HFA MDI has a cutoff of 440 mcg and fluticasone DPI has a cutoff of 500 mcg, we selected the higher cutoff of 500 mcg to prevent medium doses from being counted in the high group.

[b]Mometasone had cutoffs of 400 mcg in NAEPP and 440 mcg in GINA. Asmanex dosed as 110 mcg or 220 mcg, so the 440 mcg cutoff makes more sense.

[c]Budesonide, of note: Symbicort low dose is 80 mcg 2 puffs BID = 320 mcg and high dose is 160 mcg 2 puffs BID = 640 mcg, but 800 is the cutoff in both GINA and NAEPP so left it in the table.

[d]Beclomethasone CFC appears to have been discontinued. Beclomethasone HFA was 480 mcg in NAEPP and 400 mcg in GINA. Easyhaler and Clenil are usually 200 mcg per dose and Qvar high starting dose is 160 mcg BID, so a cutoff of 400 mcg seems reasonable.

[e]The latest table from International ERS/ATS guidelines on definition, evaluation and treatment of severe asthma 2014 (Chung, K.F., et al. "International ERS/ATS guidelines on definition, evaluation and treatment of severe asthma." Eur Respir J (2014) 43: 343-373; table 4 - reproduced below).

| Definition of high daily dose of various inhaled corticosteroids in relation to patient age | | |
|---|---|---|
| | Threshold daily dose in mg considered as high | |
| Inhaled corticosteroid | Age 6-12 years | Age >12 years |
| Beclomethasone dipropionate | ≥800 (DPI or CFC MDI) ≥320 (HFA MDI) | ≥2000 (DPI or CFC MDI) ≥1000 (HFA MDI) |
| Budesonide | ≥800 (MDI or DPI) | ≥1600 (MDI or DPI) |
| Ciclesonide | ≥160 (HFA MDI) | ≥320 (HFA MDI) |
| Fluticasone propionate | ≥500 (HFA MDI or DPI) | ≥1000 (HFA MDI or DPI) |

-continued

Definition of high daily dose of various inhaled corticosteroids in relation to patient age

| Inhaled corticosteroid | Threshold daily dose in mg considered as high | |
|---|---|---|
| | Age 6-12 years | Age >12 years |
| Mometasone furcate | ≥500 (DPI) | ≥800 (DPI) |
| Triamcinolone acetonide | ≥1200 | ≥2000 |

Notes:
1) Designation of high doses is provided from manufacturers' recommendations where possible.
2) As chlorofluorocarbon (CFC) preparations are being taken from the market, medication inserts for hydrofluoroalkane (HFA) preparations should be carefully reviewed by the clinician for the equivalent correct dosage.
DPI: dry powder inhaler;
MDI: metered-dose inhaler Safety Profile The most commonly reported adverse events (>5%) in either study were asthma, nasopharyngitis, upper respiratory tract infections, sinusitis, influenza and headache. Of note, asthma worsenings were of special interest and were reported as adverse events, per protocol. The frequency of serious adverse events for placebo versus reslizumab in Studies 2 and 3 were 14% versus 10% and 10% versus 8%, respectively. The most common serious adverse event was worsening of asthma. Discontinuation adverse event frequency for Studies 2 and 3 for placebo versus reslizumab were 3% and 2% and 4% versus 3%, respectively. Infections were equally balanced between patients receiving placebo or reslizumab and no helminthic infestations were reported.

Two patients in the reslizumab arm in Study 3 experienced anaphylactic reactions that responded to standard therapy at the study site. There were no serious infusion reactions. Malignant neoplasms were uncommon in placebo (Study 2: colon cancer (n=1) and bladder cancer (n=1); Study 3: none) and in reslizumab groups (Study 2: lung cancer (n=2) and prostate cancer (n=1); Study 3: plasmacytoma (n=1)). One placebo-treated patient in Study 2 died from multiple-drug intoxication.

TABLE 19

| | Study 2 | | Study 3 | |
|---|---|---|---|---|
| AE—no. (%) | Placebo (n = 243) | Reslizumab (n = 245) | Placebo (n = 232) | Reslizumab (n = 232) |
| All-grade AEs | 206 (85) | 197 (80) | 201 (87) | 177 (76) |
| Asthma | 127 (52) | 97 (40) | 119 (51) | 67 (29) |
| Upper respiratory tract infection | 32 (13) | 39 (16) | 16 (7) | 8 (3) |
| Nasopharyngitis | 33 (14) | 28 (11) | 56 (24) | 45 (19) |
| Sinusitis | 29 (12) | 21 (9) | 10 (4) | 9 (4) |
| Headache | 30 (12) | 19 (8) | 17 (7) | 33 (14) |
| Influenza | 23 (9) | 18 (7) | 7 (3) | 6 (3) |
| Nausea | 10 (4) | 12 (5) | 3 (1) | 2 (<1) |
| Bronchitis | 24 (10) | 13 (5) | 14 (6) | 2 (<1) |
| Urinary tract infection | 11 (5) | 13 (5) | 1 (<1) | 0 |
| Allergic rhinitis | 6 (2) | 13 (5) | 10 (4) | 6 (3) |
| Oropharyngeal pain | 8 (3) | 13 (5) | 3 (1) | 5 (2) |
| Back pain | 13 (5) | 13 (5) | 8 (3) | 12 (5) |
| Pharyngitis | 13 (5) | 10 (4) | 8 (3) | 7 (3) |
| Cough | 13 (5) | 11 (4) | 7 (3) | 3 (1) |
| Dyspnea | 12 (5) | 10 (4) | 5 (2) | 2 (<1) |
| Respiratory tract infection | 5 (2) | 6 (3) | 8 (3) | 9 (4) |
| Dizziness | 13 (5) | 5 (2) | 4 (2) | 6 (3) |
| Serious AEs | 34 (14) | 24 (10) | 23 (10) | 18 (8) |
| Asthma | 13 (5) | 11 (4) | 6 (3) | 3 (1) |
| Pneumonia | 0 | 2 (<1) | 6 (3) | 2 (<1) |

TABLE 19-continued

| | Study 2 | | Study 3 | |
|---|---|---|---|---|
| AE—no. (%) | Placebo (n = 243) | Reslizumab (n = 245) | Placebo (n = 232) | Reslizumab (n = 232) |
| Road traffic accident | 0 | 0 | 3 (1) | 1 (<1) |
| AEs leading to discontinuation | 8 (3) | 4 (2) | 9 (4) | 8 (3) |
| Deaths | 1 (<1) | 0 | 0 | 0 |

*The safety set included all randomized patients who received at least one dose of any study drug. AEs which occurred in ≥5% of patients in any arm during the study treatment period are listed, as are serious AEs which occurred in ≥1% of patients in any arm. Incidence is based on the number of patients experiencing at least one AE.

AEs of special interest are summarized below.
- Hypersensitivity/anaphylaxis remains a known risk: incidence <1%. In study 3, 2 events reported as serious and resulting in d/c.
- Malignancy: In study 2, 1 prostate and 2 lung cancer were observed. The short latency tends to go against relatedness. In study 3, 1 case of plasmacytoma was observed.
- Infection: No specific concern, no helminthic infestations reported.
- Administration site AE: similar to placebo.
- Infusion reactions: no serious events apparent. Investigator CRF re infusion relatedness—pending.

Immunogenicity

The incidence of a positive anti-drug antibody response in the reslizumab treatment groups for Study 2 and Study 3 was 2% and 5% at baseline (prior to reslizumab administration), with ≥1 positive response during the treatment period observed in 3% and 7%, respectively. The majority positive ADA responses were low titer and transient (most being single observations that resolved). The safety profile of anti-drug antibodies (ADA) positive patients was not different from that observed in the overall population.

Conclusions

These twin studies consistently demonstrated that reslizumab significantly improved outcomes in patients with inadequately controlled asthma and blood eosinophils ≥400/µl. These results were achieved despite the continued use of prior therapies throughout. In the primary analysis reslizumab significantly reduced the annual rate of clinical asthma exacerbations by 50-59% compared with placebo. Time to first clinical asthma exacerbation was also increased with reslizumab versus placebo.

Both study 2 and 3 met both the primary and key secondary end points of reduction in the annual rate of CAE and improvement in lung function ($FEV_1$). The safety profile of reslizumab supports a favorable benefit-risk profile in patients with moderate to severe eosinophilic asthma whose symptoms are inadequately controlled with an ICS±another controller.

Common AEs consistent with those expected in a moderate to severe asthma population and generally similar to placebo. Severe and discontinuation AEs overall similar profile to placebo. Laboratory, ECG, vital signs and physical exam overall similar to placebo in study 1 (these data are pending for studies 2 and 3). AEs of special interest include: hypersensitivity/anaphylaxis remains a known risk—incidence<1%; malignant neoplasms for the program slightly more common on reslizumab than placebo (diverse origin/commonly occurring; not statistically different from all cancers in the Surveillance, Epidemiology, and End Result (SEER) data base June 2014); infection profile similar to placebo, no specific concerns; administration site/infusion reactions profile similar to placebo in study 1 (full analysis of 2 and 3 data is pending).

Example 3: Study 4—Characterize the Efficacy of Reslizumab (3.0 Mg/Kg) on Asthma Control Measures in Relation to Baseline Blood Eosinophils Aim The objective of study 4 was to characterize the efficacy of reslizumab (3.0 mg/kg monthly) on asthma control measures in relation to baseline blood eosinophils in subjects with moderate to severe asthma. The primary endpoint was the change in $FEV_1$ from baseline to Week 16. Secondary endpoints included: ACQ-7, Rescue inhaler (SABA) use, FVC, and safety measures.

Inclusion/Exclusion Criteria

The study was performed on adults aged 18 to 65 years with uncontrolled moderate to severe asthma (ACQ score ≥1.5; at least ICS (≥440 μg fluticasone or equivalent) ±another controller (e.g. LABA); and airway reversibility (≥12% to beta-agonist)). There was no requirement for elevated blood EOS levels. There was no specific $FEV_1$ or asthma exacerbation exclusion.

Study Design and Baseline Demographics

Study was a phase 3, double-blind, 16-week, randomized, placebo-controlled study in which patients were treated with reslizumab 3.0 mg/kg or placebo every 4 weeks for 16 weeks. The baseline demographics of the patients are shown in Table 20. Baseline asthma characteristics are shown in Table 21.

TABLE 20

| Characteristic | Placebo (n = 98) | Reslizumab 3.0 mg/kg (n = 398) | Total (N = 496) |
| --- | --- | --- | --- |
| Age, mean, y | 45.1 | 44.9 | 44.9 |
| Male, % | 45 | 34 | 36 |
| Female, % | 55 | 66 | 64 |
| Race, % | | | |
| Caucasian | 74 | 65 | 67 |
| African descent | 21 | 28 | 27 |

TABLE 20-continued

| Characteristic | Placebo (n = 98) | Reslizumab 3.0 mg/kg (n = 398) | Total (N = 496) |
| --- | --- | --- | --- |
| Asian | 2 | 3 | 2 |
| Ethnicity, % | | | |
| Non-Hispanic, non-Latino | 92 | 89 | 90 |
| Hispanic | 8 | 11 | 10 |
| BMI, mean, kg/m$^2$ | 31.6 | 32.3 | 32.2 |

TABLE 21

| Characteristic* | Placebo (n = 98) | Reslizumab 3.0 mg/kg (n = 398) | Total (N = 496) |
| --- | --- | --- | --- |
| Years since diagnosis, mean | 25.8 | 26.2 | 26.1 |
| Exacerbation within previous 12 months, % | 38 | 42 | 41 |
| ACQ score, mean | 2.6 | 2.6 | 2.6 |
| Airway reversibility, % | 24.2 | 26.0 | 25.6 |
| $FEV_1$, mean, L | 2.2 | 2.1 | 2.1 |
| $FEV_1$, % predicted | 66.5 | 66.8 | 66.7 |
| Rescue medication use: Mean inhalations/previous 3 days | 2.0 | 1.9 | 1.9 |
| Blood EOS, mean (range), ×10$^9$ cells/L | 0.3 (0-1.3) | 0.3 (0-1.6) | 0.3 (0-1.6) |
| Treated with LABA, % | 82 | 77 | 78 |

ACQ = Asthma Control Questionnaire; EOS, eosinophil; $FEV_1$ = forced expiratory volume in 1 second; LABA = long-acting beta-agonist.

Results

The results of study 4 are summarized in Table 22 and FIG. 18. The primary efficacy analysis (linear regression) failed to show a significant interaction between baseline blood eosinophil count and change in $FEV_1$ at week 16 (p=0.2407; FIG. 18B). Overall change in $FEV_1$ and categorical analyses based on different blood eosinophil cut-offs were prespecified. Following 16 weeks of therapy, small, non-significant improvements in asthma control were observed in the overall population. Patients with baseline eosinophils <400/μL, as a group, showed small improvements after the addition of reslizumab that would not be considered clinically meaningful. In contrast, large treatment effects were generally observed in patients with blood eosinophil counts ≥400/μL; the low numbers of patients in the placebo arm that met this criterion limit interpretation (Table 22 and FIG. 18).

TABLE 22

| | Overall Population | | Baseline Eosinophils (<400 × 10$^9$/L) | | Baseline Eosinophils (≥400 × 10$^9$/L) | |
| --- | --- | --- | --- | --- | --- | --- |
| Efficacy Variable Randomized Patients | | | | | | |
| | Placebo N = 97 | 3 mg/kg N = 395 | Placebo | 3 mg/kg | Placebo | 3 mg/kg |
| FEV$_1$ (L) Baseline Mean (SE) Range LS Mean Change from Baseline (SE) | (n = 97) 2.172 (0.0643) (0.620-3.800) 0.175 (0.0377) | (n = 394) 2.098 (0.0350) (0.470-4.940) 0.251 (0.0200) | (n = 76) 2.182 (0.0746) (0.620-3.800) 0.215 (0.0484) | (n = 316) 2.068 (0.0372) (0.470-4.940) 0.247 (0.0255) | (n = 19) 2.153 (0.1392) (1.060-3.550) 0.002 (0.1216) | (n = 77) 2.224 (0.0928) (0.660-4.130) 0.272 (0.0557) |

TABLE 22-continued

| | Overall Population | | Baseline Eosinophils (<400 × 10⁹/L) | | Baseline Eosinophils (≥400 × 10⁹/L) | |
|---|---|---|---|---|---|---|
| | | | Efficacy Variable Randomized Patients | | | |
| | Placebo N = 97 | 3 mg/kg N = 395 | Placebo | 3 mg/kg | Placebo | 3 mg/kg |
| Treatment Effect Change (SE) | 0.076 (0.0417) | | 0.033 (0.0539) | | 0.270 (0.1320) | |
| 95% CI, P-value | [−0.006, 0.158 (0.0697)] | | [−0.073, 0.139 (0.5422)] | | [0.008, 0.532 (0.0436)] | |
| FVC (L) | (n = 97) | (n = 394) | (n = 76) | (n = 316) | (n = 19) | (n = 77) |
| Baseline Mean (SE) | 3.209 (0.0924) | 3.041 (0.0481) | 3.217 (0.1095) | 2.973 (0.0513) | 3.206 (0.1757) | 3.321 (0.1234) |
| Range | (1.320-6.170) | (0.560-5.920) | (1.320-6.170) | (0.560-5.770) | (1.810-4.780) | (1.250-5.920) |
| LS Mean Change from Baseline (SE) | 0.190 (0.0438) | 0.253 (0.0232) | 0.256 (0.0537) | 0.248 (0.0283) | 0.055 (0.1449) | 0.230 (0.0681) |
| Treatment Effect Change (SE) | 0.064 (0.0438) | | −0.009 (0.0598) | | 0.175 (0.1571) | |
| 95% CI, P-value | [−0.031, 0.159 (0.1895)] | | [−0.126, 0.109 (0.8853)] | | [−0.137, 0.487 (0.2675)] | |
| ACQ | (n = 97) | (n = 394) | (n = 76) | (n = 316) | (n = 19) | (n = 77) |
| Baseline Mean (SE) | 2.574 (0.0698) | 2.559 (0.0353) | 2.564 (0.0778) | 2.574 (0.0390) | 2.677 (0.1692) | 2.501 (0.0839) |
| Range | (1.286-4.857) | (1.286-5.286) | (1.286-4.857) | (1.286-5.286) | (1.571-4.143) | (1.571-4.143) |
| LS Mean Change from Baseline (SE) | −0.614 (0.0689) | −0.737 (0.0364) | −0.714 (0.0954) | −0.836 (0.0499) | −0.368 (0.2407) | −0.858 (0.1105) |
| Treatment Effect Change (SE) | −0.123 (0.0762) | | −0.122 (0.1065) | | −0.490 (0.2616) | |
| 95% CI, P-value | [−0.273, 0.027 (0.1072)] | | [−0.332, 0.087 (0.2511)] | | [−1.010, 0.030 (0.0643)] | |
| SABA Use (puffs/day) | (n = 96) | (n = 392) | (n = 76) | (n = 315) | (n = 18) | (n = 76) |
| Baseline Mean (SE) | 2.0 (0.19) | 1.9 (0.09) | 2.0 (0.21) | 1.9 (0.10) | 2.2 (0.44) | 1.9 (0.21) |
| Range | (0.0-8.7) | (0.0-8.0) | (0.0-8.7) | (0.0-8.0) | 0.0-6.7 | 0.0-8.0 |
| LS Mean Change from Baseline (SE) | −0.2 (0.15) | −0.3 (0.08) | −0.4 (0.21) | −0.2 (0.11) | −0.1 (0.43) | 0-.8 (0.19) |
| Treatment Effect Change (SE) | −0.054 (0.1661) | | 0.216 (0.2300) | | −0.708 (0.4587) | |
| 95% CI, P-value | [−0.380, 0.273 (0.7468)] | | [−0.236, 0.668 (0.3484)] | | [−1.619, 0.204, (0.1264)] | |

Adverse Events

The adverse events are summarized in Table 23. Serious AEs, with reslizumab treatment: 16 events (4%) spanning multiple SOC without apparent pattern. Of interest: Anaphylaxis (×2) (1 related (below); 1 immunotherapy); and colon cancer (not related). Discontinuation due to AEs: spanned multiple SOC without apparent pattern.

TABLE 23

| Adverse Event, n (%) | Placebo n = 97 | Reslizumab (3 mg/kg) n = 39S |
|---|---|---|
| ≥1 AE, ANY | 72 (74) | 218 (55) |
| ≥1 treatment-related AE | 16 (16) | 28 (7) |
| ≥1 serious AE | 4 (4) | 16 (4) |
| ≥1 discontinuation due to AE | 12 (12) | 29 (7) |

The most frequent AE by preferred term frequency ≥2% for reslizumab are shown in Table 24.

TABLE 24

| n (%) | Placebo | Reslizumab (3 mg/kg) |
|---|---|---|
| asthma | 19 (20) | 50 (13) |
| URTI | 11 (11) | 42 (11) |
| sinusitis | 7 (7) | 22 (6) |
| bronchitis | 6 (6) | 14 (4) |
| nasopharyngitis | 5 (5) | 13 (3) |
| headache | 4 (4) | 13 (3) |
| UTI | 0 | 10 (3) |
| acute sinusitis | 3 (3) | 6 (2) |
| influenza | 3 (3) | 8 (2) |
| back pain | 3 (3) | 6 (2) |
| rhinitis allergic | 3 (3) | 9 (2) |
| cough | 1 (1) | 6 (2) |

Conclusion

Interaction between treatment and baseline blood EOS count was not significant based on simple linear regression. Treatment effects of reslizumab were small in the overall population (unselected for baseline EOS). Treatment effects were small in patients with baseline EOS ≤400/μL, as a group. The largest improvements in lung function and asthma control occurred in subjects with baseline EOS ≥400/μL (the small number of subjects (n=13 at week 16) with EOS ≥400/μL, in the placebo group limits interpretation; 30% withdrawal in placebo group with baseline EOS ≥400/μL and 10% for reslizumab group with baseline ≥400/μt). Four monthly doses of reslizumab were well tolerated in subjects with moderate to severe asthma.

Example 4: Comparison of Reslizumab and Mepolizumab

A comparison of reslizumab and mepolizumab inclusion and design are summarized in Table 25.

TABLE 25

| Reslizumab Inclusion Criteria | Mepolizumab Inclusion Criteria |
|---|---|
| Moderate to severe asthma | Severe, uncontrolled refractory asthma |
| Asthma patients age 12-75 | Asthma patients ≥ age 12 |
| Physiology | Physiology |
| Reversible to SABA (12%) during screening | Reversible to SABA, AHR, PEF or $FEV_1$ variability |
| No $FEV_1$ upper limit | Evidence of persistent airflow obstruction ($FEV_1$ % predicted <80% for age 18 or older, <90% for age 12 to 17 or $FEV_1$/FVC ratio <0.8 |

TABLE 25-continued

| Reslizumab Inclusion Criteria Moderate to severe asthma | Mepolizumab Inclusion Criteria Severe, uncontrolled refractory asthma |
|---|---|
| Blood eosinophil level ≥400/μL | EOS ≥ 300 in prior 12 months or 150 at V1 |
| At least medium doses of ICS (≥440 μg of fluticasone or equivalent) ± another controller | High dose ICS + another controller |
| ≥1 asthma exacerbation previous 1 months | ≥2 exacerbations previous 12 months |
| Inadequately controlled (ACQ ≥ 1.5) | No apparent inclusion for current control |
| OCS dependent asthma allowed | OCS dependent asthma allowed |
| Iv dosing is weight based 3 mg/kg | Fixed dose iv 75 mg or sc 100 mg minimum weight of 45 kilogram (kg) |
| Reslizumab Design reslizumab 3.0 mg/kg iv or placebo every 4 weeks x 13 doses EOT 52 weeks | Mepolizumab Design mepolizumab 75 mg iv, 100 mg sc or PBO every 4 weeks x 8 Doses EOT 32 weeks |

A comparison of primary efficacy CAE definitions in reslizumab and mepolizumab studies are summarized in Table 26.

TABLE 26

| Reslizumab | Mepolizumab |
|---|---|
| Medical intervention | |
| 1. use of systemic, or an increase in the use of inhaled, corticosteroid and/or 2. asthma-related emergency treatment including at least 1 of the following: an unscheduled visit to the physician's office for nebulizer treatment or other urgent treatment to prevent worsening of asthma symptoms a visit to the emergency room for asthma related treatment an asthma-related hospitalization PLUS evidence of asthma worsening | Use of systemic corticosteroid and/or a hospitalization or ER visit |
| decrease in FEV$_1$ by 20% or more from baseline decrease in the peak expiratory flow rate (PEFR) by 30% or more from baseline on 2 consecutive days worsening of symptoms or other clinical signs per physician evaluation of the event | E-Diary based decreased peak flow increase in rescue medication increased frequency of nocturnal awakening due to asthma ↑ asthma symptoms |

Bold font - Independently adjudicated

A comparison of primary and key secondary efficacy in reslizumab and mepolizumab studies are summarized in Table 27.

TABLE 27

| | CAE primary | CAE requiring sys. cortico. | FEV$_1$ change from baseline at time point (ml)* | | |
|---|---|---|---|---|---|
| | | | 16 wk | 32 wk | 52 wk |
| Study 3082 Reslizumab 3 mg/kg | 50% p < .0001 | 55% p < .0001 | 72 p = 0.0483 | 56 ns | 145 p = 0.0004 |
| Study 3083 Reslizumab 3 mg/kg | 60% p < .0001 | 61% p < .0001 | 101 p = 0.0109 | 76 ns | 123 p = 0.0016 |
| Study 115588 MEPO 100 mg sc MEPO 75 mg iv | | 53% p < .001 47% p < .001 | — — | 98 100 | — — |
| DREAM MEPO 75 mg iv | | 48% p < .0001 | — | — | 61 ns |
| Study 3081 Reslizumab 3 mg/kg | | | 165 p = 0.018 | | |

*MEPO silent on overall FEV improvements: 'at' time point contrasted above. MEPO 100 mg sc (Study 115588) and 75 mg (DREAM) appear to reduce CAE requiring hospitalization and ER visits. Reslizumab hospital and ER subanalyses pending.

Summary

A robust improvement in FEV$_1$ as early as week 4 that was maintained to week 16 was observed with reslizumab treatment in asthma patients with elevated Eosinophils >400/μl (Eosinophilic asthma) already treated with ICS/LABA or ICS±another controller (e.g. LTRA). Reslizumab also uniquely improved FEF$_{25\%-75\%}$ and, in particular, Forced Vital Capacity (FVC), consistent with improvements in small airways obstruction (FEF$_{25\%-75\%}$) and decreased hyperinflation (overall FVC improvement) perhaps due to improvements in remodeling that was most prominent with the 3 mg/kg dose. Furthermore, Studies 2 and 3 indicated that the lung function benefit, in terms of FEV$_1$, was sustained through 52 weeks.

The differential effects in patients with >400 eosinophils vs <400 eosinophils seen in study 4 on a number of measures of lung function and asthma control suggest that these effects are unique to the patient population of eosinophilic asthmatics. Measures of control (ACQ, rescue use) and lung function including FVC, and FEF$_{25\%-75\%}$ were uniquely impacted by reslizumab in asthma patients with elevated eosinophils >400/μl (eosinophilic asthma).

The results from study 1 demonstrated a significant and meaningful effect on FEV$_1$ as early as week 4 that was maintained to week 16 in asthma patients with elevated eosinophils >400/μl. This finding is remarkable in that it was seen in patients either on ICS/LABA (approx 80%) or ICS with or without controller(s) (e.g. LTRA—approximately 16% or LAMA approximately 4%). Additionally, the disclosed studies showed that reslizumab uniquely improves FEF$_{25\%-75\%}$ and, in particular, FVC, consistent with improvements in small airways obstruction (FEF$_{25\%-75\%}$) and decreased hyperinflation/improvement in remodeling (overall FVC improvement) that was most prominent with the 3 mg/kg dose.

Many clinical studies on other agents have demonstrated decreasing magnitude of response in more severe/compromised patients with no response in patients of this severity (e.g. LTRA). In contrast, as demonstrated in study 1, the improvements in FEV$_1$ seen with 3 mg/kg IV reslizumab in patients with eosinophilic asthma on lung function were consistent even in patients with compromised lung function; this was confirmed by the results seen with the 3 mg/kg dose in patients with baseline FEV$_1$≤85%.

As seen in study 1, reslizumab demonstrated meaningful improvements from baseline in other control measures including the Asthma Control Questionnaire (ACQ) and quality of life (AQLQ) that represents a unique outcome in this severe patient population.

Example 5: Treatment of Patients Having Late-Onset Eosinophilic Asthma

Objectives

Late-onset asthma with elevated blood eosinophils is a distinct and difficult-to-treat asthma phenotype. The objective of example 5 was to determine whether or not treatment with reslizumab reduces exacerbations and improves lung function in patients (pts) with late-onset asthma inadequately controlled on an inhaled corticosteroid (ICS)-based regimen and with elevated blood eosinophils.

Methods

Data were pooled from two 52-week placebo-controlled trials of reslizumab IV 3 mg/kg (every 4 weeks) in patients (12-75 years old) with inadequately controlled asthma (ACQ7 ≥1.5 and ≥1 asthma exacerbation within 12 months) and screening blood eosinophil counts ≥400/μL. All events were independently adjudicated. Annual rate of asthma exacerbations (defined as worsening events requiring additional corticosteroid and/or urgent asthma treatment) (FIG. 19A) and overall change in lung function (FEV$_1$) (FIG. 19B) were stratified by age of asthma onset (<40 or ≥40 years old).

Results

Overall, 476 and 477 patients were randomized to placebo and reslizumab, respectively. 273 patients had late-onset asthma (age ≥40 years old at diagnosis); baseline characteristics for this group included mean age of 58.2 years old, 59% female, mean BMI: 27.9, ACQ6 score: 2.5, and FEV$_1$: 1.84 L (67% predicted). Efficacy results by treatment and age of onset are displayed in FIG. 19.

Conclusion

Reslizumab markedly reduced asthma exacerbations and improved lung function in patients with late-onset asthma and elevated blood eosinophils.

Example 6: Influence of Baseline Eosinophil Counts Higher than 400/μL

Methods

Post hoc analysis of pooled data from studies 3082 and 3083. CAE rate ratios and FEV1 treatment effect (reslizumab-placebo) were stratified by increasingly exclusive eosinophil category (≥400, ≥500, ≥600, ≥700, ≥800)

Results

As illustrated in FIG. 20A, no further effect of increasing baseline blood eosinophils beyond 400/μl was observed on CAE. A modest increase in FEV$_1$ improvement with increasing baseline blood eosinophils beyond 400/μl (~30-50 ml) was observed, however, as illustrated in FIG. 20B.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

---

What is claimed:

1. A method of treating moderate to severe eosinophilic asthma in a patient comprising:
    administering a therapeutically effective dose of reslizumab to the patient, wherein
       prior to the administering, the patient's symptoms are inadequately controlled with a current asthma therapeutic and the patient's blood eosinophil levels are equal to or greater than 400/μl; and
       following the administering, the patient exhibits a significantly improved $FEV_1$ treatment effect and wherein the patient's use of systemic corticosteroids is reduced by about 50% as compared to a patient not receiving reslizumab.

2. The method of claim 1, wherein the patient's blood eosinophil levels are equal to or greater than 500/μl, 600/μl, 700/μl, or 800/μl.

3. The method of claim 1, wherein the therapeutically effective dose of reslizumab is about 0.3 mg/kg to about 3 mg/kg.

4. The method of claim 1, wherein the therapeutically effective dose of reslizumab is administered intravenously or subcutaneously.

5. The method of claim 1, wherein the therapeutically effective dose of reslizumab is administered once about every 4 weeks.

6. The method of claim 1, wherein the current asthma therapeutic comprises an inhaled corticosteroid.

7. The method of claim 6, wherein the current asthma therapeutic comprises a medium dose inhaled corticosteroid.

8. The method of claim 7, wherein the inhaled corticosteroid is at least equivalent to about 440 μg fluticasone.

9. The method of claim 6, wherein the inhaled corticosteroid comprises a high dose of inhaled corticosteroid.

10. The method of claim 6, wherein the current asthma therapeutic further comprises a long acting beta 2 adrenoceptor agonist.

11. The method of claim 1, wherein administration of the therapeutically effective dose of reslizumab also leads to an improvement in lung function, as assessed by forced vital capacity, forced expiratory flow rate, or any combination thereof.

12. The method of claim 11, wherein the improvement in lung function is equal to or greater than about 5% as compared to a patient not receiving reslizumab.

13. The method of claim 1, wherein administration of the therapeutically effective dose of reslizumab leads to a reduction of clinical asthma exacerbations, reduction of use of systemic corticosteroids, improved asthma control questionnaire score, improved asthma quality of life questionnaire score, or any combination thereof.

14. The method of claim 13, wherein the clinical asthma exacerbations are reduced by about 50% as compared to a patient not receiving reslizumab.

* * * * *

SEQUENCE LISTING

```
<160> NUMBER OF SEQ ID NOS: 2

<210> SEQ ID NO 1
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Ser Leu Thr Ser Asn
            20                  25                  30

Ser Val Asn Trp Ile Arg Gln Ala Pro Gly Lys Gly Leu Glu Trp Val
        35                  40                  45

Gly Leu Ile Trp Ser Asn Gly Asp Thr Asp Tyr Asn Ser Ala Ile Lys
    50                  55                  60

Ser Arg Phe Thr Ile Ser Arg Asp Thr Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Glu Tyr Tyr Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
    195                 200                 205

Lys Val Asp Lys Arg Val Glu Ser Lys Tyr Gly Pro Pro Cys Pro Ser
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 2
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Ser Tyr
            20                  25                  30

Leu Ala Trp Tyr Gln Gln Lys Pro Gly Lys Ala Pro Lys Leu Leu Ile
        35                  40                  45
```

-continued

```
Tyr Gly Ala Asn Ser Leu Gln Thr Gly Val Pro Ser Arg Phe Ser Gly
     50                  55                  60

Ser Gly Ser Ala Thr Asp Tyr Thr Leu Thr Ile Ser Ser Leu Gln Pro
 65              70                  75                      80

Glu Asp Phe Ala Thr Tyr Tyr Cys Gln Gln Ser Tyr Lys Phe Pro Asn
             85                  90                  95

Thr Phe Gly Gln Gly Thr Lys Val Glu Val Lys Arg Thr Val Ala Ala
             100                 105                 110

Pro Ser Val Phe Ile Phe Pro Pro Ser Asp Glu Gln Leu Lys Ser Gly
         115             120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
             165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
             195                 200                 205

Phe Asn Arg Gly Glu Cys
     210
```